United States Patent
Wang et al.

(10) Patent No.: US 9,988,403 B2
(45) Date of Patent: Jun. 5, 2018

(54) COMPOSITIONS AND METHODS FOR TREATING CANCER WITH ABERRANT LIPOGENIC SIGNALING

(71) Applicant: Thomas Jefferson University, Philadelphia, PA (US)

(72) Inventors: Chenguang Wang, Cherry Hill, NJ (US); Jie Zhou, Cherry Hill, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 0 days. days.

(21) Appl. No.: 15/434,454

(22) Filed: Feb. 16, 2017

(65) Prior Publication Data

US 2017/0166593 A1    Jun. 15, 2017

Related U.S. Application Data

(63) Continuation of application No. 14/410,352, filed as application No. PCT/US2013/044887 on Jun. 10, 2013, now Pat. No. 9,750,758.

(60) Provisional application No. 61/663,875, filed on Jun. 25, 2012.

(51) Int. Cl.
C07F 5/04    (2006.01)
A61K 31/69   (2006.01)
C07F 7/08    (2006.01)

(52) U.S. Cl.
CPC ............... *C07F 5/04* (2013.01); *C07F 7/082* (2013.01)

(58) Field of Classification Search
None
See application file for complete search history.

(56) References Cited

U.S. PATENT DOCUMENTS

| | | | |
|---|---|---|---|
| 3,203,908 A | 8/1965 | Kitasaki et al. |
| 9,353,132 B2 | 5/2016 | Wang et al. |
| 2007/0003783 A1 | 1/2007 | Morishita et al. |
| 2007/0027299 A1 | 2/2007 | Morishita et al. |
| 2008/0234229 A1 | 9/2008 | Sarshar |
| 2009/0131475 A1 | 5/2009 | Uesugi et al. |
| 2011/0279019 A1 | 11/2011 | Kottas et al. |
| 2012/0149663 A1 | 6/2012 | Brown et al. |
| 2014/0051661 A1 | 2/2014 | Das et al. |

FOREIGN PATENT DOCUMENTS

| | | |
|---|---|---|
| DE | 10 2008 052315 A1 | 4/2010 |
| GB | 2276721 A | 10/1994 |
| JP | 2006/512395 A | 4/2006 |
| JP | 2009/523167 A | 6/2009 |
| JP | 2010/111620 A | 5/2010 |
| JP | 2011/037881 A | 2/2011 |
| WO | 2001/083410 A1 | 11/2001 |
| WO | 2004/005277 A1 | 1/2004 |
| WO | 2004/061048 A1 | 7/2004 |
| WO | 2004/092246 A1 | 10/2004 |
| WO | 2007/028104 A2 | 3/2007 |
| WO | 2007/081179 A1 | 7/2007 |
| WO | 2008/063300 A2 | 5/2008 |
| WO | 2010/053210 A1 | 5/2010 |
| WO | 2011/022502 A1 | 2/2011 |
| WO | 2012/112670 A1 | 8/2012 |

OTHER PUBLICATIONS

Kuhajda "Fatty-acid synthase and human cancer: new perspectives on its role in tumor biology." Nutrition 16 (3):202-208 (2000).
CAS Registry No. 1045601-92-0; STN Entry Date: Sep. 1, 2008; 1H-1-Silaindene, 1,1-dimethyl-3-(2-propen-1-yl)-2-[4-(4,4,5,5-tetramethyl-1,3,2-dioxaboloran-2-yl)phenyl]-.
CAS Registry No. 1092390-02-7; STN Entry Date: Dec. 31, 2008; 1,3,2-Dioxaborolane, 4,4,5,5-tetramethyl-2-[4-(2-naphthalenyl)phenyl]-.
CAS Registry No. 288105-07-7; STN Entry Date: Sep. 1, 2000; Benzeneacetonitrile, α-(diphenylmethylene)-4-(4,4,5,5-tetramethyl-1,3,2-dioxaborolan-2-yl).
CAS Registry No. 349666-24-6 ; STN Entry Date: Aug. 1, 2001; 1,3,2-Dioxaborolane, 4,4,5,5-tetramethyl-2-(1-pyrenyl)-.
CAS Registry No. 719315-72-7; STN Entry Date: Jul. 30, 2004; 1,3,2-Dioxaborinane, 2,2'-(11,11-dihexyl-11H-benzo[a]fluorene-3,9-diyl)bis[5,5-dimethyl-.

(Continued)

*Primary Examiner* — Valerie Rodriguez-Garcia
(74) *Attorney, Agent, or Firm* — Nixon Peabody LLP; David S. Resnick; Nicole D. Kling

(57) ABSTRACT

The technology described herein relates to dimethyl boronate esters of the following formula for the treatment of cancers expressing abnormally high levels of SREBP1:

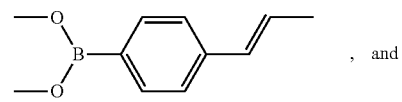

, and

BF-175

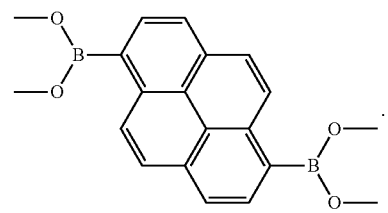

3 Claims, 12 Drawing Sheets

(56) References Cited

OTHER PUBLICATIONS

CAS Registry No. 942506-80-1; STN Entry Date: Jul. 17, 2007; 1,3,2-Dioxaborolane, 2-[7-(1,1-dimethylethyl)-1-pyrenyl]-4,4,5,5-tetramethyl-.

Das et al., Bioorg Med Chem Lett., 21(18):5638-41, 2011, "Design, synthesis and biological study of pinacolyl boronate-substituted stilbenes as novel lipogenic inhibitors".

Eberhard et al., Oncotarget., 2(3):186-96, 2011, "Inhibition of SREBP1 sensitizes cells to death ligands".

Iwasawa et al., "Straightforward access to functionalized pentaarylbenzene derivatives through a quick lithiation", Tetrahedron Letters 49(36):5244-5246 (2008).

Ji et al., "Structure-activity relationships of boronic acids", Database CA [Online] Chemical Abstracts Service, Columbus Ohio, US, Database accession No. 1997:766280.

Jiang et al. "Boron-based 4-Hydroxytamoxifen bioisosteres for treatment of de Novo Tamoxifen resistant breast cancer." ACS Medicinal Chemistry Letters 3(5):392-396 (2012).

Kuznetsov et al., Russian Chemical Bulletin, 54(3):678-683, (2005). "Synthesis of 6, 7-benzo-3-borabicyclo{3.3.1}noname and its 3-aza analog from 2-allypheny(dially)borane. Intramolecular arylboration of the C=C bond".

Laplante & Sabatini, Curr Biol., 19(22):R1046-52, 2009, "An emerging role of mTOR in lipid biosynthesis".

Matsuda et al. "Gold-catalysed intramolecular trans-allylsilylation of alkynes forming 3-allyl-1-silaindenes." Chemical Communications 24:2744-2746 (2008).

O'Connell et al., "Design and synthesis of boronic acid inhibitors of endothelial lipase." Bioorganic & Medicinal Chemistry Letters 22(3):1397-1401 (2012).

Oehlke et al., "Nitro-substituted stilbeneboronate pinacol esters and their fluoro-adducts. fluoride ion induced polarity enhancement of arylboronate esters." The Journal of Organic Chemistry 72(12):4328-4339 (2007).

Shen et al.,Journal of the American Chemical Society, 133(42): 17037-17044, (2011). "Facile Regio- amd Stereoselective Hydromentalation of Alkynes with a Combination of Carboxylic Acids and Group 10 Transition metal Complexes: Selective Hydrogenation of Alkynes with Formal Acid".

Sun et al., "An Ambipolar Transporting Naptho[2,3-c][1,2,5] thiadiazole Derivative with High Electron and Hole Mobilities", Organic Letters 11(10):2069-2972 (2009).

Whittle et al., "Cyclometallated, bis-terdentate iridium complexes as linearly expandable cores for the constructions of multimetallic assemblies", Dalton Trans. (20):3929-3940 (2009).

Yang et al., Exp Cell Res., 282(2):132-137, 2003, "Regulation of fatty acid synthase expression in breast cancer by sterol regulatory element binding protein-1c".

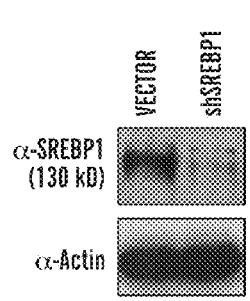
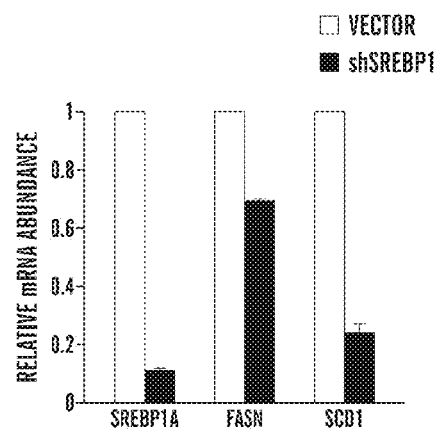
FIG. 2C
FIG. 2D
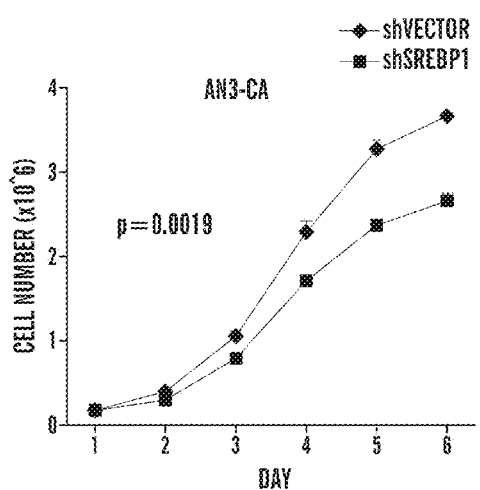
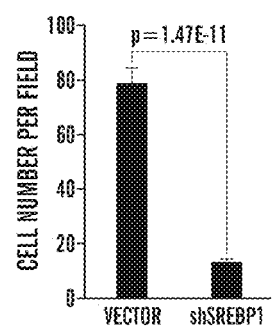
FIG. 2E
FIG. 2F

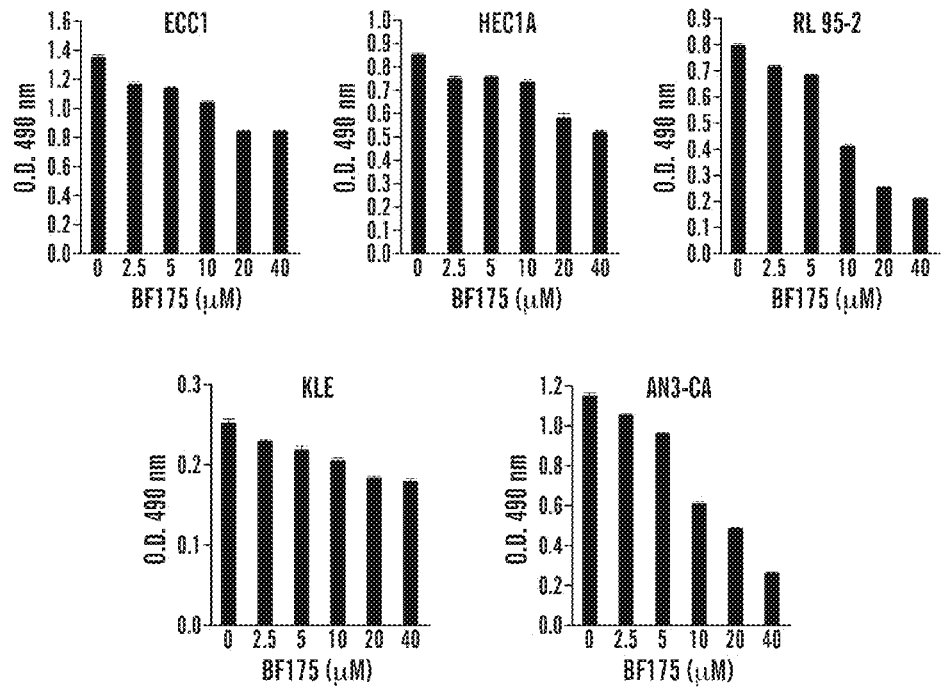
*FIG. 4A*
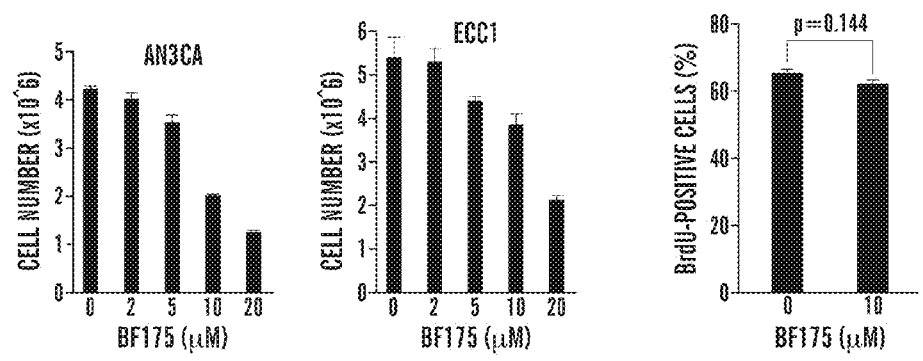
*FIG. 4B*  *FIG. 4C*

SEQUENCE LISTING

<160> NUMBER OF SEQ ID NOS: 30

<210> SEQ ID NO 1
<211> LENGTH: 1177
<212> TYPE: PRT
<213> ORGANISM: Homo sapiens

<400> SEQUENCE: 1

```
Met Asp Glu Pro Pro Phe Ser Glu Ala Ala Leu Glu Gln Ala Leu Gly
1               5                   10                  15

Glu Pro Cys Asp Leu Asp Ala Ala Leu Leu Thr Asp Ile Glu Gly Glu
            20                  25                  30

Val Gly Ala Gly Arg Gly Arg Ala Asn Gly Leu Asp Ala Pro Arg Ala
        35                  40                  45

Gly Ala Asp Arg Gly Ala Met Asp Cys Thr Phe Glu Asp Met Leu Gln
    50                  55                  60

Leu Ile Asn Asn Gln Asp Ser Asp Phe Pro Gly Leu Phe Asp Pro Pro
65                  70                  75                  80

Tyr Ala Gly Ser Gly Ala Gly Gly Thr Asp Pro Ala Ser Pro Asp Thr
                85                  90                  95

Ser Ser Pro Gly Ser Leu Ser Pro Pro Ala Thr Leu Ser Ser Ser
            100                 105                 110

Leu Glu Ala Phe Leu Ser Gly Pro Gln Ala Ala Pro Ser Pro Leu Ser
        115                 120                 125

Pro Pro Gln Pro Ala Pro Thr Pro Leu Lys Met Tyr Pro Ser Met Pro
    130                 135                 140

Ala Phe Ser Pro Gly Pro Gly Ile Lys Glu Glu Ser Val Pro Leu Ser
145                 150                 155                 160

Ile Leu Gln Thr Pro Thr Pro Gln Pro Leu Pro Gly Ala Leu Leu Pro
                165                 170                 175

Gln Ser Phe Pro Ala Pro Ala Pro Pro Gln Phe Ser Ser Thr Pro Val
            180                 185                 190

Leu Gly Tyr Pro Ser Pro Pro Gly Gly Phe Ser Thr Gly Ser Pro Pro
        195                 200                 205
```

```
Gly Asn Thr Gln Gln Pro Leu Pro Gly Leu Pro Leu Ala Ser Pro Pro
    210                 215                 220

Gly Val Pro Pro Val Ser Leu His Thr Gln Val Gln Ser Val Val Pro
225                 230                 235                 240

Gln Gln Leu Leu Thr Val Thr Ala Ala Pro Thr Ala Ala Pro Val Thr
                245                 250                 255

Thr Thr Val Thr Ser Gln Ile Gln Gln Val Pro Val Leu Leu Gln Pro
            260                 265                 270

His Phe Ile Lys Ala Asp Ser Leu Leu Thr Ala Met Lys Thr Asp
        275                 280                 285

Gly Ala Thr Val Lys Ala Gly Leu Ser Pro Leu Val Ser Gly Thr
    290                 295                 300

Thr Val Gln Thr Gly Pro Leu Pro Thr Leu Val Ser Gly Thr Ile
305                 310                 315                 320

Leu Ala Thr Val Pro Leu Val Val Asp Ala Glu Lys Leu Pro Ile Asn
                325                 330                 335

Arg Leu Ala Ala Gly Ser Lys Ala Pro Ala Ser Ala Gln Ser Arg Gly
            340                 345                 350

Glu Lys Arg Thr Ala His Asn Ala Ile Glu Lys Arg Tyr Arg Ser Ser
        355                 360                 365

Ile Asn Asp Lys Ile Ile Glu Leu Lys Asp Leu Val Val Gly Thr Glu
    370                 375                 380

Ala Lys Leu Asn Lys Ser Ala Val Leu Arg Lys Ala Ile Asp Tyr Ile
385                 390                 395                 400

Arg Phe Leu Gln His Ser Asn Gln Lys Leu Lys Gln Glu Asn Leu Ser
                405                 410                 415

Leu Arg Thr Ala Val His Lys Ser Lys Ser Leu Lys Asp Leu Val Ser
            420                 425                 430

Ala Cys Gly Ser Gly Gly Asn Thr Asp Val Leu Met Glu Gly Val Lys
        435                 440                 445

Thr Glu Val Glu Asp Thr Leu Thr Pro Pro Ser Asp Ala Gly Ser
    450                 455                 460

Pro Phe Gln Ser Ser Pro Leu Ser Leu Gly Ser Arg Gly Ser Gly Ser
465                 470                 475                 480

Gly Gly Ser Gly Ser Asp Ser Glu Pro Asp Ser Pro Val Phe Glu Asp
                485                 490                 495

Ser Lys Ala Lys Pro Glu Gln Arg Pro Ser Leu His Ser Arg Gly Met
            500                 505                 510

Leu Asp Arg Ser Arg Leu Ala Leu Cys Thr Leu Val Phe Leu Cys Leu
        515                 520                 525

Ser Cys Asn Pro Leu Ala Ser Leu Leu Gly Ala Arg Gly Leu Pro Ser
    530                 535                 540

Pro Ser Asp Thr Thr Ser Val Tyr His Ser Pro Gly Arg Asn Val Leu
545                 550                 555                 560

Gly Thr Glu Ser Arg Asp Gly Pro Gly Trp Ala Gln Trp Leu Leu Pro
                565                 570                 575

Pro Val Val Trp Leu Leu Asn Gly Leu Leu Val Leu Val Ser Leu Val
            580                 585                 590

Leu Leu Phe Val Tyr Gly Glu Pro Val Thr Arg Pro His Ser Gly Pro
        595                 600                 605

Ala Val Tyr Phe Trp Arg His Arg Lys Gln Ala Asp Leu Asp Leu Ala
    610                 615                 620
```

```
Arg Gly Asp Phe Ala Gln Ala Ala Gln Gln Leu Trp Leu Ala Leu Arg
625                 630                 635                 640

Ala Leu Gly Arg Pro Leu Pro Thr Ser His Leu Asp Leu Ala Cys Ser
            645                 650                 655

Leu Leu Trp Asn Leu Ile Arg His Leu Leu Gln Arg Leu Trp Val Gly
                660                 665                 670

Arg Trp Leu Ala Gly Arg Ala Gly Leu Gln Gln Asp Cys Ala Leu
    675                 680                 685

Arg Val Asp Ala Ser Ala Ser Ala Arg Asp Ala Ala Leu Val Tyr His
690                 695                 700

Lys Leu His Gln Leu His Thr Met Gly Lys His Thr Gly Gly His Leu
705                 710                 715                 720

Thr Ala Thr Asn Leu Ala Leu Ser Ala Leu Asn Leu Ala Glu Cys Ala
                725                 730                 735

Gly Asp Ala Val Ser Val Ala Thr Leu Ala Glu Ile Tyr Val Ala Ala
                740                 745                 750

Ala Leu Arg Val Lys Thr Ser Leu Pro Arg Ala Leu His Phe Leu Thr
            755                 760                 765

Arg Phe Phe Leu Ser Ser Ala Arg Gln Ala Cys Leu Ala Gln Ser Gly
770                 775                 780

Ser Val Pro Pro Ala Met Gln Trp Leu Cys His Pro Val Gly His Arg
785                 790                 795                 800

Phe Phe Val Asp Gly Asp Trp Ser Val Leu Ser Thr Pro Trp Glu Ser
                805                 810                 815

Leu Tyr Ser Leu Ala Gly Asn Pro Val Asp Pro Leu Ala Gln Val Thr
            820                 825                 830

Gln Leu Phe Arg Glu His Leu Leu Glu Arg Ala Leu Asn Cys Val Thr
        835                 840                 845

Gln Pro Asn Pro Ser Pro Gly Ser Ala Asp Gly Asp Lys Glu Phe Ser
850                 855                 860

Asp Ala Leu Gly Tyr Leu Gln Leu Leu Asn Ser Cys Ser Asp Ala Ala
865                 870                 875                 880

Gly Ala Pro Ala Tyr Ser Phe Ser Ile Ser Ser Met Ala Thr Thr
                885                 890                 895

Thr Gly Val Asp Pro Val Ala Lys Trp Trp Ala Ser Leu Thr Ala Val
            900                 905                 910

Val Ile His Trp Leu Arg Arg Asp Glu Ala Ala Glu Arg Leu Cys
        915                 920                 925

Pro Leu Val Glu His Leu Pro Arg Val Leu Gln Glu Ser Glu Arg Pro
        930                 935                 940

Leu Pro Arg Ala Ala Leu His Ser Phe Lys Ala Ala Arg Ala Leu Leu
945                 950                 955                 960

Gly Cys Ala Lys Ala Glu Ser Gly Pro Ala Ser Leu Thr Ile Cys Glu
            965                 970                 975

Lys Ala Ser Gly Tyr Leu Gln Asp Ser Leu Ala Thr Thr Pro Ala Ser
            980                 985                 990

Ser Ser Ile Asp Lys Ala Val Gln Leu Phe Leu Cys Asp Leu Leu Leu
        995                 1000                1005

Val Val Arg Thr Ser Leu Trp Arg Gln Gln Gln Pro Pro Ala Pro
    1010                1015                1020

Ala Pro Ala Ala Gln Gly Thr Ser Ser Arg Pro Gln Ala Ser Ala
    1025                1030                1035

Leu Glu Leu Arg Gly Phe Gln Arg Asp Leu Ser Ser Leu Arg Arg
```

| | | | | | | | | | | |
|---|---|---|---|---|---|---|---|---|---|---|
| | | 1040 | | | 1045 | | | 1050 | | |
| Leu | Ala | Gln | Ser | Phe | Arg | Pro | Ala | Met | Arg | Arg | Val | Phe | Leu | His |
| | 1055 | | | | 1060 | | | | 1065 | |
| Glu | Ala | Thr | Ala | Arg | Leu | Met | Ala | Gly | Ala | Ser | Pro | Thr | Arg | Thr |
| 1070 | | | | | 1075 | | | | | 1080 | |
| His | Gln | Leu | Leu | Asp | Arg | Ser | Leu | Arg | Arg | Ala | Gly | Pro | Gly |
| | 1085 | | | | | 1090 | | | | | 1095 | |
| Gly | Lys | Gly | Gly | Ala | Val | Ala | Glu | Leu | Glu | Pro | Arg | Pro | Thr | Arg |
| 1100 | | | | | 1105 | | | | | 1110 | |
| Arg | Glu | His | Ala | Glu | Ala | Leu | Leu | Leu | Ala | Ser | Cys | Tyr | Leu | Pro |
| | 1115 | | | | 1120 | | | | | 1125 | |
| Pro | Gly | Phe | Leu | Ser | Ala | Pro | Gly | Gln | Arg | Val | Gly | Met | Leu | Ala |
| 1130 | | | | | 1135 | | | | | 1140 | |
| Glu | Ala | Ala | Arg | Thr | Leu | Glu | Lys | Leu | Gly | Asp | Arg | Arg | Leu | Leu |
| | 1145 | | | | 1150 | | | | | 1155 | |
| His | Asp | Cys | Gln | Gln | Met | Leu | Met | Arg | Leu | Gly | Gly | Gly | Thr | Thr |
| | 1160 | | | | 1165 | | | | | 1170 | |
| Val | Thr | Ser | Ser |
| 1175 |

<210> SEQ ID NO 2
<211> LENGTH: 5012
<212> TYPE: DNA
<213> ORGANISM: Homo sapiens

<400> SEQUENCE: 2

```
agcagagctg cggccggggg aacccagttt ccgaggaact tttcgccggc gccgggccgc     60
ctctgaggcc agggcaggac acgaacgcgc ggagcggcgg cggcgactga gagccggggc    120
cgcggcggcg ctccctagga agggccgtac gaggcggcgg gccggcgggg cctcccggag    180
gaggcggctg cgccatggac gagccaccct tcagcgaggc ggctttggag caggcgctgg    240
gcgagccgtg cgatctggac gcggcgctgc tgaccgacat cgaaggtgaa gtcggcgcgg    300
ggaggggtag ggccaacggc ctggacgccc aagggcgggg cgcagatcgc ggagccatgg    360
attgcacttt cgaagacatg cttcagctta tcaacaacca agacagtgac ttccctggcc    420
tatttgaccc accctatgct gggagtgggg caggggcac agaccctgcc agccccgata    480
ccagctcccc aggcagcttg tctccacctc ctgccacatt gagctcctct cttgaagcct    540
tcctgagcgg gccgcaggca gcgccctcac ccctgtcccc tcccagcct gcacccactc    600
cattgaagat gtaccgtcc atgccgctt tctcccctgg gctggtatc aaggaagagt    660
cagtgccact gagcatcctg cagaccccca ccccacagcc cctgccaggg gccctcctgc    720
cacagagctt cccagcccca gccccaccgc agttcagctc caccctgtg ttaggctacc    780
ccagccctcc gggaggcttc tctacaggaa gccctcccgg gaacacccag cagccgctgc    840
ctggcctgcc actggcttcc ccgcaggggg tcccgcccgt ctccttgcac acccaggtcc    900
agagtgtggt ccccccagcag ctactgacag tcacagctgc ccccacggca gcccctgtaa    960
cgaccactgt gacctcgcag atccagcagg tcccggtcct gctgcagccc cacttcatca   1020
aggcagactc gctgcttctg acagccatga agacagacg agccactgtg aaggcggcag   1080
gtctcagtcc cctggtctct ggcaccactg tgcagacagg gcctttgccg accctggtga   1140
gtggcggaac catcttggca acagtcccac tggtcgtaga tgcggagaag ctgcctatca   1200
accggctcgc agctggcagc aaggcccgg cctctgccca gagccgtgga gagaagcgca   1260
```

| | | | | | |
|---|---|---|---|---|---|
| cagcccacaa | cgccattgag | aagcgctacc | gctcctccat | caatgacaaa | atcattgagc | 1320 |
| tcaaggatct | ggtggtgggc | actgaggcaa | agctgaataa | atctgctgtc | ttgcgcaagg | 1380 |
| ccatcgacta | cattcgcttt | ctgcaacaca | gcaaccagaa | actcaagcag | gagaacctaa | 1440 |
| gtctgcgcac | tgctgtccac | aaaagcaaat | ctctgaagga | tctggtgtcg | gcctgtggca | 1500 |
| gtggagggaa | cacagacgtg | ctcatggagg | gcgtgaagac | tgaggtggag | gacacactga | 1560 |
| ccccaccccc | ctcggatgct | ggctcacctt | tccagagcag | ccccttgtcc | cttggcagca | 1620 |
| ggggcagtgg | cagcggtggc | agtggcagtg | actcggagcc | tgacagccca | gtctttgagg | 1680 |
| acagcaaggc | aaagccagag | cagcggccgt | ctctgcacag | ccggggcatg | ctggaccgct | 1740 |
| cccgcctggc | cctgtgcacg | ctcgtcttcc | tctgcctgtc | ctgcaacccc | ttggcctcct | 1800 |
| tgctgggggc | ccgggggctt | cccagcccct | cagataccac | cagcgtctac | catagccctg | 1860 |
| ggcgcaacgt | gctgggcacc | gagagcagag | atggccctgg | ctgggcccag | tggctgctgc | 1920 |
| ccccagtggt | ctggctgctc | aatgggctgt | tggtgctcgt | ctccttggtg | cttctctttg | 1980 |
| tctacggtga | gccagtcaca | cggccccact | caggccccgc | cgtgtacttc | tggaggcatc | 2040 |
| gcaagcaggc | tgacctggac | ctggcccggg | gagactttgc | ccaggctgcc | cagcagctgt | 2100 |
| ggctggccct | gcgggcactg | ggccggcccc | tgcccacctc | ccacctggac | ctggcttgta | 2160 |
| gcctcctctg | gaacctcatc | cgtcacctgc | tgcagcgtct | ctgggtgggc | cgctggctgg | 2220 |
| caggccgggc | aggggggcctg | cagcaggact | gtgctctgcg | agtggatgct | agcgccagcg | 2280 |
| cccgagacgc | agccctggtc | taccataagc | tgcaccagct | gcacaccatg | gggaagcaca | 2340 |
| caggcgggca | cctcactgcc | accaacctgg | cgctgagtgc | cctgaacctg | gcagagtgtg | 2400 |
| caggggatgc | cgtgtctgtg | gcgacgctgg | ccgagatcta | tgtggcggct | gcattgagag | 2460 |
| tgaagaccag | tctcccacgg | gccttgcatt | ttctgacacg | cttcttcctg | agcagtgccc | 2520 |
| gccaggcctg | cctggcacag | agtggctcag | tgcctcctgc | catgcagtgg | ctctgccacc | 2580 |
| ccgtgggcca | ccgtttcttc | gtggatgggg | actggtccgt | gctcagtacc | ccatgggaga | 2640 |
| gcctgtacag | cttggccggg | aacccagtgg | acccctggc | ccaggtgact | cagctattcc | 2700 |
| gggaacatct | cttagagcga | gcactgaact | gtgtgaccca | gcccaacccc | agccctgggt | 2760 |
| cagctgatgg | ggacaaggaa | ttctcggatg | ccctcgggta | cctgcagctg | ctgaacagct | 2820 |
| gttctgatgc | tgcgggggct | cctgcctaca | gcttctccat | cagttccagc | atggccacca | 2880 |
| ccaccggcgt | agacccggtg | gccaagtggt | gggcctctct | gacagctgtg | gtgatccact | 2940 |
| ggctgcggcg | ggatgaggag | gcggctgagc | ggctgtgccc | gctggtggag | cacctgcccc | 3000 |
| gggtgctgca | ggagtctgag | agacccctgc | ccagggcagc | tctgcactcc | ttcaaggctg | 3060 |
| cccgggccct | gctgggctgt | gccaaggcag | agtctggtcc | agccagcctg | accatctgtg | 3120 |
| agaaggccag | tgggtacctg | caggacagcc | tggctaccac | accagccagc | agctccattg | 3180 |
| acaaggccgt | gcagctgttc | ctgtgtgacc | tgcttcttgt | ggtgcgcacc | agcctgtggc | 3240 |
| ggcagcagca | gcccccggcc | ccggccccag | cagcccaggg | caccagcagc | aggccccagg | 3300 |
| cttccgccct | tgagctgcgt | ggcttccaac | gggacctgag | cagcctgagg | cggctggcac | 3360 |
| agagcttccg | gccgccatg | cggagggtgt | tcctacatga | ggccacgcc | cggctgatgg | 3420 |
| cgggggccag | ccccacacgg | acacaccagc | tcctcgaccg | cagtctgagg | cggcgggcag | 3480 |
| gccccgtgg | caaaggaggc | gcggtggcg | agctggagcc | gcggcccacg | cggcgggagc | 3540 |
| acgcggaggc | cttgctgctg | gcctcctgct | acctgccccc | cggcttcctg | tcggcgcccg | 3600 |
| ggcagcgcgt | gggcatgctg | gctgaggcgg | cgcgcacact | cgagaagctt | ggcgatcgcc | 3660 |

```
ggctgctgca cgactgtcag cagatgctca tgcgcctggg cggtgggacc actgtcactt   3720
ccagctagac cccgtgtccc cggcctcagc acccctgtct ctagccactt tggtcccgtg   3780
cagcttctgt cctgcgtcga agctttgaag gccgaaggca gtgcaagaga ctctggcctc   3840
cacagttcga cctgcggctg ctgtgtgcct tcgcggtgga aggcccgagg ggcgcgatct   3900
tgaccctaag accggcggcc atgatggtgc tgacctctgg tggccgatcg gggcactgca   3960
ggggccgagc catttggggg ggcccccctc cttgctctgc aggcacctta gtggcttttt   4020
tcctcctgtg tacagggaag agaggggtac atttccctgt gctgacggaa gccaacttgg   4080
ctttcccgga ctgcaagcag ggctctgccc cagaggcctc tctctccgtc gtgggagaga   4140
gacgtgtaca tagtgtaggt cagcgtgctt agcctcctga cctgaggctc ctgtgctact   4200
ttgcctttg caaactttat tttcatagat tgagaagttt tgtacagaga attaaaaatg   4260
aaattattta taatctgggt tttgtgtctt cagctgatgg atgtgctgac tagtgagagt   4320
gcttgggccc tcccccagca cctagggaaa ggcttcccct ccccctccgg ccacaaggta   4380
cacaactttt aacttagctc ttcccgatgt ttgtttgtta gtgggaggag tggggagggc   4440
tggctgtatg gcctccagcc tacctgttcc ccctgctccc agggcacatg gttgggctgt   4500
gtcaacccttagggcctcca tggggtcagt tgtcccttct cacctcccag ctctgtcccc   4560
atcaggtccc tgggtggcac gggaggatgg actgacttcc aggacctgtt gtgtgacagg   4620
agctacagct tgggtctccc tgcaagaagt ctggcacgtc tcacctcccc catcccggcc   4680
cctggtcatc tcacagcaaa gaagcctcct ccctcccgac ctgccgccac actggagagg   4740
gggcacaggg gcggggagg tttcctgttc tgtgaaaggc cgactccctg actccattca   4800
tgccccccc cccagcccct cccttcattc ccattcccca acctaaagcc tggcccggct   4860
cccagctgaa tctggtcgga atccacgggc tgcagatttt ccaaaacaat cgttgtatct   4920
ttattgactt tttttttttt tttttctga atgcaatgac tgtttttttac tcttaaggaa   4980
aataaacatc ttttagaaac aaaaaaaaaa aa                                 5012
```

<210> SEQ ID NO 3
<211> LENGTH: 1147
<212> TYPE: PRT
<213> ORGANISM: Homo sapiens

<400> SEQUENCE: 3

```
Met Asp Glu Pro Pro Phe Ser Glu Ala Ala Leu Glu Gln Ala Leu Gly
1               5                   10                  15

Glu Pro Cys Asp Leu Asp Ala Ala Leu Leu Thr Asp Ile Glu Asp Met
            20                  25                  30

Leu Gln Leu Ile Asn Asn Gln Asp Ser Asp Phe Pro Gly Leu Phe Asp
        35                  40                  45

Pro Pro Tyr Ala Gly Ser Gly Ala Gly Gly Thr Asp Pro Ala Ser Pro
    50                  55                  60

Asp Thr Ser Ser Pro Gly Ser Leu Ser Pro Pro Ala Thr Leu Ser
65                  70                  75                  80

Ser Ser Leu Glu Ala Phe Leu Ser Gly Pro Gln Ala Ala Pro Ser Pro
                85                  90                  95

Leu Ser Pro Pro Gln Pro Ala Pro Thr Pro Leu Lys Met Tyr Pro Ser
            100                 105                 110

Met Pro Ala Phe Ser Pro Gly Pro Gly Ile Lys Glu Glu Ser Val Pro
        115                 120                 125
```

-continued

Leu Ser Ile Leu Gln Thr Pro Thr Pro Gln Pro Leu Pro Gly Ala Leu
130                 135                 140

Leu Pro Gln Ser Phe Pro Ala Pro Ala Pro Pro Gln Phe Ser Ser Thr
145                 150                 155                 160

Pro Val Leu Gly Tyr Pro Ser Pro Pro Gly Gly Phe Ser Thr Gly Ser
                165                 170                 175

Pro Pro Gly Asn Thr Gln Gln Pro Leu Pro Gly Leu Pro Leu Ala Ser
            180                 185                 190

Pro Pro Gly Val Pro Pro Val Ser Leu His Thr Gln Val Gln Ser Val
            195                 200                 205

Val Pro Gln Gln Leu Leu Thr Val Thr Ala Ala Pro Thr Ala Ala Pro
210                 215                 220

Val Thr Thr Thr Val Thr Ser Gln Ile Gln Gln Val Pro Val Leu Leu
225                 230                 235                 240

Gln Pro His Phe Ile Lys Ala Asp Ser Leu Leu Leu Thr Ala Met Lys
                245                 250                 255

Thr Asp Gly Ala Thr Val Lys Ala Ala Gly Leu Ser Pro Leu Val Ser
            260                 265                 270

Gly Thr Thr Val Gln Thr Gly Pro Leu Pro Thr Leu Val Ser Gly Gly
            275                 280                 285

Thr Ile Leu Ala Thr Val Pro Leu Val Val Asp Ala Glu Lys Leu Pro
290                 295                 300

Ile Asn Arg Leu Ala Ala Gly Ser Lys Ala Pro Ala Ser Ala Gln Ser
305                 310                 315                 320

Arg Gly Glu Lys Arg Thr Ala His Asn Ala Ile Glu Lys Arg Tyr Arg
                325                 330                 335

Ser Ser Ile Asn Asp Lys Ile Ile Glu Leu Lys Asp Leu Val Val Gly
            340                 345                 350

Thr Glu Ala Lys Leu Asn Lys Ser Ala Val Leu Arg Lys Ala Ile Asp
            355                 360                 365

Tyr Ile Arg Phe Leu Gln His Ser Asn Gln Lys Leu Lys Gln Glu Asn
370                 375                 380

Leu Ser Leu Arg Thr Ala Val His Lys Ser Lys Ser Leu Lys Asp Leu
385                 390                 395                 400

Val Ser Ala Cys Gly Ser Gly Gly Asn Thr Asp Val Leu Met Glu Gly
                405                 410                 415

Val Lys Thr Glu Val Glu Asp Thr Leu Thr Pro Pro Ser Asp Ala
            420                 425                 430

Gly Ser Pro Phe Gln Ser Ser Pro Leu Ser Leu Gly Ser Arg Gly Ser
            435                 440                 445

Gly Ser Gly Gly Ser Gly Ser Asp Ser Glu Pro Asp Ser Pro Val Phe
450                 455                 460

Glu Asp Ser Lys Ala Lys Pro Glu Gln Arg Pro Ser Leu His Ser Arg
465                 470                 475                 480

Gly Met Leu Asp Arg Ser Arg Leu Ala Leu Cys Thr Leu Val Phe Leu
                485                 490                 495

Cys Leu Ser Cys Asn Pro Leu Ala Ser Leu Leu Gly Ala Arg Gly Leu
            500                 505                 510

Pro Ser Pro Ser Asp Thr Thr Ser Val Tyr His Ser Pro Gly Arg Asn
            515                 520                 525

Val Leu Gly Thr Glu Ser Arg Asp Gly Pro Gly Trp Ala Gln Trp Leu
530                 535                 540

Leu Pro Pro Val Val Trp Leu Leu Asn Gly Leu Leu Val Leu Val Ser

```
                545                 550                 555                 560
            Leu Val Leu Leu Phe Val Tyr Gly Glu Pro Val Thr Arg Pro His Ser
                                565                 570                 575

Gly Pro Ala Val Tyr Phe Trp Arg His Arg Lys Gln Ala Asp Leu Asp
                                580                 585                 590

Leu Ala Arg Gly Asp Phe Ala Gln Ala Ala Gln Leu Trp Leu Ala
                                595                 600                 605

Leu Arg Ala Leu Gly Arg Pro Leu Pro Thr Ser His Leu Asp Leu Ala
                                610                 615                 620

Cys Ser Leu Leu Trp Asn Leu Ile Arg His Leu Leu Gln Arg Leu Trp
            625                 630                 635                 640

Val Gly Arg Trp Leu Ala Gly Arg Ala Gly Leu Gln Gln Asp Cys
                                645                 650                 655

Ala Leu Arg Val Asp Ala Ser Ala Ser Ala Arg Asp Ala Ala Leu Val
                                660                 665                 670

Tyr His Lys Leu His Gln Leu His Thr Met Gly Lys His Thr Gly Gly
                                675                 680                 685

His Leu Thr Ala Thr Asn Leu Ala Leu Ser Ala Leu Asn Leu Ala Glu
                                690                 695                 700

Cys Ala Gly Asp Ala Val Ser Val Ala Thr Leu Ala Glu Ile Tyr Val
            705                 710                 715                 720

Ala Ala Ala Leu Arg Val Lys Thr Ser Leu Pro Arg Ala Leu His Phe
                                725                 730                 735

Leu Thr Arg Phe Phe Leu Ser Ser Ala Arg Gln Ala Cys Leu Ala Gln
                                740                 745                 750

Ser Gly Ser Val Pro Pro Ala Met Gln Trp Leu Cys His Pro Val Gly
                                755                 760                 765

His Arg Phe Phe Val Asp Gly Asp Trp Ser Val Leu Ser Thr Pro Trp
                                770                 775                 780

Glu Ser Leu Tyr Ser Leu Ala Gly Asn Pro Val Asp Pro Leu Ala Gln
            785                 790                 795                 800

Val Thr Gln Leu Phe Arg Glu His Leu Leu Glu Arg Ala Leu Asn Cys
                                805                 810                 815

Val Thr Gln Pro Asn Pro Ser Pro Gly Ser Ala Asp Gly Asp Lys Glu
                                820                 825                 830

Phe Ser Asp Ala Leu Gly Tyr Leu Gln Leu Leu Asn Ser Cys Ser Asp
                                835                 840                 845

Ala Ala Gly Ala Pro Ala Tyr Ser Phe Ser Ile Ser Ser Ser Met Ala
                                850                 855                 860

Thr Thr Thr Gly Val Asp Pro Val Ala Lys Trp Trp Ala Ser Leu Thr
            865                 870                 875                 880

Ala Val Val Ile His Trp Leu Arg Arg Asp Glu Glu Ala Ala Glu Arg
                                885                 890                 895

Leu Cys Pro Leu Val Glu His Leu Pro Arg Val Leu Gln Glu Ser Glu
                                900                 905                 910

Arg Pro Leu Pro Arg Ala Ala Leu His Ser Phe Lys Ala Ala Arg Ala
                                915                 920                 925

Leu Leu Gly Cys Ala Lys Ala Glu Ser Gly Pro Ala Ser Leu Thr Ile
                                930                 935                 940

Cys Glu Lys Ala Ser Gly Tyr Leu Gln Asp Ser Leu Ala Thr Thr Pro
            945                 950                 955                 960

Ala Ser Ser Ser Ile Asp Lys Ala Val Gln Leu Phe Leu Cys Asp Leu
                                965                 970                 975
```

Leu Leu Val Val Arg Thr Ser Leu Trp Arg Gln Gln Pro Ala
            980                 985                 990

Pro Ala Pro Ala Ala Gln Gly Thr Ser Ser Arg Pro Gln Ala Ser Ala
        995                 1000                1005

Leu Glu Leu Arg Gly Phe Gln Arg Asp Leu Ser Ser Leu Arg Arg
    1010                1015                1020

Leu Ala Gln Ser Phe Arg Pro Ala Met Arg Arg Val Phe Leu His
    1025                1030                1035

Glu Ala Thr Ala Arg Leu Met Ala Gly Ala Ser Pro Thr Arg Thr
    1040                1045                1050

His Gln Leu Leu Asp Arg Ser Leu Arg Arg Ala Gly Pro Gly
    1055                1060                1065

Gly Lys Gly Gly Ala Val Ala Glu Leu Glu Pro Arg Pro Thr Arg
    1070                1075                1080

Arg Glu His Ala Glu Ala Leu Leu Leu Ala Ser Cys Tyr Leu Pro
    1085                1090                1095

Pro Gly Phe Leu Ser Ala Pro Gly Gln Arg Val Gly Met Leu Ala
    1100                1105                1110

Glu Ala Ala Arg Thr Leu Glu Lys Leu Gly Asp Arg Arg Leu Leu
    1115                1120                1125

His Asp Cys Gln Gln Met Leu Met Arg Leu Gly Gly Gly Thr Thr
    1130                1135                1140

Val Thr Ser Ser
    1145

<210> SEQ ID NO 4
<211> LENGTH: 4922
<212> TYPE: DNA
<213> ORGANISM: Homo sapiens

<400> SEQUENCE: 4
agcagagctg cggccggggg aacccagttt ccgaggaact tttcgccggc gccgggccgc    60
ctctgaggcc agggcaggac acgaacgcgc ggagcggcgg cggcgactga gagccggggc   120
cgcggcggcg ctccctagga agggccgtac gaggcggcgg gccggcggg cctcccggag   180
gaggcggctg cgccatggac gagccaccct tcagcgaggc ggctttggag caggcgctgg   240
gcgagccgtg cgatctggac gcggcgctgc tgaccgacat cgaagacatg cttcagctta   300
tcaacaacca agacagtgac ttccctggcc tatttgaccc accctatgct gggagtgggg   360
caggggggcac agaccctgcc agccccgata ccagctcccc aggcagcttg tctccacctc   420
ctgccacatt gagctcctct cttgaagcct tcctgagcgg ccgcaggca gcgccctcac   480
ccctgtcccc tccccagcct gcacccactc cattgaagat gtaccgtcc atgcccgctt   540
tctcccctgg gctggtatc aaggaagagt cagtgccact gagcatcctg cagacccca   600
ccccacagcc cctgccaggg gcctcctgc cacagagctt cccagcccca gccccaccgc   660
agttcagctc caccccctgtg ttaggctacc ccagccctcc gggaggcttc tctacaggaa   720
gccctcccgg gaacacccag cagccgctgc ctggcctgcc actggcttcc ccgcaggggg   780
tcccgcccgt ctccttgcac acccaggtcc agagtgtggt ccccccagcag ctactgacag   840
tcacagctgc ccccacggca gcccctgtaa cgaccactgt gacctcgcag atccagcagg   900
tcccggtcct gctgcagccc cacttcatca aggcagactc gctgcttctg acagccatga   960
agacagacgg agccactgtg aaggcggcag gtctcagtcc cctggtctct ggcaccactg  1020

```
tgcagacagg gcctttgccg accctggtga gtggcggaac catcttggca acagtccac      1080
tggtcgtaga tgcggagaag ctgcctatca accggctcgc agctggcagc aaggccccgg     1140
cctctgccca gagccgtgga gagaagcgca cagcccacaa cgccattgag aagcgctacc    1200
gctcctccat caatgacaaa atcattgagc tcaaggatct ggtggtgggc actgaggcaa    1260
agctgaataa atctgctgtc ttgcgcaagg ccatcgacta cattcgcttt ctgcaacaca    1320
gcaaccagaa actcaagcag gagaacctaa gtctgcgcac tgctgtccac aaaagcaaat    1380
ctctgaagga tctggtgtcg gcctgtggca gtggagggaa cacagacgtg ctcatggagg    1440
gcgtgaagac tgaggtggag gacacactga ccccacccccc ctcggatgct ggctcacctt    1500
tccagagcag ccccttgtcc cttggcagca ggggcagtgg cagcggtggc agtggcagtg    1560
actcggagcc tgacagccca gtctttgagg acagcaaggc aaagccagag cagcggccgt    1620
ctctgcacag ccggggcatg ctggaccgct cccgcctggc cctgtgcacg ctcgtcttcc    1680
tctgcctgtc ctgcaacccc ttggcctcct tgctgggggc cggggggctt cccagcccct    1740
cagataccac cagcgtctac catagccctg gcgcaacgt gctgggcacc gagagcagag    1800
atggccctgg ctgggcccag tggctgctgc ccccagtggt ctggctgctc aatgggctgt    1860
tggtgctcgt ctccttggtg cttctctttg tctacggtga ccagtcaca cggccccact    1920
caggccccgc cgtgtacttc tggaggcatc gcaagcaggc tgacctggac ctggcccggg    1980
gagactttgc ccaggctgcc cagcagctgt ggctggccct gcgggcactg ggccggcccc    2040
tgcccacctc ccacctggac ctggcttgta gcctcctctg gaacctcatc cgtcacctgc    2100
tgcagcgtct ctgggtgggc cgctggctgg caggccgggc aggggccctg cagcaggact    2160
gtgctctgcg agtggatgct agcgccagcg cccgagacgc agccctggtc taccataagc    2220
tgcaccagct gcacaccatg gggaagcaca caggcgggca cctcactgcc accaacctgg    2280
cgctgagtgc cctgaacctg gcagagtgtg caggggatgc cgtgtctgtg gcgacgctgg    2340
ccgagatcta tgtggcggct gcattgagag tgaagaccag tctcccacgg gccttgcatt    2400
ttctgacacg cttcttcctg agcagtgccc gccaggcctg cctggcacag agtggctcag    2460
tgcctcctgc catgcagtgg ctctgccacc ccgtgggcca ccgtttcttc gtggatgggg    2520
actggtccgt gctcagtacc ccatgggaga gcctgtacag cttggccggg aacccagtgg    2580
accccctggc ccaggtgact cagctattcc gggaacatct cttagagcga gcactgaact    2640
gtgtgaccca gcccaacccc agccctgggt cagctgatgg ggacaaggaa ttctcggatg    2700
ccctcgggta cctgcagctg ctgaacagct gttctgatgc tgcgggggct cctgcctaca    2760
gcttctccat cagttccagc atggccacca ccaccggcgt agacccggtg ccaagtggt    2820
gggcctctct gacagctgtg gtgatccact ggctgcggcg ggatgaggag gcggctgagc    2880
ggctgtgccc gctggtggag cacctgcccc gggtgctgca ggagtctgag agacccctgc    2940
ccagggcagc tctgcactcc ttcaaggctc ccgggccct gctgggctgt gccaaggcag    3000
agtctggtcc agccagcctg accatctgtg agaaggccag tgggtacctg caggacagcc    3060
tggctaccac accagccagc agctccattg acaaggccgt gcagctgttc ctgtgtgacc    3120
tgcttcttgt ggtgcgcacc agcctgtggc ggcagcagca gcccccggcc ccggcccag    3180
cagcccaggg caccagcagc aggccccagg cttccgccct tgagctgcgt ggcttccaac    3240
gggacctgag cagcctgagg cggctggcac agagcttccg gcccgccatg cggagggtgt    3300
tcctacatga ggccacggcc cggctgatgg cgggggccag cccacacgg acacaccagc    3360
tcctcgaccg cagtctgagg cggcgggcag gccccggtgg caaaggaggc gcggtggcgg    3420
```

```
agctggagcc gcggcccacg cggcgggagc acgcggaggc cttgctgctg gcctcctgct     3480
acctgccccc cggcttcctg tcggcgcccg ggcagcgcgt gggcatgctg gctgaggcgg     3540
cgcgcacact cgagaagctt ggcgatcgcc ggctgctgca cgactgtcag cagatgctca     3600
tgcgcctggg cggtgggacc actgtcactt ccagctagac cccgtgtccc cggcctcagc     3660
acccctgtct ctagccactt tggtcccgtg cagcttctgt cctgcgtcga agctttgaag     3720
gccgaaggca gtcaagaga ctctggcctc cacagttcga cctgcggctg ctgtgtgcct     3780
tcgcggtgga aggcccgagg ggcgcgatct tgaccctaag accggcggcc atgatggtgc     3840
tgacctctgg tggccgatcg gggcactgca ggggccgagc cattttgggg ggccccctc      3900
cttgctctgc aggcacctta gtggcttttt cctcctgtg tacagggaag agagggtac       3960
atttccctgt gctgacggaa gccaacttgg ctttcccgga ctgcaagcag gctctgccc      4020
cagaggcctc tctctccgtc gtgggagaga gacgtgtaca tagtgtaggt cagcgtgctt     4080
agcctcctga cctgaggctc ctgtgctact ttgccttttg caaactttat tttcatagat     4140
tgagaagttt tgtacagaga attaaaaatg aaattattta taatctgggt tttgtgtctt     4200
cagctgatgg atgtgctgac tagtgagagt gcttgggccc tcccccagca cctagggaaa     4260
ggcttcccct ccccctccgg ccacaaggta cacaactttt aacttagctc ttcccgatgt     4320
ttgtttgtta gtgggaggag tggggagggc tggctgtatg gcctccagcc tacctgttcc     4380
ccctgctccc agggcacatg gttgggctgt gtcaaccctt agggcctcca tggggtcagt     4440
tgtcccttct cacctcccag ctctgtcccc atcaggtccc tgggtggcac gggaggatgg     4500
actgacttcc aggacctgtt gtgtgacagg agctacagct gggtctccc tgcaagaagt       4560
ctggcacgtc tcacctcccc catcccggcc cctggtcatc tcacagcaaa gaagcctcct     4620
ccctcccgac ctgccgccac actggagagg gggcacaggg gcggggagg tttcctgttc      4680
tgtgaaaggc cgactccctg actccattca tgcccccccc cccagcccct cccttcattc     4740
ccattcccca acctaaagcc tggcccggct cccagctgaa tctggtcgga atccacgggc     4800
tgcagatttt ccaaaacaat cgttgtatct ttattgactt ttttttttt ttttttctga      4860
atgcaatgac tgttttttac tcttaaggaa aataaacatc ttttagaaac aaaaaaaaaa     4920
aa                                                                    4922
```

<210> SEQ ID NO 5
<211> LENGTH: 2169
<212> TYPE: DNA
<213> ORGANISM: Homo sapiens

<400> SEQUENCE: 5

```
ctcggtcttt aaaggaaga aggggcttat cgttaagtcg cttgtgatct tttcagtttc        60
tccagctgct ggcttttgg acacccactc ccccgccagg aggcagttgc aagcgcggag       120
gctgcgagaa ataactgcct cttgaaactt gcagggcgaa gagcaggcgg cgagcgctgg     180
gccggggagg gaccacccga gctgcgacgg gctctggggc tgcggggcag ggctggcgcc     240
cggagcctga gctgcaggag gtgcgctcgc tttcctcaac aggtggcggc ggggcgcgcg     300
ccgggagacc cccctaatg cgggaaaagc acgtgtccgc attttagaga aggcaaggcc       360
ggtgtgttta tctgcaagcc attatacttg cccacgaatc tttgagaaca ttataatgac     420
ctttgtgcct cttcttgcaa ggtgtttttct cagctgttat ctcaagacat ggatataaaa     480
aactcaccat ctagccttaa ttctccttcc tcctacaact gcagtcaatc catcttaccc     540
```

```
ctggagcacg gctccatata catacctccc tcctatgtag acagccacca tgaatatcca    600
gccatgacat tctatagccc tgctgtgatg aattacagca ttcccagcaa tgtcactaac    660
ttggaaggtg ggcctggtcg gcagaccaca agcccaaatg tgttgtggcc aacacctggg    720 caccttctc ctttagtggt ccatcgccag ttatcacatc tgtatgcgga acctcaaaag    780
agtccctggt gtgaagcaag atcgctagaa cacaccttac ctgtaaacag agagacactg    840
aaaaggaagg ttagtgggaa ccgttgcgcc agccctgtta ctggtccagg ttcaaagagg    900
gatgctcact tctgcgctgt ctgcagcgat tacgcatcgg gatatcacta tggagtctgg    960
tcgtgtgaag gatgtaaggc cttttttaaa agaagcattc aaggacataa tgattatatt   1020
tgtccagcta caaatcagtg tacaatcgat aaaaaccggc gcaagagctg ccaggcctgc   1080
cgacttcgga agtgttacga agtgggaatg tgaagtgtg ctcccggag agagagatgt     1140 gggtaccgcc ttgtgcggag acagagaagt gccgacgagc agctgcactg tgccggcaag   1200
gccaagagaa gtggcggcca cgcgccccga gtgcgggagc tgctgctgga cgccctgagc   1260
cccgagcagc tagtgctcac cctcctggag gctgagccgc ccatgtgct gatcagccgc    1320 cccagtgcgc ccttcaccga ggcctccatg atgatgtccc tgaccaagtt ggccgacaag   1380
gagttggtac acatgatcag ctgggccaag aagattcccg gctttgtgga gctcagcctg   1440
ttcgaccaag tgcggctctt ggagagctgt tggatggagg tgttaatgat ggggctgatg   1500
tggcgctcaa ttgaccaccc cggcaagctc atctttgctc cagatcttgt tctgaacgg   1560 gatgagggga aatgcgtaga aggaattctg gaaatctttg acatgctcct ggcaactact   1620
tcaaggtttc gagagttaaa actccaacac aaagaatatc tctgtgtcaa ggccatgatc   1680
ctgctcaatt ccagtatgta ccctctggtc acagcgaccc aggatgctga cagcagccgg   1740
aagctggctc acttgctgaa cgccgtgacc gatgctttgg tttgggtgat tgccaagagc   1800
ggcatctcct cccagcagca atccatgcgc ctggctaacc tcctgatgct cctgtcccac   1860
gtcaggcatg cgagtaacaa gggcatggaa catctgctca acatgaagtg caaaaatgtg   1920
gtcccagtgt atgacctgct gctggagatg ctgaatgccc acgtgcttcg cgggtgcaag   1980
tcctccatca cggggtccga gtgcagcccg gcagaggaca gtaaaagcaa agagggctcc   2040
cagaacccac agtctcagtg acgcctggcc ctgaggtgaa ctggcccaca gaggtcacag   2100
gctgaagcgt gaactccagt gtgtcaggag cctgggcttc atctttctgc tgtgtggtcc   2160
ctcatttgg                                                          2169
```

<210> SEQ ID NO 6
<211> LENGTH: 530
<212> TYPE: PRT
<213> ORGANISM: Homo sapiens

<400> SEQUENCE: 6

```
Met Asp Ile Lys Asn Ser Pro Ser Ser Leu Asn Ser Pro Ser Ser Tyr
1               5                   10                  15

Asn Cys Ser Gln Ser Ile Leu Pro Leu Glu His Gly Ser Ile Tyr Ile
            20                  25                  30

Pro Ser Ser Tyr Val Asp Ser His His Glu Tyr Pro Ala Met Thr Phe
        35                  40                  45

Tyr Ser Pro Ala Val Met Asn Tyr Ser Ile Pro Ser Asn Val Thr Asn
    50                  55                  60

Leu Glu Gly Gly Pro Gly Arg Gln Thr Thr Ser Pro Asn Val Leu Trp
65                  70                  75                  80
```

Pro Thr Pro Gly His Leu Ser Pro Leu Val His Arg Gln Leu Ser
                    85                  90                  95

His Leu Tyr Ala Glu Pro Gln Lys Ser Pro Trp Cys Glu Ala Arg Ser
            100                 105                 110

Leu Glu His Thr Leu Pro Val Asn Arg Glu Thr Leu Lys Arg Lys Val
            115                 120                 125

Ser Gly Asn Arg Cys Ala Ser Pro Val Thr Gly Pro Gly Ser Lys Arg
130                 135                 140

Asp Ala His Phe Cys Ala Val Cys Ser Asp Tyr Ala Ser Gly Tyr His
145                 150                 155                 160

Tyr Gly Val Trp Ser Cys Glu Gly Cys Lys Ala Phe Phe Lys Arg Ser
                165                 170                 175

Ile Gln Gly His Asn Asp Tyr Ile Cys Pro Ala Thr Asn Gln Cys Thr
            180                 185                 190

Ile Asp Lys Asn Arg Arg Lys Ser Cys Gln Ala Cys Arg Leu Arg Lys
            195                 200                 205

Cys Tyr Glu Val Gly Met Val Lys Cys Gly Ser Arg Arg Glu Arg Cys
210                 215                 220

Gly Tyr Arg Leu Val Arg Arg Gln Arg Ser Ala Asp Glu Gln Leu His
225                 230                 235                 240

Cys Ala Gly Lys Ala Lys Arg Ser Gly Gly His Ala Pro Arg Val Arg
                245                 250                 255

Glu Leu Leu Leu Asp Ala Leu Ser Pro Glu Gln Leu Val Leu Thr Leu
            260                 265                 270

Leu Glu Ala Glu Pro Pro His Val Leu Ile Ser Arg Pro Ser Ala Pro
            275                 280                 285

Phe Thr Glu Ala Ser Met Met Met Ser Leu Thr Lys Leu Ala Asp Lys
290                 295                 300

Glu Leu Val His Met Ile Ser Trp Ala Lys Lys Ile Pro Gly Phe Val
305                 310                 315                 320

Glu Leu Ser Leu Phe Asp Gln Val Arg Leu Leu Glu Ser Cys Trp Met
                325                 330                 335

Glu Val Leu Met Met Gly Leu Met Trp Arg Ser Ile Asp His Pro Gly
            340                 345                 350

Lys Leu Ile Phe Ala Pro Asp Leu Val Leu Asp Arg Asp Glu Gly Lys
            355                 360                 365

Cys Val Glu Gly Ile Leu Glu Ile Phe Asp Met Leu Leu Ala Thr Thr
370                 375                 380

Ser Arg Phe Arg Glu Leu Lys Leu Gln His Lys Glu Tyr Leu Cys Val
385                 390                 395                 400

Lys Ala Met Ile Leu Leu Asn Ser Ser Met Tyr Pro Leu Val Thr Ala
                405                 410                 415

Thr Gln Asp Ala Asp Ser Ser Arg Lys Leu Ala His Leu Leu Asn Ala
            420                 425                 430

Val Thr Asp Ala Leu Val Trp Val Ile Ala Lys Ser Gly Ile Ser Ser
            435                 440                 445

Gln Gln Gln Ser Met Arg Leu Ala Asn Leu Leu Met Leu Leu Ser His
450                 455                 460

Val Arg His Ala Ser Asn Lys Gly Met Glu His Leu Leu Asn Met Lys
465                 470                 475                 480

Cys Lys Asn Val Val Pro Val Tyr Asp Leu Leu Leu Glu Met Leu Asn
                485                 490                 495

Ala His Val Leu Arg Gly Cys Lys Ser Ser Ile Thr Gly Ser Glu Cys

```
            500             505             510
Ser Pro Ala Glu Asp Ser Lys Ser Lys Glu Gly Ser Gln Asn Pro Gln
        515                 520                 525

Ser Gln
    530

<210> SEQ ID NO 7
<211> LENGTH: 8481
<212> TYPE: DNA
<213> ORGANISM: Homo sapiens

<400> SEQUENCE: 7
gagagacggc agcggccccg gcctccctct ccgccgcgct tcagcctccc gctccgccgc      60
gctccagcct cgctctccgc cgcccgcacc gccgcccgcg ccctcaccag agcagccatg     120
gaggaggtgg tgattgccgg catgtccggg aagctgccag agtcggagaa cttgcaggag     180
ttctgggaca acctcatcgg cggtgtggac atggtcacgg acgatgaccg tcgctggaag     240
gcggggctct acgcctgccc ccggcggtcc ggcaagctga aggacctgtc taggtttgat     300
gcctccttct tcggagtcca ccccaagcag gcacacacga tggaccctca gctgcggctg     360
ctgctggaag tcacctatga agccatcgtg gacgaggca tcaacccaga ttcactccga     420
ggaacacaca ctggcgtctg ggtgggcgtg agcggctctg agacctcgga ggccctgagc     480
cgagaccccg agacactcgt gggctacagc atggtgggct gccagcgagc gatgatggcc     540
aaccggctct ccttcttctt cgacttcaga gggcccagca tcgcactgga cacagcctgc     600
tcctccagcc tgatggccct gcagaacgcc taccaggcca tccacagcgg gcagtgccct     660
gccgccatcg tgggggggcat caatgtcctg ctgaagccca cacctccgt gcagttcttg     720 aggctgggga tgctcagccc cgagggcacc tgcaaggcct tcgacacagc ggggaatggg     780
tactgccgct cggagggtgt ggtggccgtc ctgctgacca agaagtccct ggcccggcgg     840
gtgtacgcca ccatcctgaa cgccggcacc aatacagatg gcttcaagga gcaaggcgtg     900
accttcccct caggggatat ccaggagcag ctcatccgct cgttgtacca gtcggccgga     960
gtggcccctg agtcatttga atacatcgaa gcccacggca caggcaccaa ggtgggcgac    1020
ccccaggagc tgaatggcat caccccgagcc ctgtgcgcca cccgccagga gccgctgctc    1080
atcggctcca ccaagtccaa catggggcac ccggagccag cctcggggct ggcagccctg    1140
gccaaggtgc tgctgtccct ggagcacggg ctctgggccc caacctgca cttccatagc    1200 cccaaccctg agatcccagc gctgttggat gggcggctgc aggtggtgga ccagcccctg    1260
cccgtccgtg gcggcaacgt gggcatcaac tcctttggct tcggggctc caacgtgcac    1320 atcatcctga gcccaacac gcagccgccc ccgcacccg ccccacatgc caccctgccc    1380
cgtctgctgc gggccagcgg acgcacccct gaggccgtgc agaagctgct ggagcagggc    1440
ctccggcaca gccaggacct ggctttcctg agcatgctga acgacatcgc ggctgtcccc    1500
gccaccgcca tgcccttccg tggctacgct gtgctgggtg gtgagcgcgg tggcccagag    1560
gtgcagcagg tgcccgctgg cgagcgcccg ctctggttca tctgctctgg gatgggcaca    1620
cagtggcgcg ggatgggct gagcctcatg cgcctggacc gcttccgaga ttccatccta    1680
cgctccgatg aggctgtgaa gccattcggc ctgaaggtgt cacagctgct gctgagcaca    1740
gacgagagca cctttgatga catcgtccat tcgtttgtga gcctgactgc catccagata    1800
ggcctcatag acctgctgag ctgcatgggg ctgaggccag atggcatcgt cggccactcc    1860 ctggggggagg tggcctgtgg ctacgccgac ggctgcctgt cccaggagga ggccgtcctc    1920
```

```
gctgcctact ggaggggaca gtgcatcaaa gaagcccatc tcccgccggg cgccatggca    1980
gccgtgggct tgtcctggga ggagtgtaaa cagcgctgcc ccccgggcgt ggtgcccgcc    2040
tgccacaact ccaaggacac agtcaccatc tcgggacctc aggccccggt gtttgagttc    2100
gtggagcagc tgaggaagga gggtgtgttt gccaaggagg tgcggaccgg cggtatggcc    2160
ttccactcct acttcatgga ggccatcgca cccccactgc tgcaggagct caagaaggtg    2220
atccgggagc cgaagccacg ttcagcccgc tggctcagca cctctatccc cgaggcccag    2280
tggcacagca gcctggcacg cacgtcctcc gccgagtaca atgtcaacaa cctggtgagc    2340
cctgtgctgt tccaggaggc cctgtggcac gtgcctgagc acgcgtggt gctggagatc    2400
gcgcccacg ccctgctgca ggctgtcctg aagcgtggcc tgaagccgag ctgcaccatc    2460
atcccctga tgaagaagga tcacaggac aacctggagt tcttcctggc cggcatcggc    2520
aggctgcacc tctcaggcat cgacgccaac cccaatgcct tgttcccacc tgtggagttc    2580
ccagctcccc gaggaactcc cctcatctcc ccactcatca gtgggacca cagcctggcc    2640
tgggacgtgc cggccgccga ggacttcccc aacggttcag gttcccccctc agccgccatc    2700
tacaacatcg acaccagctc cgagtctcct gaccactacc tggtggacca cccctcgac    2760
ggtcgcgtcc tcttccccgc cactggctac ctgagcatag tgtggaagac gctggcccgc    2820
gccctgggcc tggcgtcga gcagctgcct gtggtgtttg aggatgtggt gctgcaccag    2880
gccaccatcc tgcccaagac tgggacagtg tccctggagg tacggctcct ggaggcctcc    2940
cgtgccttcg aggtgtcaga gaacggcaac ctggtagtga gtgggaaggt gtaccagtgg    3000
gatgaccctg accccaggct cttcgaccac ccggaaagcc caccccaa ccccacggag    3060
cccctcttcc tggcccaggc tgaagtttac aaggagctgc gtctgcgtgg ctacgactac    3120
ggccctcatt tccagggcat cctggaggcc agcctggaag gtgactcggg gaggctgctg    3180
tggaaggata actgggtgag cttcatggac accatgctgc agatgtccat cctgggctcg    3240
gccaagcacg gcctgtacct gcccacccgt gtcaccgcca tccacatcga ccctgccacc    3300
cacaggcaga agctgtacac actgcaggac aaggcccaag tggctgacgt ggtggtgagc    3360
aggtggctga gggtcacagt ggccggaggc gtccacatct ccgggctcca cactgagtcg    3420
gccccgcggc ggcagcagga gcagcaggtg cccatcctgg agaagttttg cttcactccc    3480
cacacggagg aggggtgcct gtctgagcgc gctgccctgc aggaggagct gcaactgtgc    3540
aaggggctgg tgcaggcact gcagaccaag gtgacccagc aggggctgaa gatggtggtg    3600
cccggactgg atggggccca gatccccgg gacccctcac agcaggaact gccccggctg    3660
ttgtcggctg cctgcaggct tcagctcaac gggaacctgc agctggagct ggcgcaggtg    3720
ctggcccagg agaggcccaa gctgccagag gaccctctgc tcagcggcct cctggactcc    3780
ccggcactca aggcctgcct ggacactgcc gtggagaaca tgcccagcct gaagatgaag    3840
gtggtggagg tgctggctgg ccacggtcac ctgtattccc gcatcccagg cctgctcagc    3900
cccatcccc tgctgcagct gagctacacg gccaccgacc gccaccccca ggccctggag    3960
gctgcccagg ccgagctgca gcagcacgac gttgcccagg gccagtggga tcccgcagac    4020
cctgcccca gcgccctggg cagcgccgac ctcctggtgt gcaactgtgc tgtggctgcc    4080
ctcggggacc cggcctcagc tctcagcaac atggtggctg ccctgagaga aggggcttt    4140
ctgctcctgc acacactgct ccggggcac cccctcgggg acatcgtggc cttcctcacc    4200
tccactgagc cgcagtatgg ccagggcatc ctgagccagg acgcgtggga gagcctcttc    4260
```

```
tccagggtgt cgctgcgcct ggtgggcctg aagaagtcct tctacggctc cacgctcttc    4320
ctgtgccgcc ggcccacccc gcaggacagc cccatcttcc tgccggtgga cgataccagc    4380
ttccgctggg tggagtctct gaagggcatc ctggctgacg aagactcttc ccggcctgtg    4440
tggctgaagg ccatcaactg tgccacctcg ggcgtggtgg gcttggtgaa ctgtctccgc    4500
cgagagcccg gcgggaaccg cctccggtgt gtgctgctct ccaacctcag cagcacctcc    4560
cacgtcccgg aggtggaccc gggctccgca gaactgcaga aggtgttgca gggagacctg    4620
gtgatgaacg tctaccgcga cggggcctgg ggggctttcc gccacttcct gctggaggag    4680
gacaagcctg aggagccgac ggcacatgcc tttgtgagca ccctcacccg gggggacctg    4740
tcctccatcc gctgggtctg ctcctcgctg cgccatgccc agcccacctg ccctggcgcc    4800
cagctctgca cggtctacta cgcctccctc aacttccgcg acatcatgct ggccactggc    4860
aagctgtccc ctgatgccat cccagggaag tggacctccc aggacagcct gctaggtatg    4920
gagttctcgg gccgagacgc cagcggcaag cgtgtgatgg gactggtgcc tgccaagggc    4980
ctggccacct ctgtcctgct gtcaccggac ttcctctggg atgtgccttc caactggacg    5040
ctggaggagg cggcctcggt gcctgtcgtc tacagcacgg cctactacgc gctggtggtg    5100
cgtgggcggg tgcgccccgg ggagacgctg ctcatccact cgggctcggg cggcgtgggc    5160
caggccgcca tcgccatcgc cctcagtctg ggctgccgcg tcttcaccac cgtggggtcg    5220
gctgagaagc gggcgtacct ccaggccagg ttcccccagc tcgacagcac cagcttcgcc    5280
aactcccggg acacatcctt cgagcagcat gtgctgtggc acacgggcgg aagggcgtt    5340
gacctggtct tgaactcctt ggcggaagag aagctgcagg ccagcgtgag gtgcttggct    5400
acgcacggtc gcttcctgga aattggcaaa ttcgacccttt ctcagaacca cccgctcggc    5460
atggctatct tcctgaagaa cgtgacattc acggggtcc tactgatgc gttcttcaac    5520
gagagcagtg ctgactggcg ggaggtgtgg gcgcttgtgc aggccggcat ccgggatggg    5580
gtggtacggc ccctcaagtg cacggtgttc catgggccc aggtggagga cgccttccgc    5640
tacatggccc aagggaagca cattggcaaa gtcgtcgtgc aggtgcttgc ggaggagccg    5700
gaggcagtgc tgaaggggc caaacccaag ctgatgtcgg ccatctccaa gacccttctgc    5760
ccggcccaca gagctacat catcgctggt ggtctgggtg gcttcggcct ggagttggcg    5820
cagtggctga tacagcgtgg ggtgcagaag ctcgtgttga cttctcgctc cgggatccgg    5880
acaggctacc aggccaagca ggtccgccgg tggaggcgcc agggcgtaca ggtgcaggtg    5940
tccaccagca catcagctc actggagggg gcccgggggcc tcattgccga gcggcgcag    6000
cttgggcccg tgggcggcgt cttcaacctg gccgtggtct tgagagatgg cttgctggag    6060
aaccagaccc cagagttctt ccaggacgtc tgcaagccca agtacagcgg caccctgaac    6120
ctggacaggg tgacccgaga ggcgtgccct gagctggact actttgtggt cttctcctct    6180
gtgagctgcg ggcgtggcaa tgcgggacag agcaactacg gctttgccaa ttccgccatg    6240
gagcgtatct gtgagaaacg ccggcacgaa ggcctcccag gcctggccgt gcagtggggc    6300
gccatcggcg acgtgggcat tttggtggag acgatgagca ccaacgacac gatcgtcagt    6360
ggcacgctgc cccagcgcat ggcgtcctgc ctggaggtgc tggacctctt cctgaaccag    6420
ccccacatgg tcctgagcag cttttgtctg gctgagaagg ctgcggccta tagggacagg    6480
gacagccagc gggacctggt ggaggccgtg cacacatcc tgggcatccg cgacttggct    6540
gctgtcaacc tggacagctc actggcggac ctggcctgg actcgctcat gagcgtggag    6600
gtgcgccaga cgctggagcg tgagctcaac ctggtgctgt ccgtgcgcga ggtgcggcaa    6660
```

```
ctcacgctcc ggaaactgca ggagctgtcc tcaaaggcgg atgaggccag cgagctggca    6720
tgccccacgc ccaaggagga tggtctggcc cagcagcaga ctcagctgaa cctgcgctcc    6780
ctgctggtga acccggaggg ccccacccty atgcggctca actccgtgca gagctcggag    6840
cggcccctgt tcctggtgca cccaatcgag ggctccacca ccgtgttcca cagcctggcc    6900
tcccggctca gcatccccac ctatggcctg cagtgcaccc gagctgcgcc ccttgacagc    6960
atccacagcc tggctgccta ctacatcgac tgcatcaggc aggtgcagcc cgagggcccc    7020
taccgcgtgg ccggctactc ctacggggcc tgcgtggcct ttgaaatgtg ctcccagctg    7080
cagccccagc agagcccagc ccccacccac aacagcctct tcctgttcga cggctcgccc    7140
acctacgtac tggcctacac ccagagctac cgggcaaagc tgaccccagg ctgtgaggct    7200
gaggctgaga cggaggccat atgcttcttc gtgcagcagt tcacggacat ggagcacaac    7260
agggtgctgg aggcgctgct gccgctgaag ggcctagagg agcgtgtggc agccgccgtg    7320
gacctgatca tcaagagcca ccagggcctg accgccagg agctgagctt tgcggccgg    7380 tccttctact acaagctgcg tgccgctgag cagtacacac ccaaggccaa gtaccatggc    7440
aacgtgatgc tactgcgcgc caagacgggt ggcgcctacg cgaggacct gggcgcggac    7500 tacaacctct cccaggtatg cgacgggaaa gtatccgtcc acgtcatcga gggtgaccac    7560
cgcacgctgc tggagggcag cggcctggag tccatcatca gcatcatcca cagctccctg    7620
gctgagccac gcgtgagcgt gcgggagggc taggcccgtg ccccgcctg ccaccggagg    7680 tcactccacc atccccaccc caccccaccc caccccgcc atgcaacggg attgaagggt    7740
cctgccggtg ggaccctgtc cggcccagtg ccactgcccc ccgaggctgc tagatgtagg    7800
tgttaggcat gtcccaccca cccgccgcct cccacggcac ctcggggaca ccagagctgc    7860
cgacttggag actcctggtc tgtgaagagc cggtggtgcc cgtgcccgca ggaactgggc    7920
tgggcctcgt gcgcccgtgg ggtctgcgct tggtctttct gtgcttggat ttgcatattt    7980
attgcattgc tggtagagac ccccaggcct gtccaccctg ccaagactcc tcaggcagcg    8040
tgtgggtccc gcactctgcc cccatttccc cgatgtcccc tgcgggcgcg ggcagccacc    8100
caagcctgct ggctgcggcc ccctctcggc caggcattgg ctcagcccgc tgagtggggg    8160
gtcgtgggcc agtccccgag gagctgggcc cctgcacagg cacacaggc ccggccacac    8220 ccagcggccc cccgcacagc cacccgtggg gtgctgccct tatgcccggc gccgggcacc    8280
aactccatgt ttggtgtttg tctgtgtttg tttttcaaga aatgattcaa attgctgctt    8340
ggattttgaa atttactgta actgtcagtg tacacgtctg gaccccgttt cattttaca    8400 ccaatttggt aaaaatgctg ctctcagcct cccacaatta aaccgcatgt gatctccaaa    8460
aaaaaaaaaa aaaaaaaaaa a                                              8481
```

<210> SEQ ID NO 8
<211> LENGTH: 2511
<212> TYPE: PRT
<213> ORGANISM: Homo sapiens

<400> SEQUENCE: 8

Met Glu Glu Val Val Ile Ala Gly Met Ser Gly Lys Leu Pro Glu Ser
1               5                   10                  15

Glu Asn Leu Gln Glu Phe Trp Asp Asn Leu Ile Gly Gly Val Asp Met
                20                  25                  30

Val Thr Asp Asp Asp Arg Arg Trp Lys Ala Gly Leu Tyr Gly Leu Pro
            35                  40                  45

```
Arg Arg Ser Gly Lys Leu Lys Asp Leu Ser Arg Phe Asp Ala Ser Phe
         50                  55                  60

Phe Gly Val His Pro Lys Gln Ala His Thr Met Asp Pro Gln Leu Arg
 65              70                  75                      80

Leu Leu Leu Glu Val Thr Tyr Glu Ala Ile Val Asp Gly Gly Ile Asn
                 85                  90                  95

Pro Asp Ser Leu Arg Gly Thr His Thr Gly Val Trp Val Gly Val Ser
             100                 105                 110

Gly Ser Glu Thr Ser Glu Ala Leu Ser Arg Asp Pro Glu Thr Leu Val
         115                 120                 125

Gly Tyr Ser Met Val Gly Cys Gln Arg Ala Met Met Ala Asn Arg Leu
         130                 135                 140

Ser Phe Phe Phe Asp Phe Arg Gly Pro Ser Ile Ala Leu Asp Thr Ala
145             150                 155                     160

Cys Ser Ser Ser Leu Met Ala Leu Gln Asn Ala Tyr Gln Ala Ile His
             165                 170                 175

Ser Gly Gln Cys Pro Ala Ala Ile Val Gly Gly Ile Asn Val Leu Leu
             180                 185                 190

Lys Pro Asn Thr Ser Val Gln Phe Leu Arg Leu Gly Met Leu Ser Pro
             195                 200                 205

Glu Gly Thr Cys Lys Ala Phe Asp Thr Ala Gly Asn Gly Tyr Cys Arg
             210                 215                 220

Ser Glu Gly Val Val Ala Val Leu Leu Thr Lys Lys Ser Leu Ala Arg
225             230                 235                     240

Arg Val Tyr Ala Thr Ile Leu Asn Ala Gly Thr Asn Thr Asp Gly Phe
                 245                 250                 255

Lys Glu Gln Gly Val Thr Phe Pro Ser Gly Asp Ile Gln Glu Gln Leu
             260                 265                 270

Ile Arg Ser Leu Tyr Gln Ser Ala Gly Val Ala Pro Glu Ser Phe Glu
         275                 280                 285

Tyr Ile Glu Ala His Gly Thr Gly Thr Lys Val Gly Asp Pro Gln Glu
         290                 295                 300

Leu Asn Gly Ile Thr Arg Ala Leu Cys Ala Thr Arg Gln Glu Pro Leu
305             310                 315                     320

Leu Ile Gly Ser Thr Lys Ser Asn Met Gly His Pro Glu Pro Ala Ser
             325                 330                 335

Gly Leu Ala Ala Leu Ala Lys Val Leu Leu Ser Leu Glu His Gly Leu
             340                 345                 350

Trp Ala Pro Asn Leu His Phe His Ser Pro Asn Pro Glu Ile Pro Ala
             355                 360                 365

Leu Leu Asp Gly Arg Leu Gln Val Val Asp Gln Pro Leu Pro Val Arg
370             375                 380

Gly Gly Asn Val Gly Ile Asn Ser Phe Gly Phe Gly Gly Ser Asn Val
385             390                 395                     400

His Ile Ile Leu Arg Pro Asn Thr Gln Pro Pro Ala Pro Ala Pro
             405                 410                 415

His Ala Thr Leu Pro Arg Leu Leu Arg Ala Ser Gly Arg Thr Pro Glu
             420                 425                 430

Ala Val Gln Lys Leu Leu Glu Gln Gly Leu Arg His Ser Gln Asp Leu
         435                 440                 445

Ala Phe Leu Ser Met Leu Asn Asp Ile Ala Ala Val Pro Ala Thr Ala
450             455                 460
```

```
Met Pro Phe Arg Gly Tyr Ala Val Leu Gly Glu Arg Gly Gly Pro
465                 470                 475                 480

Glu Val Gln Gln Val Pro Ala Gly Glu Arg Pro Leu Trp Phe Ile Cys
            485                 490                 495

Ser Gly Met Gly Thr Gln Trp Arg Gly Met Gly Leu Ser Leu Met Arg
            500                 505                 510

Leu Asp Arg Phe Arg Asp Ser Ile Leu Arg Ser Asp Glu Ala Val Lys
            515                 520                 525

Pro Phe Gly Leu Lys Val Ser Gln Leu Leu Leu Ser Thr Asp Glu Ser
            530                 535                 540

Thr Phe Asp Asp Ile Val His Ser Phe Val Ser Leu Thr Ala Ile Gln
545                 550                 555                 560

Ile Gly Leu Ile Asp Leu Leu Ser Cys Met Gly Leu Arg Pro Asp Gly
                565                 570                 575

Ile Val Gly His Ser Leu Gly Glu Val Ala Cys Gly Tyr Ala Asp Gly
                580                 585                 590

Cys Leu Ser Gln Glu Glu Ala Val Leu Ala Ala Tyr Trp Arg Gly Gln
    595                 600                 605

Cys Ile Lys Glu Ala His Leu Pro Pro Gly Ala Met Ala Ala Val Gly
    610                 615                 620

Leu Ser Trp Glu Glu Cys Lys Gln Arg Cys Pro Pro Gly Val Val Pro
625                 630                 635                 640

Ala Cys His Asn Ser Lys Asp Thr Val Thr Ile Ser Gly Pro Gln Ala
                645                 650                 655

Pro Val Phe Glu Phe Val Glu Gln Leu Arg Lys Glu Gly Val Phe Ala
                660                 665                 670

Lys Glu Val Arg Thr Gly Gly Met Ala Phe His Ser Tyr Phe Met Glu
                675                 680                 685

Ala Ile Ala Pro Pro Leu Leu Gln Glu Leu Lys Lys Val Ile Arg Glu
    690                 695                 700

Pro Lys Pro Arg Ser Ala Arg Trp Leu Ser Thr Ser Ile Pro Glu Ala
705                 710                 715                 720

Gln Trp His Ser Ser Leu Ala Arg Thr Ser Ser Ala Glu Tyr Asn Val
                725                 730                 735

Asn Asn Leu Val Ser Pro Val Leu Phe Gln Glu Ala Leu Trp His Val
                740                 745                 750

Pro Glu His Ala Val Val Leu Glu Ile Ala Pro His Ala Leu Leu Gln
            755                 760                 765

Ala Val Leu Lys Arg Gly Leu Lys Pro Ser Cys Thr Ile Ile Pro Leu
770                 775                 780

Met Lys Lys Asp His Arg Asp Asn Leu Glu Phe Phe Leu Ala Gly Ile
785                 790                 795                 800

Gly Arg Leu His Leu Ser Gly Ile Asp Ala Asn Pro Asn Ala Leu Phe
                805                 810                 815

Pro Pro Val Glu Phe Pro Ala Pro Arg Gly Thr Pro Leu Ile Ser Pro
            820                 825                 830

Leu Ile Lys Trp Asp His Ser Leu Ala Trp Asp Val Pro Ala Ala Glu
            835                 840                 845

Asp Phe Pro Asn Gly Ser Gly Ser Pro Ser Ala Ala Ile Tyr Asn Ile
            850                 855                 860

Asp Thr Ser Ser Glu Ser Pro Asp His Tyr Leu Val Asp His Thr Leu
865                 870                 875                 880

Asp Gly Arg Val Leu Phe Pro Ala Thr Gly Tyr Leu Ser Ile Val Trp
```

-continued

```
                885                 890                 895
Lys Thr Leu Ala Arg Ala Leu Gly Leu Gly Val Glu Gln Leu Pro Val
                900                 905                 910

Val Phe Glu Asp Val Val Leu His Gln Ala Thr Ile Leu Pro Lys Thr
                915                 920                 925

Gly Thr Val Ser Leu Glu Val Arg Leu Leu Glu Ala Ser Arg Ala Phe
            930                 935                 940

Glu Val Ser Glu Asn Gly Asn Leu Val Val Ser Gly Lys Val Tyr Gln
945                 950                 955                 960

Trp Asp Asp Pro Asp Pro Arg Leu Phe Asp His Pro Glu Ser Pro Thr
                965                 970                 975

Pro Asn Pro Thr Glu Pro Leu Phe Leu Ala Gln Ala Glu Val Tyr Lys
            980                 985                 990

Glu Leu Arg Leu Arg Gly Tyr Asp Tyr Gly Pro His Phe Gln Gly Ile
            995                1000                1005

Leu Glu Ala Ser Leu Glu Gly Asp Ser Gly Arg Leu Leu Trp Lys
      1010                1015                1020

Asp Asn Trp Val Ser Phe Met Asp Thr Met Leu Gln Met Ser Ile
      1025                1030                1035

Leu Gly Ser Ala Lys His Gly Leu Tyr Leu Pro Thr Arg Val Thr
      1040                1045                1050

Ala Ile His Ile Asp Pro Ala Thr His Arg Gln Lys Leu Tyr Thr
      1055                1060                1065

Leu Gln Asp Lys Ala Gln Val Ala Asp Val Val Ser Arg Trp
      1070                1075                1080

Leu Arg Val Thr Val Ala Gly Gly Val His Ile Ser Gly Leu His
      1085                1090                1095

Thr Glu Ser Ala Pro Arg Arg Gln Gln Glu Gln Gln Val Pro Ile
      1100                1105                1110

Leu Glu Lys Phe Cys Phe Thr Pro His Thr Glu Glu Gly Cys Leu
      1115                1120                1125

Ser Glu Arg Ala Ala Leu Gln Glu Glu Leu Gln Leu Cys Lys Gly
      1130                1135                1140

Leu Val Gln Ala Leu Gln Thr Lys Val Thr Gln Gln Gly Leu Lys
      1145                1150                1155

Met Val Val Pro Gly Leu Asp Gly Ala Gln Ile Pro Arg Asp Pro
      1160                1165                1170

Ser Gln Gln Glu Leu Pro Arg Leu Leu Ser Ala Ala Cys Arg Leu
      1175                1180                1185

Gln Leu Asn Gly Asn Leu Gln Leu Glu Leu Ala Gln Val Leu Ala
      1190                1195                1200

Gln Glu Arg Pro Lys Leu Pro Glu Asp Pro Leu Leu Ser Gly Leu
      1205                1210                1215

Leu Asp Ser Pro Ala Leu Lys Ala Cys Leu Asp Thr Ala Val Glu
      1220                1225                1230

Asn Met Pro Ser Leu Lys Met Lys Val Val Glu Val Leu Ala Gly
      1235                1240                1245

His Gly His Leu Tyr Ser Arg Ile Pro Gly Leu Leu Ser Pro His
      1250                1255                1260

Pro Leu Leu Gln Leu Ser Tyr Thr Ala Thr Asp Arg His Pro Gln
      1265                1270                1275

Ala Leu Glu Ala Ala Gln Ala Glu Leu Gln Gln His Asp Val Ala
      1280                1285                1290
```

```
Gln Gly Gln Trp Asp Pro Ala Asp Pro Ala Pro Ser Ala Leu Gly
    1295                1300                1305

Ser Ala Asp Leu Leu Val Cys Asn Cys Ala Val Ala Ala Leu Gly
    1310                1315                1320

Asp Pro Ala Ser Ala Leu Ser Asn Met Val Ala Ala Leu Arg Glu
    1325                1330                1335

Gly Gly Phe Leu Leu Leu His Thr Leu Leu Arg Gly His Pro Leu
    1340                1345                1350

Gly Asp Ile Val Ala Phe Leu Thr Ser Thr Glu Pro Gln Tyr Gly
    1355                1360                1365

Gln Gly Ile Leu Ser Gln Asp Ala Trp Glu Ser Leu Phe Ser Arg
    1370                1375                1380

Val Ser Leu Arg Leu Val Gly Leu Lys Lys Ser Phe Tyr Gly Ser
    1385                1390                1395

Thr Leu Phe Leu Cys Arg Arg Pro Thr Pro Gln Asp Ser Pro Ile
    1400                1405                1410

Phe Leu Pro Val Asp Asp Thr Ser Phe Arg Trp Val Glu Ser Leu
    1415                1420                1425

Lys Gly Ile Leu Ala Asp Glu Asp Ser Ser Arg Pro Val Trp Leu
    1430                1435                1440

Lys Ala Ile Asn Cys Ala Thr Ser Gly Val Val Gly Leu Val Asn
    1445                1450                1455

Cys Leu Arg Arg Glu Pro Gly Gly Asn Arg Leu Arg Cys Val Leu
    1460                1465                1470

Leu Ser Asn Leu Ser Ser Thr Ser His Val Pro Glu Val Asp Pro
    1475                1480                1485

Gly Ser Ala Glu Leu Gln Lys Val Leu Gln Gly Asp Leu Val Met
    1490                1495                1500

Asn Val Tyr Arg Asp Gly Ala Trp Gly Ala Phe Arg His Phe Leu
    1505                1510                1515

Leu Glu Glu Asp Lys Pro Glu Glu Pro Thr Ala His Ala Phe Val
    1520                1525                1530

Ser Thr Leu Thr Arg Gly Asp Leu Ser Ser Ile Arg Trp Val Cys
    1535                1540                1545

Ser Ser Leu Arg His Ala Gln Pro Thr Cys Pro Gly Ala Gln Leu
    1550                1555                1560

Cys Thr Val Tyr Tyr Ala Ser Leu Asn Phe Arg Asp Ile Met Leu
    1565                1570                1575

Ala Thr Gly Lys Leu Ser Pro Asp Ala Ile Pro Gly Lys Trp Thr
    1580                1585                1590

Ser Gln Asp Ser Leu Leu Gly Met Glu Phe Ser Gly Arg Asp Ala
    1595                1600                1605

Ser Gly Lys Arg Val Met Gly Leu Val Pro Ala Lys Gly Leu Ala
    1610                1615                1620

Thr Ser Val Leu Leu Ser Pro Asp Phe Leu Trp Asp Val Pro Ser
    1625                1630                1635

Asn Trp Thr Leu Glu Glu Ala Ala Ser Val Pro Val Val Tyr Ser
    1640                1645                1650

Thr Ala Tyr Tyr Ala Leu Val Val Arg Gly Arg Val Arg Pro Gly
    1655                1660                1665

Glu Thr Leu Leu Ile His Ser Gly Ser Gly Gly Val Gly Gln Ala
    1670                1675                1680
```

-continued

Ala Ile Ala Ile Ala Leu Ser Leu Gly Cys Arg Val Phe Thr Thr
1685                1690                1695

Val Gly Ser Ala Glu Lys Arg Ala Tyr Leu Gln Ala Arg Phe Pro
1700                1705                1710

Gln Leu Asp Ser Thr Ser Phe Ala Asn Ser Arg Asp Thr Ser Phe
1715                1720                1725

Glu Gln His Val Leu Trp His Thr Gly Gly Lys Gly Val Asp Leu
1730                1735                1740

Val Leu Asn Ser Leu Ala Glu Glu Lys Leu Gln Ala Ser Val Arg
1745                1750                1755

Cys Leu Ala Thr His Gly Arg Phe Leu Glu Ile Gly Lys Phe Asp
1760                1765                1770

Leu Ser Gln Asn His Pro Leu Gly Met Ala Ile Phe Leu Lys Asn
1775                1780                1785

Val Thr Phe His Gly Val Leu Leu Asp Ala Phe Phe Asn Glu Ser
1790                1795                1800

Ser Ala Asp Trp Arg Glu Val Trp Ala Leu Val Gln Ala Gly Ile
1805                1810                1815

Arg Asp Gly Val Val Arg Pro Leu Lys Cys Thr Val Phe His Gly
1820                1825                1830

Ala Gln Val Glu Asp Ala Phe Arg Tyr Met Ala Gln Gly Lys His
1835                1840                1845

Ile Gly Lys Val Val Val Gln Val Leu Ala Glu Glu Pro Glu Ala
1850                1855                1860

Val Leu Lys Gly Ala Lys Pro Lys Leu Met Ser Ala Ile Ser Lys
1865                1870                1875

Thr Phe Cys Pro Ala His Lys Ser Tyr Ile Ile Ala Gly Gly Leu
1880                1885                1890

Gly Gly Phe Gly Leu Glu Leu Ala Gln Trp Leu Ile Gln Arg Gly
1895                1900                1905

Val Gln Lys Leu Val Leu Thr Ser Arg Ser Gly Ile Arg Thr Gly
1910                1915                1920

Tyr Gln Ala Lys Gln Val Arg Arg Trp Arg Arg Gln Gly Val Gln
1925                1930                1935

Val Gln Val Ser Thr Ser Asn Ile Ser Ser Leu Glu Gly Ala Arg
1940                1945                1950

Gly Leu Ile Ala Glu Ala Ala Gln Leu Gly Pro Val Gly Gly Val
1955                1960                1965

Phe Asn Leu Ala Val Val Leu Arg Asp Gly Leu Leu Glu Asn Gln
1970                1975                1980

Thr Pro Glu Phe Phe Gln Asp Val Cys Lys Pro Lys Tyr Ser Gly
1985                1990                1995

Thr Leu Asn Leu Asp Arg Val Thr Arg Glu Ala Cys Pro Glu Leu
2000                2005                2010

Asp Tyr Phe Val Val Phe Ser Ser Val Ser Cys Gly Arg Gly Asn
2015                2020                2025

Ala Gly Gln Ser Asn Tyr Gly Phe Ala Asn Ser Ala Met Glu Arg
2030                2035                2040

Ile Cys Glu Lys Arg Arg His Glu Gly Leu Pro Gly Leu Ala Val
2045                2050                2055

Gln Trp Gly Ala Ile Gly Asp Val Gly Ile Leu Val Glu Thr Met
2060                2065                2070

Ser Thr Asn Asp Thr Ile Val Ser Gly Thr Leu Pro Gln Arg Met

```
                 2075                2080                2085
Ala Ser Cys Leu Glu Val Leu Asp Leu Phe Leu Asn Gln Pro His
    2090                2095                2100

Met Val Leu Ser Ser Phe Val Leu Ala Glu Lys Ala Ala Ala Tyr
    2105                2110                2115

Arg Asp Arg Asp Ser Gln Arg Asp Leu Val Glu Ala Val Ala His
    2120                2125                2130

Ile Leu Gly Ile Arg Asp Leu Ala Ala Val Asn Leu Asp Ser Ser
    2135                2140                2145

Leu Ala Asp Leu Gly Leu Asp Ser Leu Met Ser Val Glu Val Arg
    2150                2155                2160

Gln Thr Leu Glu Arg Glu Leu Asn Leu Val Leu Ser Val Arg Glu
    2165                2170                2175

Val Arg Gln Leu Thr Leu Arg Lys Leu Gln Glu Leu Ser Ser Lys
    2180                2185                2190

Ala Asp Glu Ala Ser Glu Leu Ala Cys Pro Thr Pro Lys Glu Asp
    2195                2200                2205

Gly Leu Ala Gln Gln Gln Thr Gln Leu Asn Leu Arg Ser Leu Leu
    2210                2215                2220

Val Asn Pro Glu Gly Pro Thr Leu Met Arg Leu Asn Ser Val Gln
    2225                2230                2235

Ser Ser Glu Arg Pro Leu Phe Leu Val His Pro Ile Glu Gly Ser
    2240                2245                2250

Thr Thr Val Phe His Ser Leu Ala Ser Arg Leu Ser Ile Pro Thr
    2255                2260                2265

Tyr Gly Leu Gln Cys Thr Arg Ala Ala Pro Leu Asp Ser Ile His
    2270                2275                2280

Ser Leu Ala Ala Tyr Tyr Ile Asp Cys Ile Arg Gln Val Gln Pro
    2285                2290                2295

Glu Gly Pro Tyr Arg Val Ala Gly Tyr Ser Tyr Gly Ala Cys Val
    2300                2305                2310

Ala Phe Glu Met Cys Ser Gln Leu Gln Ala Gln Gln Ser Pro Ala
    2315                2320                2325

Pro Thr His Asn Ser Leu Phe Leu Phe Asp Gly Ser Pro Thr Tyr
    2330                2335                2340

Val Leu Ala Tyr Thr Gln Ser Tyr Arg Ala Lys Leu Thr Pro Gly
    2345                2350                2355

Cys Glu Ala Glu Ala Glu Thr Glu Ala Ile Cys Phe Phe Val Gln
    2360                2365                2370

Gln Phe Thr Asp Met Glu His Asn Arg Val Leu Glu Ala Leu Leu
    2375                2380                2385

Pro Leu Lys Gly Leu Glu Glu Arg Val Ala Ala Ala Val Asp Leu
    2390                2395                2400

Ile Ile Lys Ser His Gln Gly Leu Asp Arg Gln Glu Leu Ser Phe
    2405                2410                2415

Ala Ala Arg Ser Phe Tyr Tyr Lys Leu Arg Ala Ala Glu Gln Tyr
    2420                2425                2430

Thr Pro Lys Ala Lys Tyr His Gly Asn Val Met Leu Leu Arg Ala
    2435                2440                2445

Lys Thr Gly Gly Ala Tyr Gly Glu Asp Leu Gly Ala Asp Tyr Asn
    2450                2455                2460

Leu Ser Gln Val Cys Asp Gly Lys Val Ser Val His Val Ile Glu
    2465                2470                2475
```

Gly Asp His Arg Thr Leu Leu Glu Gly Ser Gly Leu Glu Ser Ile
    2480                2485                2490

Ile Ser Ile Ile His Ser Ser Leu Ala Glu Pro Arg Val Ser Val
    2495                2500                2505

Arg Glu Gly
    2510

<210> SEQ ID NO 9
<211> LENGTH: 5473
<212> TYPE: DNA
<213> ORGANISM: Homo sapiens

<400> SEQUENCE: 9

```
ggcaggacga ggtggcacca aattcccttc ggccaatgac gagccggagt ttacagaagc      60
ctcattagca tttccccaga ggcaggggca ggggcagagg ccgggtggtg tggtgtcggt     120
gtcggcagca tccccggcgc cctgctgcgg tcgccgcgag cctcggcctc tgtctcctcc     180
ccctcccgcc cttacctcca cgcggaccg cccgcgccag tcaactcctc gcactttgcc     240
cctgcttggc agcggataaa aggggctga ggaaataccg acacggtca cccgttgcca     300
gctctagcct ttaaattccc ggctcgggga cctccacgca ccgcggctag cgccgacaac     360
cagctagcgt gcaaggcgcc gcggctcagc gcgtaccggc gggcttcgaa accgcagtcc     420
tccggcgacc ccgaactccg ctccggagcc tcagcccct ggaaagtgat cccggcatcc     480
gagagccaag atgccggccc acttgctgca ggacgatatc tctagctcct ataccaccac     540
caccaccatt cagcgcctc cctccagggt cctgcagaat ggaggagata gttggagac     600
gatgcccctc tacttggaag acgacattcg ccctgatata aagatgata tatgaccc     660
cacctacaag gataaggaag gcccaagccc caaggttgaa tatgtctgga aaacatcat     720
ccttatgtct ctgctacact tgggagccct gtatgggatc actttgattc ctacctgcaa     780
gttctacacc tggctttggg gggtattcta ctattttgtc agtgccctgg cataacagc     840
aggagctcat cgtctgtgga gccaccgctc ttacaaagct cggctgcccc tacggctctt     900
tctgatcatt gccaacacaa tggcattcca gaatgatgtc tatgaatggg ctcgtgacca     960
ccgtgcccac acaagttttt cagaaacaca tgctgatcct cataattccc gacgtggctt    1020
tttcttctct cacgtgggtt ggctgcttgt gcgcaaacac ccagctgtca agagaagggg    1080
gagtacgcta gacttgtctg acctagaagc tgagaaactg gtgatgttcc agaggaggta    1140
ctacaaacct ggcttgctga tgatgtgctt catcctgccc acgcttgtgc ctggtatt    1200
ctggggtgaa acttttcaaa acagtgtgtt cgttgccact tcttgcgat atgctgtggt    1260
gcttaatgcc acctggctgg tgaacagtgc tgcccacctc ttcggatatc gtccttatga    1320
caagaacatt agccccgggg agaatatcct ggtttcactt ggagctgtgg gtgagggctt    1380
ccacaactac caccactcct ttccctatga ctactctgcc agtgagtacc gctggcacat    1440
caacttcacc acattcttca ttgattgcat ggccgccctc ggtctggcct atgaccggaa    1500
gaaagtctcc aaggccgcca tcttggccag gattaaaaga accggagatg aaactacaa    1560
gagtggctga gttggggtc cctcaggttc cttttcaaa aaccagccag gcagaggttt    1620
taatgtctgt ttattaacta ctgaataatg ctaccaggat gctaaagatg atgatgttaa    1680
cccattccag tacagtattc ttttaaaatt caaaagtatt gaaagccaac aactctgcct    1740
ttatgatgct aagctgatat tatttcttct cttatcctct ctctcttcta ggcccattgt    1800
cctcctttc actttattgc tatcgccctc ctttcccta ttgcctccca ggcaagcagc    1860
```

```
tggtcagtct tgctcagtg tccagcttcc aaagcctaga caacctttct gtagcctaaa    1920
acgaatggtc tttgctccag ataactctct ttccttgagc tgttgtgagc tttgaagtag    1980
gtggcttgag ctagagataa aacagaatct tctgggtagt ccccctgttga ttatcttcag   2040 cccaggcttt tgctagatgg aatggaaaag caacttcatt tgacacaaag cttctaaagc    2100
aggtaaattg tcgggggaga gagttagcat gtatgaatgt aaggatgagg gaagcgaagc    2160
aagaggaacc tctcgccatg atcagacata cagctgccta cctaatgagg acttcaagcc    2220
ccaccacata gcatgcttcc tttctctcct ggctcggggt aaaaagtggc tgcggtgttt    2280
ggcaatgcta attcaatgcc gcaacatata gttgaggccg aggataaaga aaagacattt    2340
taagtttgta gtaaaagtgg tctctgctgg ggaagggttt tcttttcttt ttttctttaa    2400
taacaaggag atttcttagt tcatatatca agaagtcttg aagttgggtg tttccagaat    2460
tggtaaaaac agcagctcat agaattttga gtattccatg agctgctcat tacagttctt    2520 tcctcttttct gctctgccat cttcaggata ttggttcttc ccctcatagt aataagatgg    2580
ctgtggcatt tccaaacatc caaaaaagg gaaggattta aggaggtgaa gtcgggtcaa      2640
aaataaaata tatatacata tatacattgc ttagaacgtt aaactattag agtatttccc    2700
ttccaaagag ggatgtttgg aaaaaactct gaaggagagg aggaattagt tgggatgcca    2760
atttcctctc cactgctgga catgagatgg agaggctgag ggacaggatc tataggcagc    2820
ttctaagagc gaacttcaca taggaaggga tctgagaaca cgttgccagg ggcttgagaa    2880
ggttactgag tgagttattg ggagtcttaa taaaataaac tagatattag gtccattcat    2940
taattagttc cagtttctcc ttgaaatgag taaaaactag aaggcttctc tccacagtgt    3000 tgtgccccctt cactcatttt tttttgagga aagggggtc tctgttaaca tctagcctaa    3060
agtatacaac tgcctggggg gcagggttag gaatctcttc actaccctga ttcttgattc    3120
ctggctctac cctgtctgtc ccttttcttt gaccagatct ttctcttccc tgaacgtttt    3180
cttctttccc tggacaggca gcctcctttg tgtgtattca gaggcagtga tgacttgctg    3240
tccaggcagc tccctcctgc acacagaatg ctcagggtca ctgaaccact gcttctcttt    3300
tgaaagtaga gctagctgcc actttcacgt ggcctccgca gtgtctccac ctacacccct    3360
gtgctcccct gccacactga tggctcaaga caaggctggc aaaccctccc agaaacatct    3420
ctggcccaga aagcctctct ctccctccct ctctcatgag gcacagccaa gccaagcgct    3480
catgttgagc cagtgggcca gccacagagc aaaagagggt ttattttcag tcccctctct    3540
ctgggtcaga accagagggc atgctgaatg ccccctgctt acttggtgag ggtgccccgc    3600
ctgagtcagt gctctcagct ggcagtgcaa tgcttgtaga agtaggagga aacagttctc    3660
actgggaaga agcaagggca agaacccaag tgcctcacct cgaaaggagg ccctgttccc    3720
tggagtcagg gtgaactgca aagctttggc tgagacctgg gatttgagat accacaaacc    3780
ctgctgaaca cagtgtctgt tcagcaaact aaccagcatt ccctacagcc tagggcagac    3840
aatagtatag aagtctggaa aaaacaaaa acagaatttg agaaccttgg accactcctg     3900
tccctgtagc tcagtcatca aagcagaagt ctggctttgc tctattaaga ttggaaatgt    3960
acactaccaa acactcagtc cactgttgag ccccagtgct ggaagggagg aaggcctttc    4020
ttctgtgtta attgcgtaga ggctacaggg gttagcctgg actaaaggca tccttgtctt    4080
ttgagctatt caccctcagta gaaaaggatc taagggaaga tcactgtagt ttagttctgt    4140
tgacctgtgc acctaccccct tggaaatgtc tgctggtatt tctaattcca caggtcatca    4200
```

```
gatgcctgct tgataatata taaacaataa aaacaacttt cacttcttcc tattgtaatc    4260
gtgtgccatg gatctgatct gtaccatgac cctacataag gctggatggc acctcaggct    4320
gagggcccca atgtatgtgt ggctgtgggt gtgggtggga gtgtgtctgc tgagtaagga    4380
acacgatttt caagattcta aagctcaatt caagtgacac attaatgata aactcagatc    4440
tgatcaagag tccggatttc taacagtcct tgctttgggg ggtgtgctga caacttagct    4500
caggtgcctt acatcttttc taatcacagt gttgcatatg agcctgccct cactccctct    4560
gcagaatccc tttgcacctg agaccctact gaagtggctg gtagaaaaag gggcctgagt    4620
ggaggattat cagtatcacg atttgcagga ttcccttctg ggcttcattc tggaaacttt    4680
tgttagggct gcttttctta agtgcccaca tttgatggag ggtggaaata atttgaatgt    4740
atttgattta taagtttttt ttttttttt gggttaaaag atggttgtag catttaaaat    4800
ggaaaatttt ctccttggtt tgctagtatc ttgggtgtat tctctgtaag tgtagctcaa    4860
ataggtcatc atgaaaggtt aaaaaagcga ggtggccatg ttatgctggt ggttaaggcc    4920
agggcctctc caaccactgt gccactgact tgctgtgtga ccctgggcaa gtcacttaac    4980
tataaggtgc ctcagttttc cttctgttaa atggggata ataatactga cctacctcaa    5040
agggcagttt tgaggcatga ctaatgcttt ttagaaagca ttttgggatc cttcagcaca    5100
ggaattctca agacctgagt attttttata ataggaatgt ccaccatgaa cttgatacgt    5160
ccgtgtgtcc cagatgctgt cattagtcta tatggttctc caagaaactg aatgaatcca    5220
ttggagaagc ggtggataac tagccagaca aaatttgaga atacataaac aacgcattgc    5280
cacggaaaca tacagaggat gccttttctg tgattgggtg ggatttttc ccttttatg    5340 tgggatatag tagttacttg tgacaagaat aatttggaa taatttctat taatatcaac    5400
tctgaagcta attgtactaa tctgagattg tgtttgttca taataaaagt gaagtgaatc    5460
tgattgcaaa aaa                                                       5473
```

<210> SEQ ID NO 10
<211> LENGTH: 359
<212> TYPE: PRT
<213> ORGANISM: Homo sapiens

<400> SEQUENCE: 10

```
Met Pro Ala His Leu Leu Gln Asp Asp Ile Ser Ser Tyr Thr Thr
1               5                   10                  15

Thr Thr Thr Ile Thr Ala Pro Pro Ser Arg Val Leu Gln Asn Gly Gly
            20                  25                  30

Asp Lys Leu Glu Thr Met Pro Leu Tyr Leu Glu Asp Ile Arg Pro
        35                  40                  45

Asp Ile Lys Asp Asp Ile Tyr Asp Pro Thr Tyr Lys Asp Lys Glu Gly
    50                  55                  60

Pro Ser Pro Lys Val Glu Tyr Val Trp Arg Asn Ile Ile Leu Met Ser
65                  70                  75                  80

Leu Leu His Leu Gly Ala Leu Tyr Gly Ile Thr Leu Ile Pro Thr Cys
                85                  90                  95

Lys Phe Tyr Thr Trp Leu Trp Gly Val Phe Tyr Phe Val Ser Ala
            100                 105                 110

Leu Gly Ile Thr Ala Gly Ala His Arg Leu Trp Ser His Arg Ser Tyr
        115                 120                 125

Lys Ala Arg Leu Pro Leu Arg Leu Phe Leu Ile Ile Ala Asn Thr Met
    130                 135                 140
```

```
Ala Phe Gln Asn Asp Val Tyr Glu Trp Ala Arg Asp His Arg Ala His
145                 150                 155                 160

His Lys Phe Ser Glu Thr His Ala Asp Pro His Asn Ser Arg Arg Gly
            165                 170                 175

Phe Phe Phe Ser His Val Gly Trp Leu Leu Val Arg Lys His Pro Ala
        180                 185                 190

Val Lys Glu Lys Gly Ser Thr Leu Asp Leu Ser Asp Leu Glu Ala Glu
    195                 200                 205

Lys Leu Val Met Phe Gln Arg Arg Tyr Lys Pro Gly Leu Leu Met
210                 215                 220

Met Cys Phe Ile Leu Pro Thr Leu Val Pro Trp Tyr Phe Trp Gly Glu
225                 230                 235                 240

Thr Phe Gln Asn Ser Val Phe Val Ala Thr Phe Leu Arg Tyr Ala Val
                245                 250                 255

Val Leu Asn Ala Thr Trp Leu Val Asn Ser Ala Ala His Leu Phe Gly
            260                 265                 270

Tyr Arg Pro Tyr Asp Lys Asn Ile Ser Pro Arg Glu Asn Ile Leu Val
        275                 280                 285

Ser Leu Gly Ala Val Gly Glu Gly Phe His Asn Tyr His His Ser Phe
290                 295                 300

Pro Tyr Asp Tyr Ser Ala Ser Glu Tyr Arg Trp His Ile Asn Phe Thr
305                 310                 315                 320

Thr Phe Phe Ile Asp Cys Met Ala Ala Leu Gly Leu Ala Tyr Asp Arg
                325                 330                 335

Lys Lys Val Ser Lys Ala Ala Ile Leu Ala Arg Ile Lys Arg Thr Gly
            340                 345                 350

Asp Gly Asn Tyr Lys Ser Gly
        355

<210> SEQ ID NO 11
<211> LENGTH: 4450
<212> TYPE: DNA
<213> ORGANISM: Homo sapiens

<400> SEQUENCE: 11
agccgatggg ggcggggaaa agtccggctg gccgggaca aaagccggat cccgggaagc      60
taccggctgc tggggtgctc cggattttgc ggggttcgtc gggcctgtgg aagaagcgcc    120
gcgcacggac ttcggcagag gtagagcagg tctctctgca gccatgtcgg ccaaggcaat    180
ttcagagcag acgggcaaag aactcctta caagttcatc tgtaccacct cagccatcca    240
gaatcggttc aagtatgctc gggtcactcc tgacacagac tgggcccgct tgctgcagga    300
ccacccctgg ctgctcagcc agaacttggt agtcaagcca gaccagctga tcaaacgtcg    360
tggaaaactt ggtctcgttg gggtcaacct cactctggat ggggtcaagt cctggctgaa    420
gccacggctg ggacaggaag ccacagttgg caaggccaca ggcttcctca agaactttct    480
gatcgagccc ttcgtccccc acagtcaggc tgaggagttc tatgtctgca tctatgccac    540
ccgagaaggg gactacgtcc tgttccacca cgagggggt gtggacgtgg gtgatgtgga    600
cgccaaggcc cagaagctgc ttgttggcgt ggatgagaaa ctgaatcctg aggacatcaa    660
aaaacacctg ttggtccacg cccctgaaga caagaaagaa attctggcca gttttatctc    720
cggcctcttc aatttctacg aggacttgta cttcacctac ctcgagatca atccccttgt    780
agtgaccaaa gatggagtct atgtccttga cttggcggcc aaggtggacg ccactgccga    840
ctacatctgc aaagtgaagt ggggtgacat cgagttccct ccccccttcg ggcgggaggc    900
```

```
atatccagag gaagcctaca ttgcagacct cgatgccaaa agtggggcaa gcctgaagct    960
gaccttgctg aaccccaaag ggaggatctg gaccatggtg gccggggggtg gcgcctctgt  1020
cgtgtacagc gataccatct gtgatctagg gggtgtcaac gagctggcaa actatgggga  1080
gtactcaggc gcccccagcg agcagcagac ctatgactat gccaagacta tcctctccct  1140
catgacccga gagaagcacc cagatggcaa gatcctcatc attggaggca gcatcgcaaa  1200
cttcaccaac gtggctgcca cgttcaaggg catcgtgaga gcaattcgag attaccaggg  1260
ccccctgaag gagcacgaag tcacaatctt tgtccgaaga ggtggcccca actatcagga  1320
gggcttacgg gtgatgggag aagtcgggaa gaccactggg atccccatcc atgtctttgg  1380
cacagagact cacatgacgg ccattgtggg catggccctg gccaccggc  ccatccccaa  1440
ccagccaccc acagcggccc acactgcaaa cttcctcctc aacgccagcg ggagcacatc  1500
gacgccagcc cccagcagga cagcatcttt ttctgagtcc agggccgatg aggtggcgcc  1560
tgcaaagaag gccaagcctg ccatgccaca agattcagtc ccaagtccaa gatccctgca  1620
aggaaagagc accaccctct tcagccgcca caccaaggcc attgtgtggg gcatgcagac  1680
ccgggccgtg caaggcatgc tggactttga ctatgtctgc tcccgagacg agccctcagt  1740
ggctgccatg gtctaccctt tcactgggga ccacaagcag aagttttact gggggcacaa  1800
agagatcctg atccctgtct tcaagaacat ggctgatgcc atgaggaagc atccggaggt  1860
agatgtgctc atcaactttg cctctctccg ctctgcctat gacagcacca tggagaccat  1920
gaactatgcc cagatccgga ccatcgccat catagctgaa ggcatccctg aggccctcac  1980
gagaaagctg atcaagaagg cggaccagaa gggagtgacc atcatcggac tgccactgt   2040
tggaggcatc aagcctgggt gctttaagat tggcaacaca ggtgggatgc tggacaacat  2100
cctggcctcc aaactgtacc gcccaggcag cgtggcctat gtctcacgtt ccggaggcat  2160
gtccaacgag ctcaacaata tcatctctcg gaccacggat ggcgtctatg agggcgtggc  2220
cattggtggg gacaggtacc cgggctccac attcatggat catgtgttac gctatcagga  2280
cactccagga gtcaaaatga ttgtggttct tggagagatt gggggcactg aggaatataa  2340
gatttgccgg ggcatcaagg agggccgcct cactaagccc atcgtctgct ggtgcatcgg  2400
gacgtgtgcc accatgttct cctctgaggt ccagtttggc catgctggag cttgtgccaa  2460
ccaggcttct gaaactgcag tagccaagaa ccaggctttg aaggaagcag gagtgtttgt  2520
gccccggagc tttgatgagc ttggagagat catccagtct gtatacgaag atctcgtggc  2580
caatggagtc attgtacctg cccaggaggt gccgccccca accgtgccca tggactactc  2640
ctgggccagg gagcttggtt tgatccgcaa acctgcctcg ttcatgacca gcatctgcga  2700
tgagcgagga caggagctca tctacgcggg catgcccatc actgaggtct tcaaggaaga  2760
gatgggcatt ggcggggtcc tcggcctcct ctggttccag aaaaggttgc ctaagtactc  2820
ttgccagttc attgagatgt gtctgatggt gacagctgat cacgggccag ccgtctctgg  2880
agcccacaac accatcattt gtgcgcgagc tgggaaagac ctggtctcca gcctcacctc  2940
ggggctgctc accatcgggg atcggttttgg gggtgccttg gatgcagcag ccaagatgtt  3000
cagtaaagcc tttgacagtg gcattatccc catggagttt gtgaacaaga tgaagaagga  3060
agggaagctg atcatgggca ttggtcaccg agtgaagtcg ataaacaacc cagacatgcg  3120
agtgcagatc ctcaaagatt acgtcaggca gcacttccct gccactcctc tgctcgatta  3180
tgcactggaa gtagagaaga ttaccacctc gaagaagcca aatcttatcc tgaatgtaga  3240
```

```
tggtctcatc ggagtcgcat ttgtagacat gcttagaaac tgtgggtcct ttactcggga    3300
ggaagctgat gaatatattg acattggagc cctcaatggc atctttgtgc tgggaaggag    3360
tatggggttc attggacact atcttgatca gaagaggctg aagcaggggc tgtatcgtca    3420
tccgtgggat gatatttcat atgttcttcc ggaacacatg agcatgtaac agagccagga    3480
accctactgc agtaaactga agacaagatc tcttccccca agaaaagtg tacagacagc     3540 tggcagtgga gcctgcttta tttagcaggg gcctggaatg taaacagcca ctggggtaca    3600
ggcaccgaag accaacatcc acaggctaac accccttcag tccacacaaa gaagcttcat    3660 attttttta taagcataga aataaaaacc aagccaatat ttgtgacttt gctctgctac      3720
ctgctgtatt tattatatgg aagcatctaa gtactgtcag gatgggtct tcctcattgt      3780 agggcgttag gatgttgctt tcttttttcca ttagttaaac attttttttct cctttggagg   3840 aagggaatga aacatttatg gcctcaagat actatacatt taaagcaccc caatgtctct    3900
cttttttttt ttttacttcc ctttcttctt ccttatataa catgaagaac attgtattaa    3960
tctgattttt aaagatcttt ttgtatgtta cgtgttaagg gcttgtttgg tatcccactg    4020
aaatgttctg tgttgcagac cagagtctgt ttatgtcagg gggatggggc cattgcatcc    4080
ttagccattg tcacaaaata tgtggagtag taacttaata tgtaaagttg taacatacat    4140
acatttaaaa tggaaatgca gaaagctgtg aaatgtcttg tgtcttatgt tctctgtatt    4200
tatgcagctg atttgtctgt ctgtaactga agtgtgggtc caaggactcc taactacttt    4260
gcatctgtaa tccacaaaga ttctgggcag ctgccacctc agtctcttct ctgtattatc    4320
atagtctggt ttaaataaac tatatagtaa caaaaaaaaa aaaaaaaaa aaaaaaaaa      4380 aaaaaaaaaa aaaaaaaaaa aaaaaaaaa aaaaaaaaa aaaaaaaaa aaaaaaaaa       4440 aaaaaaaaaa                                                                    4450

<210> SEQ ID NO 12
<211> LENGTH: 1101
<212> TYPE: PRT
<213> ORGANISM: Homo sapiens

<400> SEQUENCE: 12

Met Ser Ala Lys Ala Ile Ser Glu Gln Thr Gly Lys Glu Leu Leu Tyr
1               5                   10                  15

Lys Phe Ile Cys Thr Thr Ser Ala Ile Gln Asn Arg Phe Lys Tyr Ala
            20                  25                  30

Arg Val Thr Pro Asp Thr Asp Trp Ala Arg Leu Leu Gln Asp His Pro
        35                  40                  45

Trp Leu Leu Ser Gln Asn Leu Val Lys Pro Asp Gln Leu Ile Lys
    50                  55                  60

Arg Arg Gly Lys Leu Gly Leu Val Gly Val Asn Leu Thr Leu Asp Gly
65                  70                  75                  80

Val Lys Ser Trp Leu Lys Pro Arg Leu Gly Gln Glu Ala Thr Val Gly
                85                  90                  95

Lys Ala Thr Gly Phe Leu Lys Asn Phe Leu Ile Glu Pro Phe Val Pro
            100                 105                 110

His Ser Gln Ala Glu Glu Phe Tyr Val Cys Ile Tyr Ala Thr Arg Glu
        115                 120                 125

Gly Asp Tyr Val Leu Phe His His Glu Gly Gly Val Asp Val Gly Asp
    130                 135                 140

Val Asp Ala Lys Ala Gln Lys Leu Leu Val Gly Val Asp Glu Lys Leu
145                 150                 155                 160
```

-continued

```
Asn Pro Glu Asp Ile Lys Lys His Leu Leu Val His Ala Pro Glu Asp
                165                 170                 175
Lys Lys Glu Ile Leu Ala Ser Phe Ile Ser Gly Leu Phe Asn Phe Tyr
            180                 185                 190
Glu Asp Leu Tyr Phe Thr Tyr Leu Glu Ile Asn Pro Leu Val Val Thr
        195                 200                 205
Lys Asp Gly Val Tyr Val Leu Asp Leu Ala Ala Lys Val Asp Ala Thr
    210                 215                 220
Ala Asp Tyr Ile Cys Lys Val Lys Trp Gly Asp Ile Glu Phe Pro Pro
225                 230                 235                 240
Pro Phe Gly Arg Glu Ala Tyr Pro Glu Glu Ala Tyr Ile Ala Asp Leu
                245                 250                 255
Asp Ala Lys Ser Gly Ala Ser Leu Lys Leu Thr Leu Leu Asn Pro Lys
            260                 265                 270
Gly Arg Ile Trp Thr Met Val Ala Gly Gly Ala Ser Val Val Tyr
        275                 280                 285
Ser Asp Thr Ile Cys Asp Leu Gly Gly Val Asn Glu Leu Ala Asn Tyr
    290                 295                 300
Gly Glu Tyr Ser Gly Ala Pro Ser Glu Gln Gln Thr Tyr Asp Tyr Ala
305                 310                 315                 320
Lys Thr Ile Leu Ser Leu Met Thr Arg Glu Lys His Pro Asp Gly Lys
                325                 330                 335
Ile Leu Ile Ile Gly Gly Ser Ile Ala Asn Phe Thr Asn Val Ala Ala
            340                 345                 350
Thr Phe Lys Gly Ile Val Arg Ala Ile Arg Asp Tyr Gln Gly Pro Leu
        355                 360                 365
Lys Glu His Glu Val Thr Ile Phe Val Arg Arg Gly Gly Pro Asn Tyr
    370                 375                 380
Gln Glu Gly Leu Arg Val Met Gly Glu Val Gly Lys Thr Thr Gly Ile
385                 390                 395                 400
Pro Ile His Val Phe Gly Thr Glu Thr His Met Thr Ala Ile Val Gly
                405                 410                 415
Met Ala Leu Gly His Arg Pro Ile Pro Asn Gln Pro Thr Ala Ala
            420                 425                 430
His Thr Ala Asn Phe Leu Leu Asn Ala Ser Gly Ser Thr Ser Thr Pro
        435                 440                 445
Ala Pro Ser Arg Thr Ala Ser Phe Ser Glu Ser Arg Ala Asp Glu Val
    450                 455                 460
Ala Pro Ala Lys Lys Ala Lys Pro Ala Met Pro Gln Asp Ser Val Pro
465                 470                 475                 480
Ser Pro Arg Ser Leu Gln Gly Lys Ser Thr Thr Leu Phe Ser Arg His
                485                 490                 495
Thr Lys Ala Ile Val Trp Gly Met Gln Thr Arg Ala Val Gln Gly Met
            500                 505                 510
Leu Asp Phe Asp Tyr Val Cys Ser Arg Asp Glu Pro Ser Val Ala Ala
        515                 520                 525
Met Val Tyr Pro Phe Thr Gly Asp His Lys Gln Lys Phe Tyr Trp Gly
    530                 535                 540
His Lys Glu Ile Leu Ile Pro Val Phe Lys Asn Met Ala Asp Ala Met
545                 550                 555                 560
Arg Lys His Pro Glu Val Asp Val Leu Ile Asn Phe Ala Ser Leu Arg
                565                 570                 575
```

```
Ser Ala Tyr Asp Ser Thr Met Glu Thr Met Asn Tyr Ala Gln Ile Arg
            580                 585                 590

Thr Ile Ala Ile Ile Ala Glu Gly Ile Pro Glu Ala Leu Thr Arg Lys
        595                 600                 605

Leu Ile Lys Lys Ala Asp Gln Lys Gly Val Thr Ile Ile Gly Pro Ala
610                 615                 620

Thr Val Gly Gly Ile Lys Pro Gly Cys Phe Lys Ile Gly Asn Thr Gly
625                 630                 635                 640

Gly Met Leu Asp Asn Ile Leu Ala Ser Lys Leu Tyr Arg Pro Gly Ser
            645                 650                 655

Val Ala Tyr Val Ser Arg Ser Gly Gly Met Ser Asn Glu Leu Asn Asn
                660                 665                 670

Ile Ile Ser Arg Thr Thr Asp Gly Val Tyr Glu Gly Val Ala Ile Gly
            675                 680                 685

Gly Asp Arg Tyr Pro Gly Ser Thr Phe Met Asp His Val Leu Arg Tyr
            690                 695                 700

Gln Asp Thr Pro Gly Val Lys Met Ile Val Leu Gly Glu Ile Gly
705                 710                 715                 720

Gly Thr Glu Glu Tyr Lys Ile Cys Arg Gly Ile Lys Glu Gly Arg Leu
                725                 730                 735

Thr Lys Pro Ile Val Cys Trp Cys Ile Gly Thr Cys Ala Thr Met Phe
            740                 745                 750

Ser Ser Glu Val Gln Phe Gly His Ala Gly Ala Cys Ala Asn Gln Ala
            755                 760                 765

Ser Glu Thr Ala Val Ala Lys Asn Gln Ala Leu Lys Glu Ala Gly Val
770                 775                 780

Phe Val Pro Arg Ser Phe Asp Glu Leu Gly Glu Ile Ile Gln Ser Val
785                 790                 795                 800

Tyr Glu Asp Leu Val Ala Asn Gly Val Ile Val Pro Ala Gln Glu Val
                805                 810                 815

Pro Pro Pro Thr Val Pro Met Asp Tyr Ser Trp Ala Arg Glu Leu Gly
            820                 825                 830

Leu Ile Arg Lys Pro Ala Ser Phe Met Thr Ser Ile Cys Asp Glu Arg
            835                 840                 845

Gly Gln Glu Leu Ile Tyr Ala Gly Met Pro Ile Thr Glu Val Phe Lys
850                 855                 860

Glu Glu Met Gly Ile Gly Gly Val Leu Gly Leu Leu Trp Phe Gln Lys
865                 870                 875                 880

Arg Leu Pro Lys Tyr Ser Cys Gln Phe Ile Glu Met Cys Leu Met Val
                885                 890                 895

Thr Ala Asp His Gly Pro Ala Val Ser Gly Ala His Asn Thr Ile Ile
            900                 905                 910

Cys Ala Arg Ala Gly Lys Asp Leu Val Ser Ser Leu Thr Ser Gly Leu
            915                 920                 925

Leu Thr Ile Gly Asp Arg Phe Gly Gly Ala Leu Asp Ala Ala Ala Lys
    930                 935                 940

Met Phe Ser Lys Ala Phe Asp Ser Gly Ile Ile Pro Met Glu Phe Val
945                 950                 955                 960

Asn Lys Met Lys Lys Glu Gly Lys Leu Ile Met Gly Ile Gly His Arg
                965                 970                 975

Val Lys Ser Ile Asn Asn Pro Asp Met Arg Val Gln Ile Leu Lys Asp
            980                 985                 990

Tyr Val Arg Gln His Phe Pro Ala  Thr Pro Leu Leu Asp  Tyr Ala Leu
```

|  |  | 995 |  |  | 1000 |  |  |  | 1005 |  |  |
|---|---|---|---|---|---|---|---|---|---|---|---|
| Glu | Val | Glu | Lys | Ile | Thr | Thr | Ser | Lys | Lys | Pro | Asn | Leu | Ile | Leu |
|  |  | 1010 |  |  | 1015 |  |  |  | 1020 |

Asn Val Asp Gly Leu Ile Gly Val Ala Phe Val Asp Met Leu Arg
    1025            1030            1035

Asn Cys Gly Ser Phe Thr Arg Glu Glu Ala Asp Glu Tyr Ile Asp
    1040            1045            1050

Ile Gly Ala Leu Asn Gly Ile Phe Val Leu Gly Arg Ser Met Gly
    1055            1060            1065

Phe Ile Gly His Tyr Leu Asp Gln Lys Arg Leu Lys Gln Gly Leu
    1070            1075            1080

Tyr Arg His Pro Trp Asp Asp Ile Ser Tyr Val Leu Pro Glu His
    1085            1090            1095

Met Ser Met
    1100

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cggcgctgct gaccgacatc                                              20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcgcagatcg cggagccat                                               19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caagcttcta aagggcatcg                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cacagggaca acctggagtt                                              20

<210> SEQ ID NO 17
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 17
cgacgtggct ttttcttctc                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcccatcccc aaccagccac                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcctgccagt aacagggaag                                              20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctctccgttc agattgaagg gg                                           22

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gagtcaacgg atttggtcgt                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccctgcccca ctcccagcat                                              20

<210> SEQ ID NO 23
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 23
ccctgcccca ctcccagcat                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agtagggaga gaagccagcc                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
actccacagg tgggaacaag                                                    20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccttctcttt gacagctggg                                                    20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ttgcaggcgc cacctcatcg                                                    20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aggggaagtg tcagtacccg                                                    20

<210> SEQ ID NO 29
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 29
aatcccgcct ccatcctaac t                                              21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ttgaggtcaa tgaaggggtc                                                20
```

COMPOSITIONS AND METHODS FOR TREATING CANCER WITH ABERRANT LIPOGENIC SIGNALING

CROSS-REFERENCE TO RELATED APPLICATIONS

This application is a continuation of co-pending U.S. application Ser. No. 14/410,352 filed Dec. 22, 2014, which is a 35 U.S.C. § 371 National Phase Entry Application of International Application No. PCT/US2013/044887 filed Jun. 10, 2013, which designates the U.S., and which claims benefit under 35 U.S.C. § 119(e) of U.S. Provisional Application No. 61/663,875 filed Jun. 25, 2012, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Jun. 7, 2013, is named 003252-071731-PCT_SL.txt and is 104,058 bytes in size.

TECHNOLOGICAL FIELD

Embodiments of the technology described herein relate to treatments for cancer.

BACKGROUND

A hallmark of rapidly proliferating tumor cells is increased lipogenesis, i.e. increased production of lipids. Although most normal cells acquire the bulk of their fatty acids from circulation, tumor cells synthesize more than 90% of their own required lipids. The perturbed lipogenesis regulation of cancer cells thus offers targets for the development of new cancer therapies.

The regulation of lipogenesis in relation to cancer is also of importance due to the link between obesity and cancer. For example, epidemiological studies have identified obesity as the most common risk factor for endometrial cancer. Obese women have a 2-4 times greater risk of developing endometrial cancer compared to women of normal weight. As the number of people affected by obesity is expectedly growing, particularly in developing countries, endometrial cancer will continue to be a serious public health problem.

SUMMARY

Therapies that can target the aberrant lipogenesis of tumor cells and/or cells predisposed to become tumor cells will be of use in treating and preventing, e.g., the growing concern of endometrial cancer. Embodiments of the technology described herein are based on the inventors' discovery that pinacolyl boronate substituted stilbenes inhibit sterol regulatory binding protein 1 (SREBP1) and can be used to treat cancers expressing abnormally high levels of SREBP1.

Accordingly, in one aspect, provided herein are compounds which inhibit SREBP1. In some embodiments, the compounds can be selected from the group consisting of:

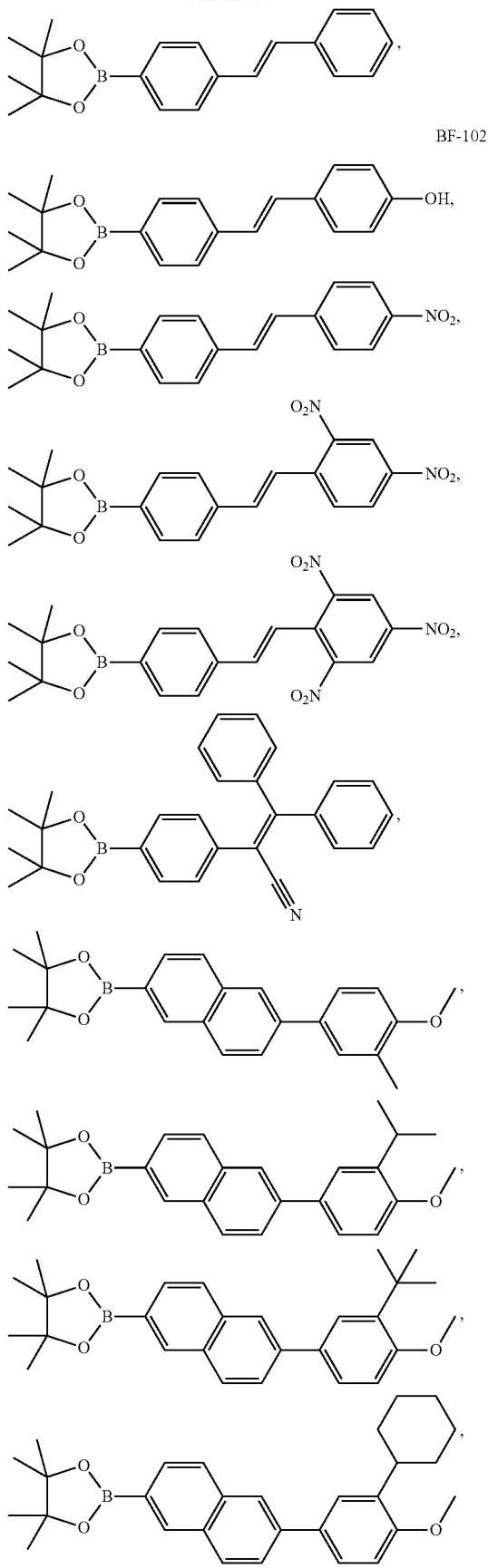

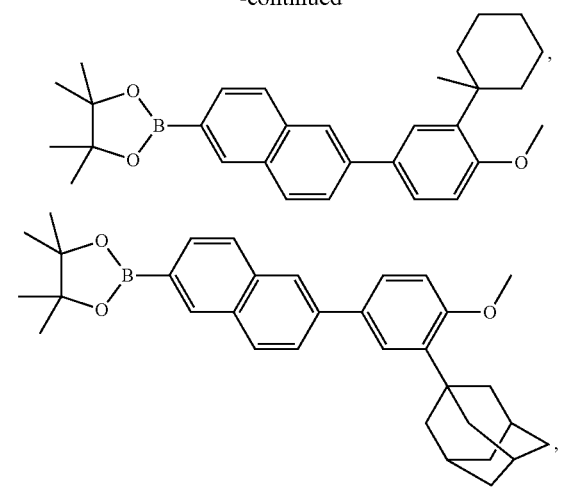
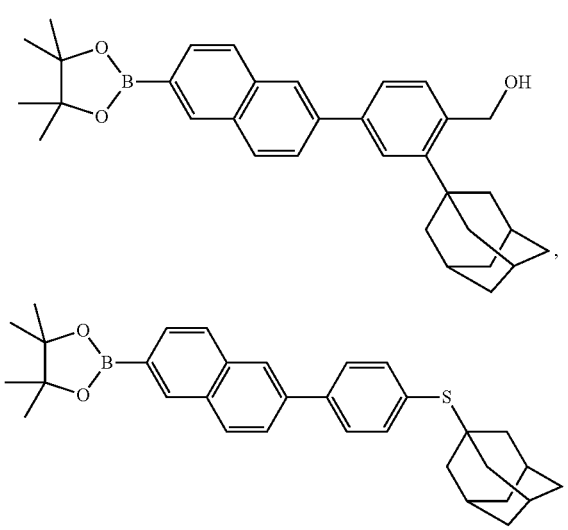
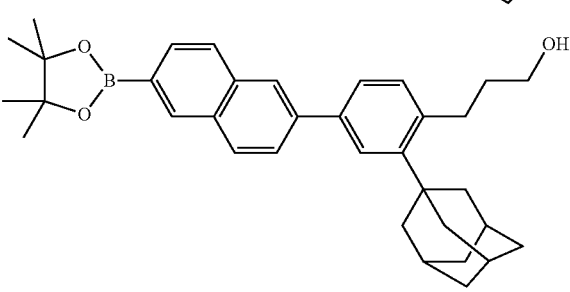
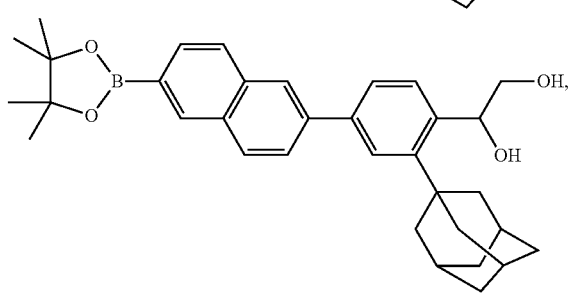
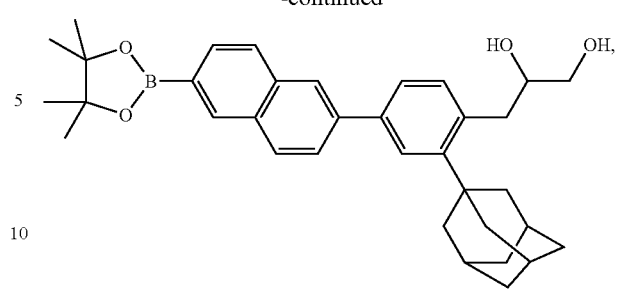
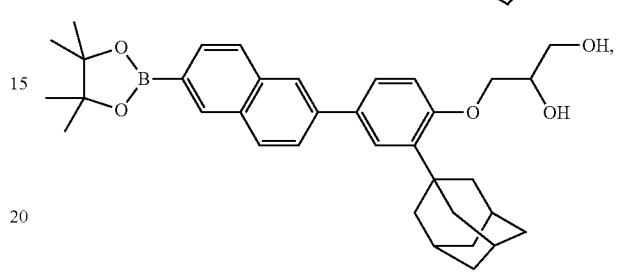
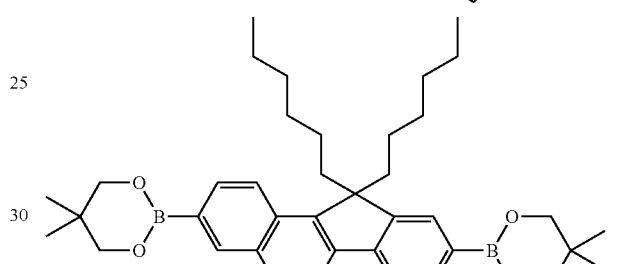
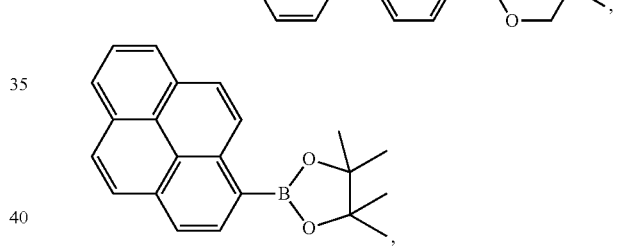
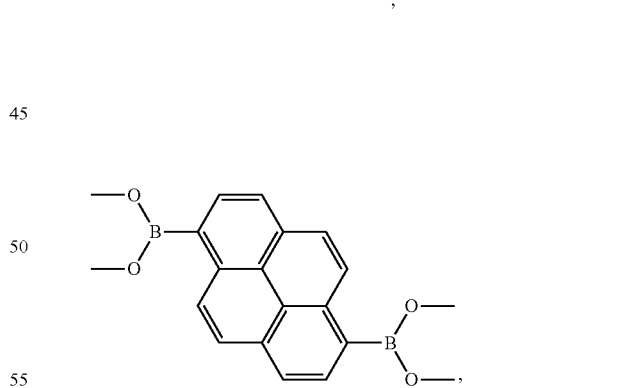
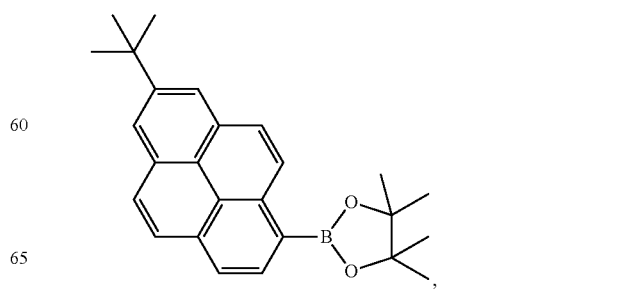

-continued
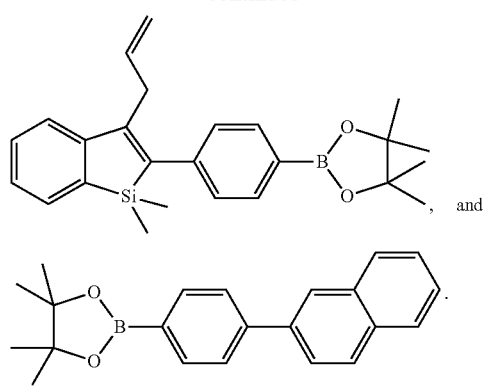, and
In some embodiments, the compounds can be selected from the group consisting of:
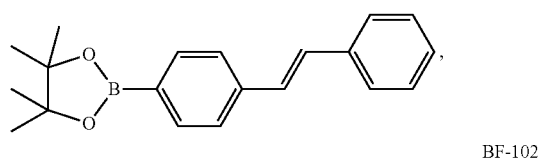
BF-102
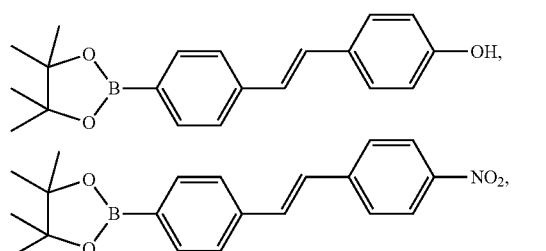
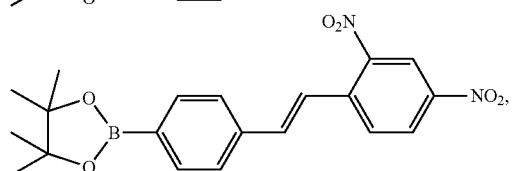
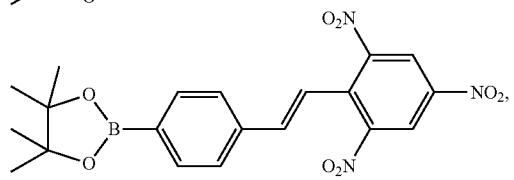
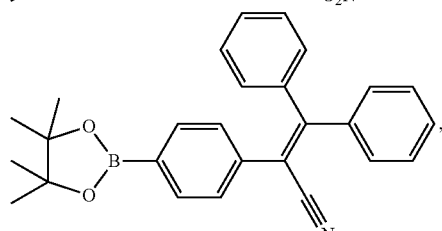
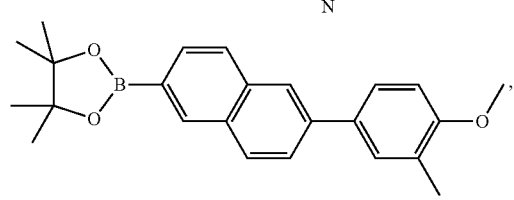
-continued
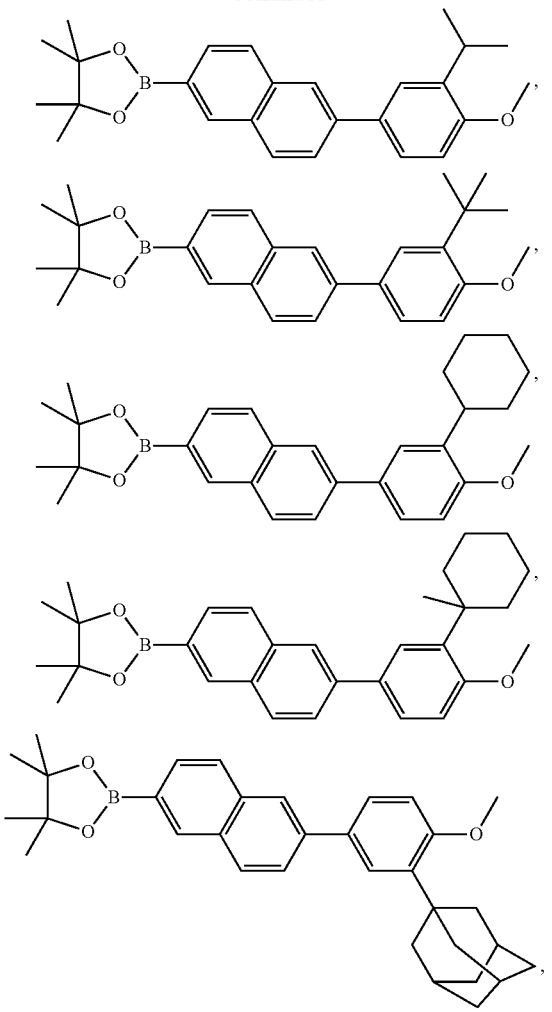
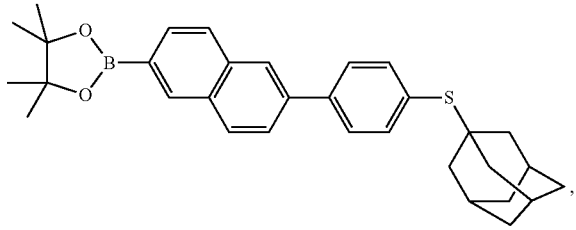

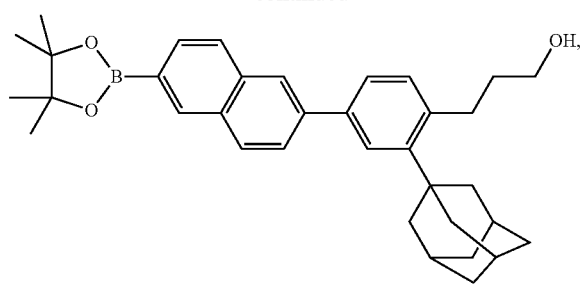
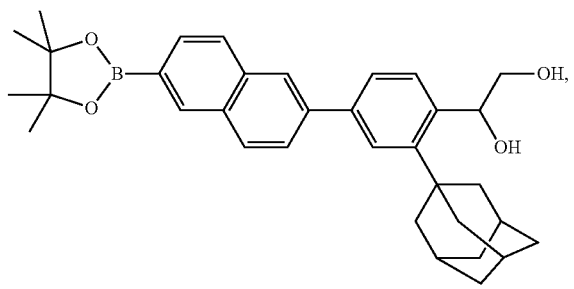
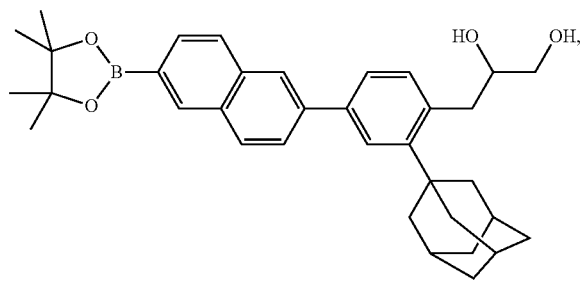
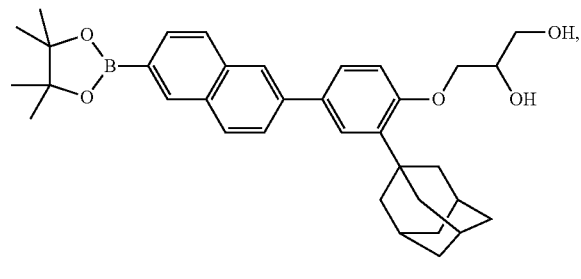
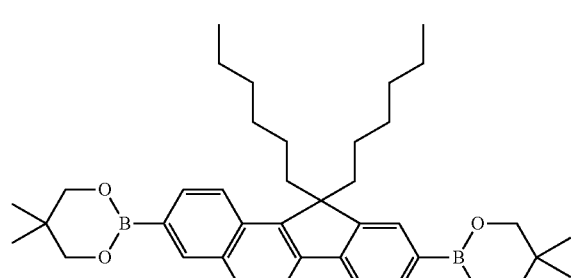
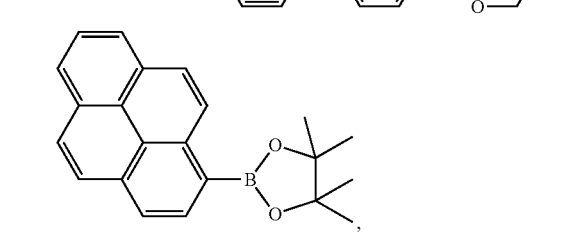
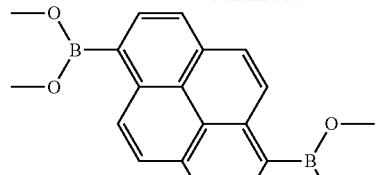
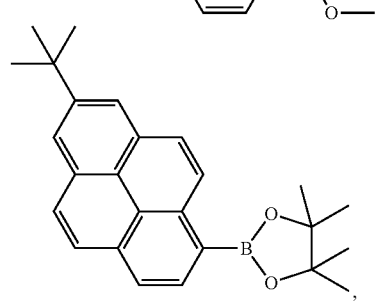
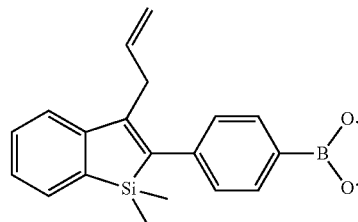
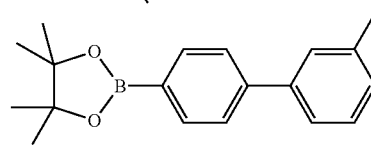, and
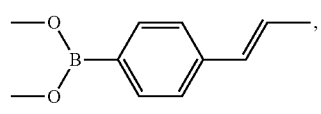.
In some embodiments, the compounds can be selected from the group consisting of:
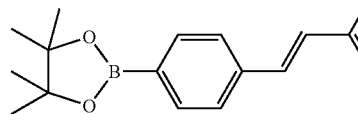
BF-175
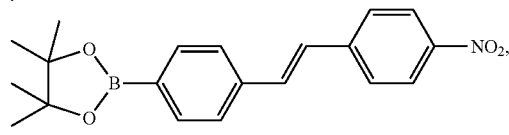
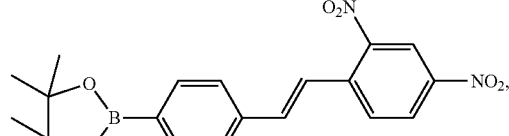
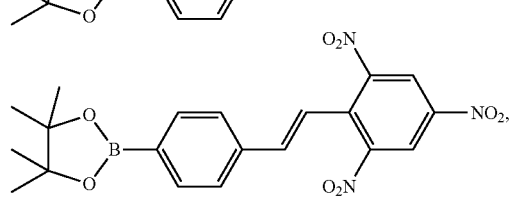

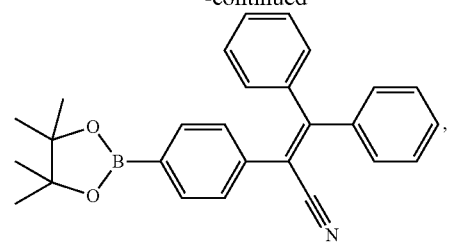
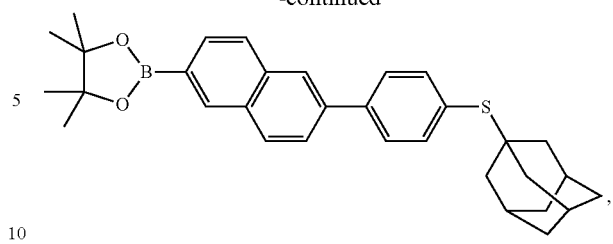
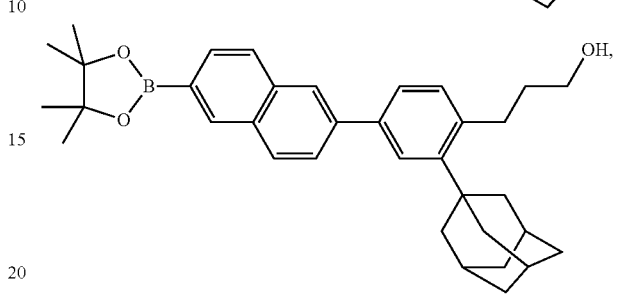
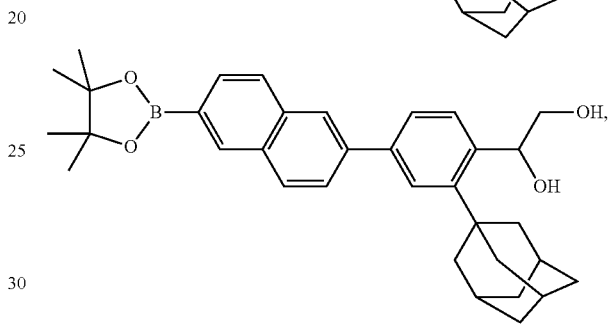
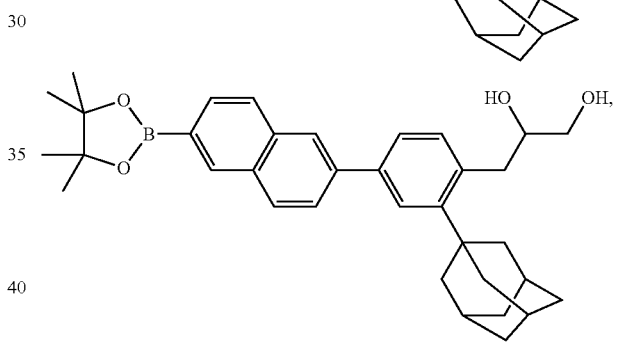
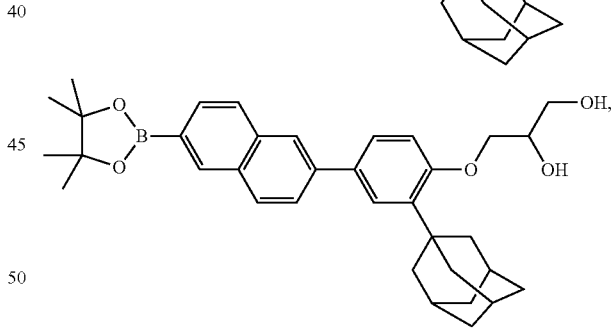
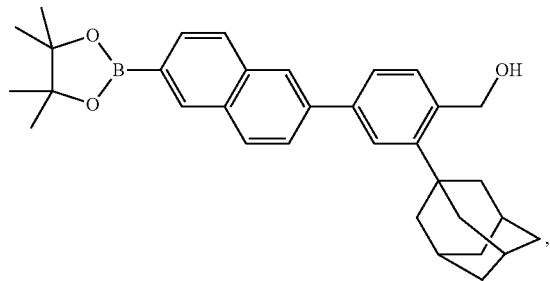
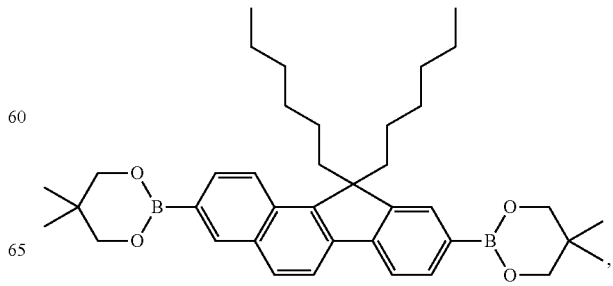

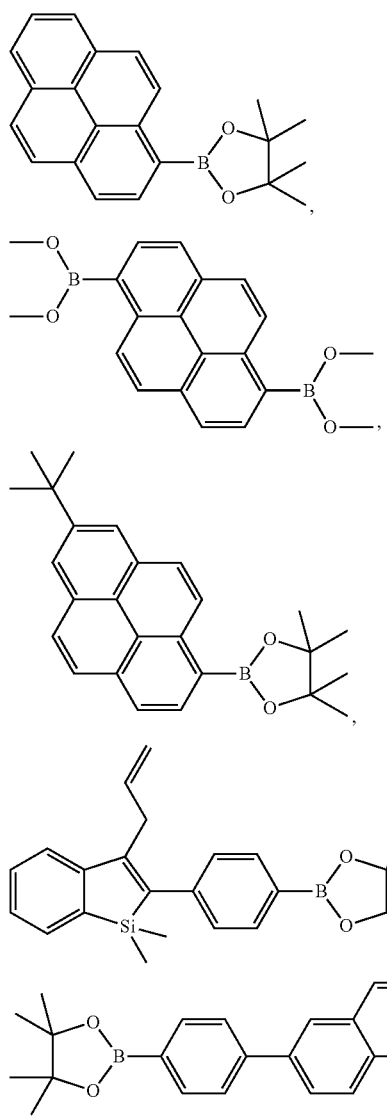
In some embodiments, the compounds can be selected from the group consisting of:
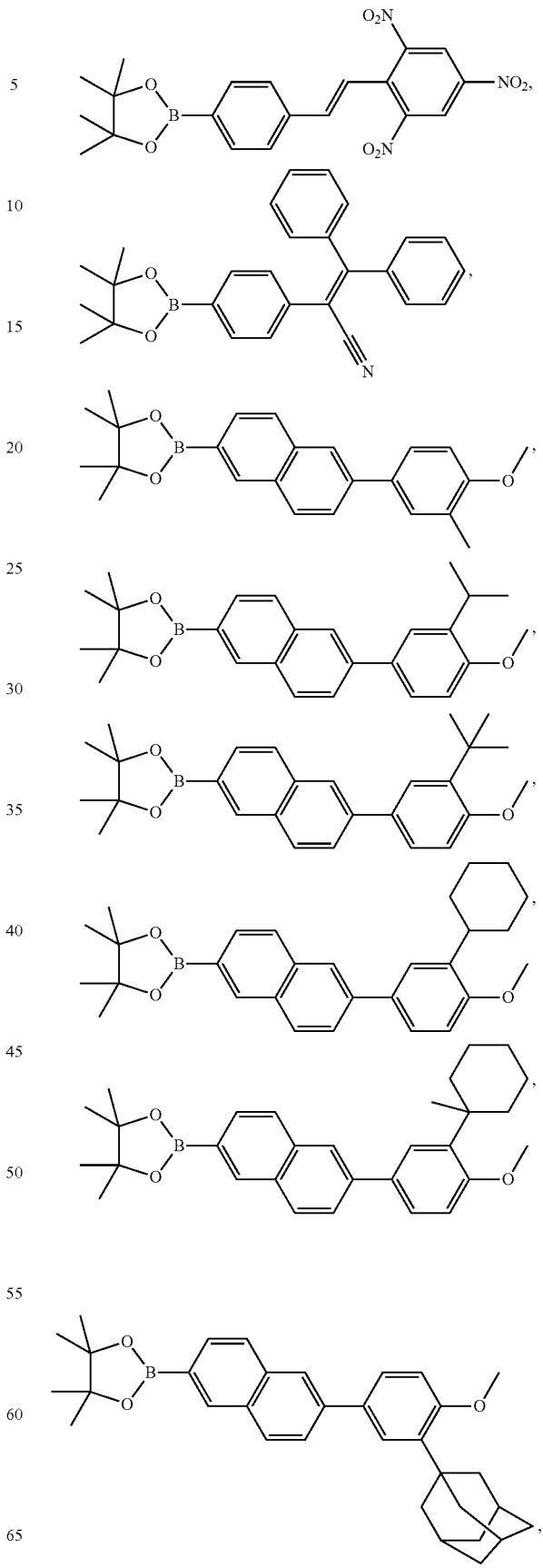

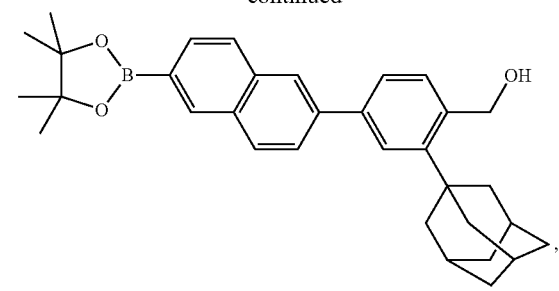

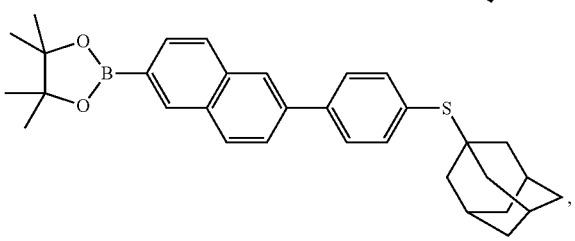

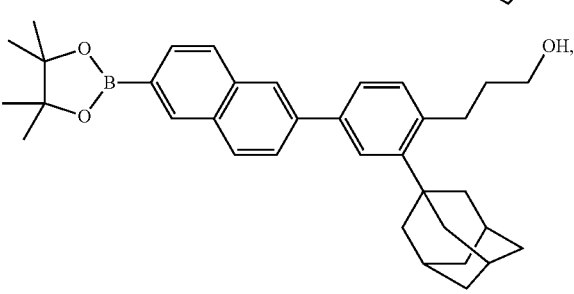

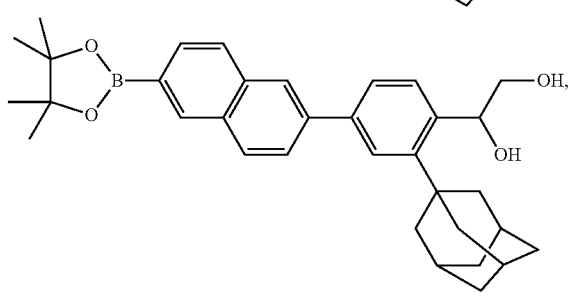

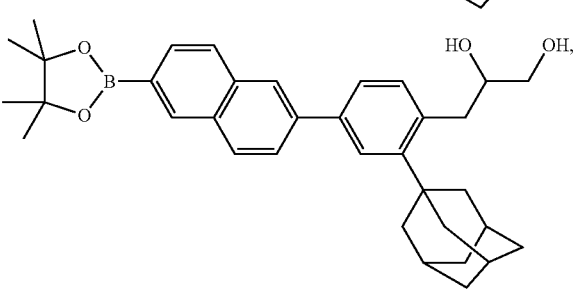

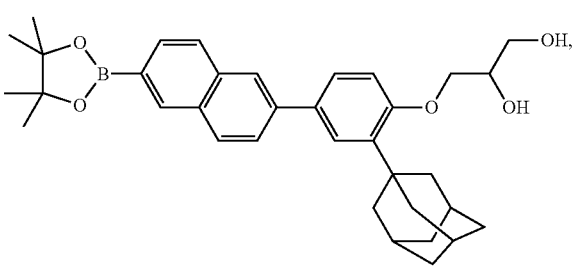

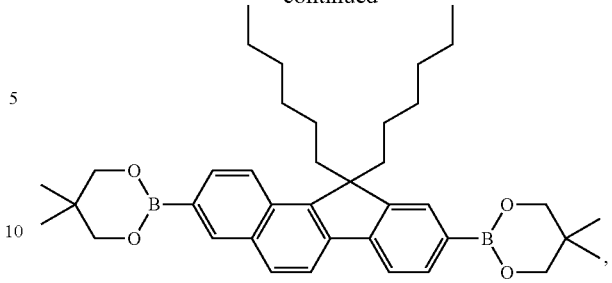

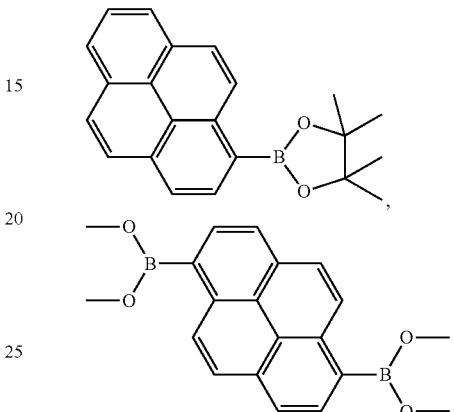

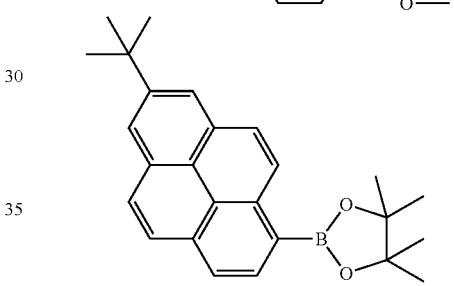

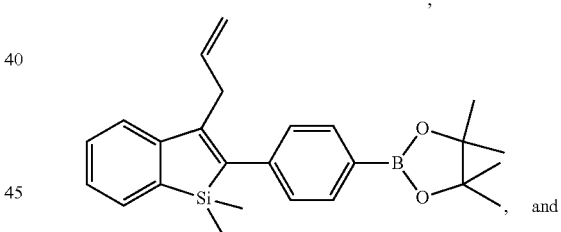

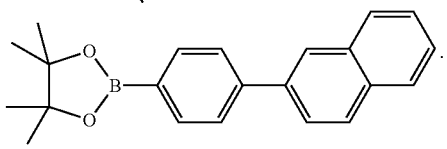

In one aspect, the technology described herein relates to a method of treating cancer in a subject, the method comprising administering to the subject an inhibitor of sterol regulatory binding protein 1 (SREBP1) as described herein. In some embodiments, the method can further comprise a first step of selecting a subject having cancer cells which express abnormal levels of sterol regulatory binding protein 1 (SREBP1). In some embodiments, the cells which express abnormal levels of sterol regulatory binding protein 1 (SREBP1) can be cells which have abnormal levels of SREBP1 polypeptide.

In some embodiments, the method can further comprise a first step of selecting a subject having cancer cells which express abnormal amounts of Erb2. In some embodiments, the method can further comprise a first step of selecting a subject having cancer cells which express abnormal amounts of at least one gene selected from the group consisting of: FASN, SCD1 or ACLY.

In some embodiments, the subject can have an endometrial cancer. In some embodiments, the cancer can be selected from the group consisting of: prostate cancer; breast cancer; colorectal cancer; colorectal carcinoma; hepatocarcinoma; endometrial adenocarcinoma; uterine cancer; leukemia; lung cancer; central nervous system cancer; melanoma; ovarian cancer; renal cancer; and pancreatic cancer.

In one aspect, the technology described herein relates to a pharmaceutical composition comprising an inhibitor of SREBP1 as described herein. In some embodiments, the composition can further comprise a pharmaceutically acceptable carrier.

In one aspect, the technology described herein relates to the use of an inhibitor of sterol regulatory binding protein 1 (SREBP1) to treat cancer. In some embodiments, the cancer can be comprised of cells expressing abnormal levels of sterol regulatory binding protein 1 (SREBP1). In some embodiments, the cells which express abnormal levels of sterol regulatory binding protein 1 (SREBP1) can be cells which have abnormal levels of SREBP1 polypeptide.

In some embodiments, the cancer can be comprised of cells expressing abnormal amounts of Erb2. In some embodiments, the cancer can be comprised of cells expressing abnormal amounts of at least one gene selected from the group consisting of: FASN, SCD1 or ACLY.

In some embodiments, the cancer can be an endometrial cancer. In some embodiments, the cancer can be selected from the group consisting of: prostate cancer; breast cancer; colorectal cancer; colorectal carcinoma; hepatocarcinoma; endometrial adenocarcinoma; uterine cancer; leukemia; lung cancer; central nervous system cancer; melanoma; ovarian cancer; renal cancer; and pancreatic cancer.

BRIEF DESCRIPTION OF THE DRAWINGS

FIG. 1A depicts boxplots of IHC staining score for SREBP1 in normal tissue and endometrial cancer. FIG. 1B depicts a graph of quantitative RT-PCR analysis of mRNA abundance of lipogenic genes including SREBP1a, SREBP1c, SREBP2, and SCD1. The relative expression levels of lipogenic gene were calculated as fold change compared to normal where the mRNA abundance was set as 1.

FIGS. 2A-2F demonstrate SREBP1 is required for expression of lipogenic genes, cell proliferation, and cell migration in endometrial cancer cells. (FIG. 2A). Western blot (WB) analysis of lipogenic gene expression in commonly used endometrial cancer cell lines. Actin serves as protein loading control. (FIG. 2B). Quantitative RT-PCR analysis of mRNA abundance of SREBP1a and SREBP1c in endometrial cancer cells. RNA abundance was shown as fold change relative to that in ECC-1 cells. (FIG. 2C). AN3-CA cells were transiently transfected with shRNA targeting human SREBP1 (shSREBP1). The cells stably expressing shSREBP1 were selected by antibiotics. WB showed reduced protein expression of SREBP1. (FIG. 2D). Quantitative RT-PCR analysis of mRNA abundance of SREBP1a and its target genes including FASN and SCD1. (FIG. 2E). AN3-CA cells knockdown of endogenous SREBP1 are partially defective for cell growth. Cellular growth was determined by counting the cells at different time points. (FIG. 2F) Boyden chamber assays were performed to determine the cell migration ability. Transwell assays were performed to determine cell migration. $1 \times 10^5$ cells were seeded in upper chamber. After 6 hrs, the medium in upper chamber was replaced with serum-free medium. The lower chamber contains medium supplemented with 10% FBS which serves as chemo-attractant. 48 hrs post cell seeding, cells that migrate across the pore were counted and plotted.

(FIG. 3A). *Drosophila* larvae fed with BF175. The fat body was separated and stained with Oil-Red O. Signaling was quantified. (FIG. 3B). AN3-CA cells were treated with increasing doses of BF175. Cells were lysed after 24 hrs and then subjected to Western blot to detect the protein abundance of SREBP1 and its target genes. GDI served as protein loading control. (FIG. 3C). AN3-CA cells were treated with increasing doses of BF175 as indicated. Cells were lysed after 24 hrs and then subjected to qRT-PCR to detect the mRNA expression of SREBP1 and its target genes as indicated. (FIG. 3D, 3E). FASN (FIG. 3D) and Scd (FIG. 3E) promoter-driven luciferase reporter activity was included as surrogate measure of SREBP1 transcriptional activity. HEK 293T cells transfected with reporter plasmid together with a vector encoding nSREBP1 were treated with increasing doses of BF175.

FIGS. 4A-4C demonstrate that cellular proliferation is repressed by BF175 in SREBP1 expressing cells. (FIG. 4A). Endometrial cancer cells were seeded 24 hrs prior to treatment with increasing doses of BF175. 48 hrs post treatment, cells were subjected to MTT assays to determine the cell viability. BF175 significantly represses the proliferation of RL95-2 and AN3-CA cells, where SREBP1 expression is relatively high. (FIG. 4B). $5 \times 10^5$ cells were seeded per well in 6-well plate and treated with increased dose of BF175. The cell number was counted 48 hrs post-treatment. (FIG. 4C). AN3-CA cells were starved with serum-free medium and released by adding 10% serum to the medium in the presence of BrdU. Cells were either treated with BF175 or vehicle control. The BrdU was stained after 6 hrs and BrdU-positive cells were counted.

(FIG. 5A). AC3-CA cells were seeded 24 hrs prior to treatment with increased dose of BF175 for 48 hrs. Cells were subjected to flow cytometry assays to determine the percentage of apoptotic cell death (cells in sub-G1 phase). (FIG. 5B).

DETAILED DESCRIPTION

Figure 1A:
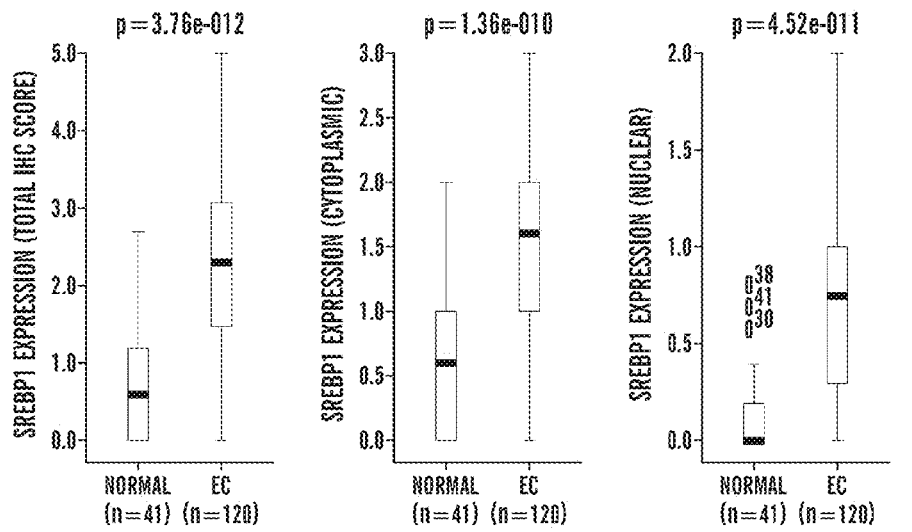
FIGS. 1A-1B demonstrate SREBP1 expression in endometrial cancer (EC) determined by IHC.
Figure 1B:
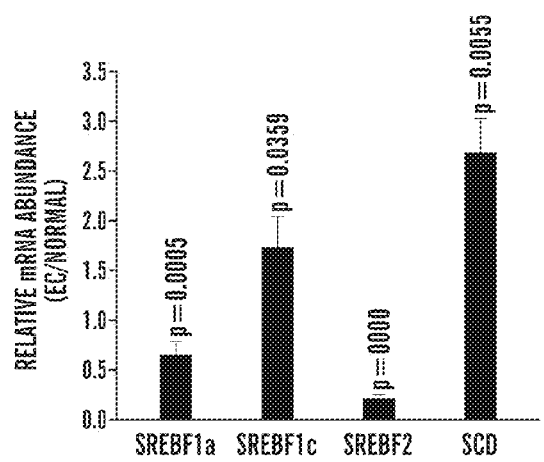

Embodiments of the technology described herein are based on the discovery that compounds as described herein can inhibit sterol regulatory binding protein 1 (SREBP1), a gene which is upregulated in certain cancers, e.g. endometrial cancers, and which thereby contributes to the increased level of lipogenesis displayed by those cancers. Accordingly, provided herein are compositions and methods relating to the treatment of cancers by administering SREBP1 inhibitors. In some embodiments, the cancer is an endometrial cancer. In some embodiments, the cancer is comprised of cells which express abnormal levels of SREBP1.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The terms "decrease," "reduce," "reduced", "reduction", "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the reference, or any decrease between 10-99% as compared to the absence of a given treatment.

The terms "increase", "increased" or "enhance" or "activate" are all used herein to generally mean an increase by a statically significant amount; for the avoidance of doubt, the terms "increased", "increase" or "enhance" or "activate" typically means an increase of at least 10% as compared to a reference, for example an increase of at least about 20%, or at least about 30%, or at least about 40%, or at least about 50%, or at least about 60%, or at least about 70%, or at least about 80%, or at least about 90%, or up to and including a 100% increase or any increase between 10-100% as compared to a reference, or at least about a 2-fold, or at least about a 3-fold, or at least about a 4-fold, or at least about a 5-fold or at least about a 10-fold increase, or any increase between 2-fold and 10-fold or greater as compared to a reference.

The term "biological sample" as used herein denotes a sample taken or isolated from a biological organism, e.g., cancer biopsy sample, blood sample, cell lysate, a homogenate of a tissue sample from a subject, or a fluid sample from a subject. Exemplary biological samples include, but are not limited to, cancer tissue biopsies or blood and/or serum samples. In some embodiments, the sample is from a resection, biopsy, or core needle biopsy. In addition, fine needle aspirate samples can be used. In some embodiments, samples can be either paraffin-embedded or frozen tissue. The term "biological sample" can also include untreated or pretreated (or pre-processed) biological samples. In some embodiments, the biological sample can be an untreated biological sample. As used herein, the phrase "untreated biological sample" refers to a biological sample that has not had any prior sample pre-treatment except for dilution and/or suspension in a solution. Exemplary methods for treating a biological sample include, but are not limited to, centrifugation, filtration, sonication, homogenization, heating, freezing and thawing, and any combinations thereof. The skilled practitioner is aware of methods and processes appropriate for pre-processing of biological samples required for determination of levels of polypeptides or nucleotides as described herein.

The sample can be obtained by removing a sample of cells from a subject, but can also be accomplished by using previously isolated cells (e.g. isolated at a prior timepoint and isolated by the same or another person). In addition, the biological sample can be freshly collected or a previously collected sample. In some embodiments, a biological sample is a biological fluid. Examples of biological fluids include, but are not limited to, saliva, blood, sputum, an aspirate, and any combinations thereof. In some embodiments, the biological sample is a frozen biological sample, e.g., a frozen tissue or fluid sample such as blood. The frozen sample can be thawed before employing methods, assays and systems of the invention. After thawing, a frozen sample can be centrifuged before being subjected to methods, assays and systems of the invention. In some embodiments, the biological sample can be treated with at least one chemical reagent, such as a protease inhibitor. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. In addition, or alternatively, chemical and/or biological reagents can be employed to release nucleic acid or protein from the sample. A biological sample can contain cells, but the term can also refer to non-cellular biological material, such as non-cellular fractions that can be used to measure gene expression levels.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used, for example, as subjects that represent animal models of, for example, cancer. In addition, the methods described herein can be used to treat domesticated animals and/or pets. A subject can be male or female.

A subject can be one who has been previously diagnosed with or identified as suffering from or having a condition in need of treatment (e.g. cancer) or one or more complications related to such a condition, and optionally, have already undergone treatment for cancer or the one or more complications related to cancer. Alternatively, a subject can also be one who has not been previously diagnosed as having cancer or one or more complications related to cancer. For example, a subject can be one who exhibits one or more risk factors for cancer or one or more complications related to cancer or a subject who does not exhibit risk factors. A "subject in need" of treatment for a particular condition can be a subject having that condition, diagnosed as having that condition, or being at risk of developing that condition.

As used herein, the term "proteins" and "polypeptides" are used interchangeably herein to designate a series of amino acid residues connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of their size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA or cDNA. Other suitable nucleic acid molecules are RNA, including mRNA.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the terms "alkyl," "alkenyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopentyl, cyclohexyl, cyclopropylmethyl, adamantly, norbornane, and norbornene. This is also true of groups that include the prefix "alkyl-," such as alkylcarboxylic acid, alkyl alcohol, alkylcarboxylate, alkylaryl, and the like. Examples of suitable alkylcarboxylic acid groups are methylcarboxylic acid, ethylcarboxylic acid, and the like. Examples of suitable alkylacohols are methylalcohol, ethylalcohol, isopropylalcohol, 2-methylpropan-1-ol, and the like. Examples of suitable alkylcarboxylates are methylcarboxylate, ethylcarboxylate, and the like. Examples of suitable alkyl aryl groups are benzyl, phenylpropyl, and the like.

These may be straight chain or branched, saturated or unsaturated aliphatic hydrocarbon, which may be optionally inserted with N, O, or S. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like.

As used herein, the term "alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

As used herein, the term "alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

The term "aryl" as used herein includes carbocyclic aromatic rings or ring systems. As used herein, the term "aryl" refers to an aromatic 5-8 membered monocyclic, 8-12 membered bicyclic, or 11-14 membered tricyclic ring system. Examples of aryl groups include phenyl, naphthyl, biphenyl, fluorenyl and indenyl.

The term "heteroaryl" includes aromatic rings or ring systems that contain at least one ring hetero atom (e.g., O, S, N). As used herein, the term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, thiazolyl, benzimidazolyl, pyrimidinyl, thiophenyl or thienyl, quinolinyl, indolyl, oxazolyl, isoquinolinyl, isoindolyl, thiazolyl, pyrrolyl, tetrazolyl, pyrazolyl, oxazolyl, thiazolyl, benzofuranyl, benzothiophenyl, carbazolyl, benzoxazolyl, benzimidazolyl, quinoxalinyl, benzothiazolyl, naphthyridinyl, isoxazolyl, isothiazolyl, purinyl, quinazolinyl, and the like.

The aryl, and heteroaryl groups can be unsubstituted or substituted by one or more substituents independently selected from the group consisting of alkyl, alkoxy, methylenedioxy, ethylenedioxy, alkylthio, haloalkyl, haloalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, aryloxycarbonyl, heteroaryloxycarbonyl, arylthiocarbonyl, heteroarylthiocarbonyl, alkanoyloxy, alkanoylthio, alkanoylamino, arylcarbonyloxy, arylcarbonylthio, alkylaminosulfonyl, alkylsulfonyl, arylsulfonyl, heteroarylsulfonyl, aryldiazinyl, alkylsulfonylamino, arylsulfonylamino, arylalkylsulfonylamino, alkylcarbonylamino, alkenylcarbonylamino, arylcarbonylamino, arylalkylcarbonylamino, arylcarbonylaminoalkyl, heteroarylcarbonylamino, heteroarylalkycarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonylamino, alkenylaminocarbonylamino, arylaminocarbonylamino, arylalkylaminocarbonylamino, heteroarylaminocarbonylamino, heteroarylalkylaminocarbonylamino and, in the case of heterocyclyl, oxo. If other groups are described as being "substituted" or "optionally substituted," then those groups can also be substituted by one or more of the above enumerated substituents.

The term "arylalkyl," as used herein, refers to a group comprising an aryl group attached to the parent molecular moiety through an alkyl group.

As used herein, the term "cyclyl" refers to a nonaromatic 5-8 membered monocyclic, 8-12 membered bicyclic, or 11-14 membered tricyclic ring system, which can be saturated or partially unsaturated. Representative saturated cyclyl groups include, but are not limited to, cyclopropyl, cyclobutyl, cyclopentyl, cyclopentenyl, cyclohexyl, cyclohexenyl, cycloheptyl, cyclooctyl, and the like; while unsaturated cyclyl groups include cyclopentenyl and cyclohexenyl, and the like.

The terms "heterocycle", "heterocyclyl" and "heterocyclic group" are recognized in the art and refer to nonaromatic 3- to about 14-membered ring structures, such as 3- to about 7-membered rings, whose ring structures include one to four heteroatoms, 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. The heterocycle may include portions which are saturated or unsaturated. In some embodiments, the heterocycle may include two or more rings (e.g., cycloalkyls, cycloalkenyls, cycloalkynyls, aryls and/or heterocyclyls) in which two or more carbons are common to two adjoining rings, e.g., the rings are "fused rings." In some embodiments, the heterocycle may be a "bridged" ring, where rings are joined through non-adjacent atoms, e.g., three or more atoms are common to both rings. Each of the rings of the heterocycle may be optionally substituted. Examples of heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, dioxane, morpholine, tetrahydrofurane, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with substituents including, for example, halogen, aryl, heteroaryl, alkyl, heteroalkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $CF_3$, CN, or the like.

As used herein, the term "halogen" refers to iodine, bromine, chlorine, and fluorine.

As used herein, the terms "optionally substituted alkyl," "optionally substituted cyclyl," "optionally substituted heterocyclyl," "optionally substituted aryl," and "optionally substituted heteroaryl" means that, when substituted, at least one hydrogen atom in said alkyl, cyclyl, heterocyclyl, aryl, or heteroaryl is replaced with a substituent. In the case of an oxo substituent (=O) two hydrogen atoms are replaced. In this regard, substituents include oxo, halogen, alkyl, cyclyl, heterocyclyl, aryl, heteroaryl, —CN, —$OR^x$, —$NR^xR^y$, —$NR^xC(=O)R^y$, —$NR^xSO_2R^y$, —$C(=O)R^x$, —$C(=O)OR^x$, —$C(=O)NR^xR^y$, —$SO_nR^x$ and —$SO_nNR^xR^y$, wherein n is 0, 1 or 2, $R^x$ and $R^y$ are the same or different and independently hydrogen, alkyl, cyclyl, heterocyclyl, aryl or heterocycle, and each of said alkyl, cyclyl, heterocyclyl, aryl and heterocycle substituents may be further substituted with one or more of oxo, halogen, —OH, —CN, alkyl, —$OR^x$, heterocycle, —$NR^xR^y$, —$NR^xC(=O)R^y$, —$NR^xSO_2R^y$, —$C(=O)R^x$, —$C(=O)OR^x$, —$C(=O)NR^xR^y$, —$SO_nR^x$ and —$SO_nNR^xR^y$.

The term "carbonyl," as used herein, refers to "C(=O)".

The terms "acyl," "carboxyl group," or "carbonyl group" are recognized in the art and can include such moieties as can be represented by the general formula:

wherein W is $OR^w$, $N(R^w)_2$, $SR^w$, or $R^w$, $R^w$ being hydrogen, alkyl, heteroalkyl, alkenyl, heteroalkenyl, alkynyl, heteroalkynyl, aryl, heteroaryl, heterocycle, substituted derivatives thereof, or a salt thereof. For example, when W is O-alkyl, the formula represents an "ester," and when W is OH, the formula represents a "carboxylic acid." When W is alkyl, the formula represents a "ketone" group, and when W is hydrogen, the formula represents an "aldehyde" group. Those of ordinary skill in the art will understand the use of such terms.

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic, fused, and bridged substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Other than in the operating examples, or where otherwise indicated, all numbers expressing quantities of ingredients or reaction conditions used herein should be understood as modified in all instances by the term "about." The term "about" when used in connection with percentages can mean±1%.

The term "statistically significant" or "significantly" refers to statistical significance and generally means a two standard deviation (2SD) difference, above or below a reference value. Additional definitions are provided in the text of individual sections below.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); The ELISA guidebook (Methods in molecular biology 149) by Crowther J. R. (2000); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001) and Davis et al., Basic Methods in Molecular Biology, Elsevier Science Publishing, Inc., New York, USA (1995) which are both incorporated by reference herein in their entireties.

Other terms are defined herein within the description of the various aspects of the invention.

The methods and compositions described herein relate to the treatment of cancer by inhibiting the activity of sterol regulatory binding protein 1 (SREBP1). As used herein, "sterol regulatory binding protein 1" or "SREBP1" (e.g. NCBI Gene ID: 6720) refers to a transcription factor involved in the regulation of lipid homeostasis which is synthesized as an inactive precursor bound to the endoplasmic reticulum and upon a decrease in cellular sterol levels, undergoes a sequential two-step cleavage process to release the NH2-terminal active domain in the nucleus (designated nSREBPs), and then transactivating SREBP target genes to maintain cholesterol and FAs homeostasis. Targets of SREBP1 activity include enzymes required for cholesterol and fatty acids (FAs) synthesis, e.g. FASN and SCD. Two SREBP1 human isoforms exist; SREBP1a (protein: SEQ ID NO: 1; mRNA: SEQ ID NO: 2) and SREBP1c (protein: SEQ ID NO: 3; mRNA: SEQ ID NO: 4). In some embodiments, SREBP1 can refer to SREBP1a and SREBP1c. In some embodiments, SREBP1 can be SREBP1a. In some embodiments, SREBP1 can be SREBP1c. SREBP1 can be expressed at abnormally high levels in certain cancers and is believed to have a correlation with, e.g. malignant transformation, cancer progression, proliferation, and metastasis for several cancer types, particularly hormone-responsive tissues including breast and prostate cancers.

Given the broad range of tumor types which display growth inhibition in response to inhibitors of SREBP1, (e.g. leukemias, CNS cancers, non-small cell lung cancers, prostate cancers, melanomas, colon cancers, ovarian cancers, renal cancers, and breast cancers, as described in Example 3), it is contemplated herein that the inhibitors and methods described herein can treat any cancer comprising cells with increased or high levels of SREBP1 expression and/or activity.

In some embodiments, the technology described herein relates to methods of treating cancer by inhibiting the lipogenesis characteristic of cancer by inhibiting SREBP1. In some embodiments, SREBP1 can be inhibited by administering to a subject an inhibitor of SREBP1. As used herein, the term "inhibitor of SREBP1" or "SREBP1 inhibitor" refers to an agent which reduces the expression and/or activity of SREBP1 by at least 10%, e.g. by 10% or more, 20% or more, 30% or more, 50% or more, 75% or more, 90% or more, 95% or more, 98% or more, or 99% or more. The term "agent" refers generally to any entity which is normally not present or not present at the levels being administered to a cell, tissue or subject. An agent can be selected from a group comprising: polynucleotides; polypeptides; small molecules; antibodies; or functional fragments thereof. In some embodiments, the SREBP1 inhibitor can be a pinacolyl boronate-substituted stilbene.

In some embodiments, the inhibitor of SREBP1 can be a compound having the formula of I, II, III or IV, wherein formulae I, II, III, and IV are:

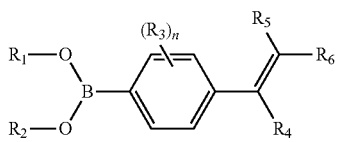

I wherein $R_1$ and $R_2$ are unsubstituted branched or straight chain alkyl, and $R_1$ and $R_2$ can be taken together to form a substituted or unsubstituted five or six membered ring;

$R_3$ is halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $—C(=O)R^B$; $—CO_2R^B$; —; —CN; —SCN; $—SR^B$; $—SOR^B$; $—SO_2R^B$; $—NO_2$; $—N(R^B)_2$; $—NHC(O)R^B$; or $—C(R^B)_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

$R_4$ and $R_5$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —CN; halogen; or hydroxyl;

$R_6$ is cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl;

$R_7$ are independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $—C(=O)R^B$; $—CO_2R^B$; —; —CN; —SCN; $—SR^B$; $—SOR^B$; $—SO_2R^B$; $—NO_2$; $—N(R^B)_2$; $—NHC(O)R^B$; or $—C(R^B)_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

n is an integer 0-4 inclusive; and m is an integer 0-5 inclusive;

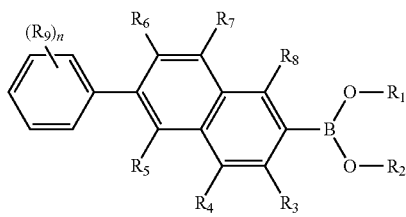

II wherein $R_1$ and $R_2$ are unsubstituted branched or straight chain alkyl, and $R_1$ and $R_2$ can be taken together to form a substituted or unsubstituted five or six membered ring;

$R_3$, $R_4$, $R_5$, $R_6$, $R_7$ and $R_8$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $B(O)R_1R_2$; $—C(=O)R^B$; $—CO_2R^B$; —; —CN; —SCN; $—SR^B$; $—SOR^B$; $—SO_2R^B$; $—NO_2$; $—N(R^B)_2$; $—NHC(O)R^B$; or $—C(R^B)_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

$R_9$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $—C(=O)R^B$; $—CO_2R^B$; —; —CN; —SCN; $—SR^B$; $—SOR^B$; $—SO_2R^B$; $—NO_2$; $—N(R^B)_2$; $—NHC(O)R^B$; or $—C(R^B)_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo; and wherein $R_9$ and $R_5$ or $R_6$ can be taken together to form a substituted or unsubstituted five or six membered ring; and n is an integer 0 to 5, inclusive;

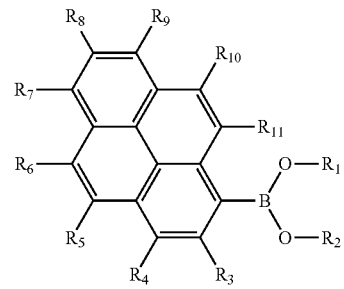

III wherein $R_1$ and $R_2$ are unsubstituted branched or straight chain alkyl, and $R_1$ and $R_2$ can be taken together to form a substituted or unsubstituted five or six membered ring; and $R_3$, $R_4$, $R_5$, $R_6$, $R_7$, $R_8$, $R_9$, $R_{10}$ and $R_{11}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $B(O)R_1R_2$; $—C(=O)R^B$; $—CO_2R^B$; —; —CN; —SCN; $—SR^B$; $—SOR^B$; $—SO_2R^B$; $—NO_2$; $—N(R^B)_2$; $—NHC(O)R^B$; or $—C(R^B)_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

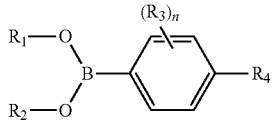

IV wherein $R_1$ and $R_2$ are unsubstituted branched or straight chain alkyl, and $R_1$ and $R_2$ can be taken together to form a substituted or unsubstituted five or six membered ring;

$R_3$ halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

$R_4$ is optionally substituted aryl, or optionally substituted heteroaryl; and n is an integer 0-4 inclusive.

In some embodiments, provided herein are SREBP1 inhibitors of formula I:

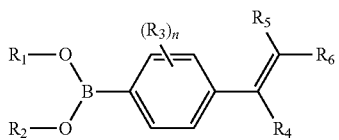

I wherein $R_1$ and $R_2$ are unsubstituted branched or straight chain alkyl, and $R_1$ and $R_2$ can be taken together to form a substituted or unsubstituted five or six membered ring;

$R_3$ is halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

$R_4$ and $R_5$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —CN; halogen; or hydroxyl;

$R_6$ is cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl;

$R_7$ are independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

n is an integer 0-4 inclusive; and m is an integer 0-5 inclusive.

In some embodiments $R_1$ and $R_2$ are the different. In some embodiments, $R_1$ and $R_2$ are the same. In some embodiments, at least $R_1$ or $R_2$ is $C_{1-4}$ alkyl. In some embodiments, both $R_1$ and $R_2$ are methyl, ethyl, propyl, or butyl. In some embodiments $R_1$ and $R_2$ are taken together to form an unsubstituted five membered ring. In some embodiments $R_1$ and $R_2$ are taken together to form a substituted five membered ring. In some embodiments $R_1$ and $R_2$ are taken together to form an unsubstituted six membered ring. In some embodiments $R_1$ and $R_2$ are taken together to form a substituted six membered ring. In some embodiments, $R_1$ and $R_2$ are taken together to form

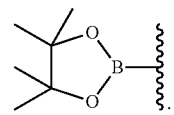 [SMILES: *B1OC(C)(C)C(C)(C)O1]

In some embodiments, $R_3$ and $R_6$ are independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

In some embodiments, n is 0. In some embodiments, n is 1. In some embodiments, n is 2. In some embodiments, n is 3. In some embodiments, n is 4.

In some embodiments, all $R_3$ are different. In some embodiments, all $R_3$ are the same. In some embodiments, at least two $R_3$ are the same. In some embodiments, at least three $R_3$ are the same. In some embodiments, at least one $R_3$ is $C_{1-4}$ alkyl. In some embodiments, at least one $R_3$ is $C_{2-4}$ alkenyl. In some embodiments, at least one $R_3$ is $C_{2-4}$ alkynyl. In some embodiments, at least one $R_3$ is $C_{1-4}$ alkoxy. In some embodiments, at least one $R_3$ is CN. In some embodiments, at least one $R_3$ is halogen. In some embodiments, at least one $R_3$ is F, Cl, Br, or I. In some embodiments, at least one $R_3$ is $CF_3$. In some embodiments, at least one $R_3$ is $NO_2$. In some embodiments, at least one $R_3$ is substituted aryl. In some embodiments, at least one $R_3$ is unsubstituted aryl. In some embodiments, at least one $R_3$ is substituted phenyl. In some embodiments, at least one $R_3$ is unsubstituted phenyl.

In some embodiments, $R_4$ and $R_5$ are independently hydrogen, —CN, halogen, hydroxyl, alkoxy, aryloxy, alkylthioxy, arylthioxy, amino, alkylamino, dialkylamino, heteroaryloxy, heteroarylthioxy, or alkylhalo. In some embodiments, $R_4$ and $R_5$ are the same. In some embodiments, $R_4$ and $R_5$ are different. In some embodiments, at least $R_4$ is hydrogen. In some embodiments, at least $R_5$ is hydrogen. In some embodiments, both $R_4$ and $R_5$ are hydrogen. In some embodiments, $R_4$ is $C_{1-4}$ alkyl. In some embodiments, $R_4$ is $C_{2-4}$ alkenyl. In some embodiments, $R_4$ is $C_{2-4}$ alkynyl. In some embodiments, $R_4$ is CN. In some embodiments, $R_4$ is substituted aryl. In some embodiments, $R_4$ is unsubstituted aryl. In some embodiments, $R_4$ is substituted phenyl. In some embodiments, $R_4$ is unsubstituted phenyl. In some embodiments, $R_5$ is $C_{1-4}$ alkyl. In some embodiments, $R_5$ is $C_{2-4}$ alkenyl. In some embodiments, $R_5$ is $C_{2-4}$ alkynyl. In some embodiments, $R_5$ is CN. In some embodiments, $R_5$ is substituted aryl. In some embodiments, $R_5$ is unsubstituted aryl. In some embodiments, $R_5$ is substituted phenyl. In some embodiments, $R_5$ is unsubstituted phenyl. In some embodiments, $R_4$ is CN and $R_5$ is phenyl.

In some embodiments, $R_6$ is $C_{1-4}$ alkyl. In some embodiments, $R_6$ is methyl, ethyl, n-propyl, i-propyl, n-butyl, i-butyl or t-butyl. In some embodiments, $R_6$ is $C_{2-4}$ alkenyl. In some embodiments, $R_6$ is $C_{2-4}$ alkynyl. In some embodiments, $R_6$ is substituted or unsubstituted aryl. In some embodiments, $R_6$ is

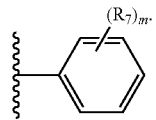

In some embodiments, m is 0. In some embodiments, m is 1. In some embodiments, m is 2. In some embodiments, m is 3. In some embodiments, m is 4. In some embodiments, m is 5.

In some embodiments, all $R_7$ are different. In some embodiments, all $R_7$ are the same. In some embodiments, at least two $R_7$ are the same. In some embodiments, at least three $R_7$ are the same. In some embodiments, at least one $R_7$ is $C_{1-4}$ alkyl. In some embodiments, at least one $R_7$ is $C_{2-4}$ alkenyl. In some embodiments, at least one $R_7$ is $C_{2-4}$ alkynyl. In some embodiments, at least one $R_7$ is $C_{1-4}$ alkoxy. In some embodiments, at least one $R_7$ is CN. In some embodiments, at least one $R_7$ is halogen. In some embodiments, at least one $R_7$ is F, Cl, Br, or I. In some embodiments, at least one $R_7$ is $CF_3$. In some embodiments, at least one $R_7$ is $NO_2$. In some embodiments, at least two $R_7$ are $NO_2$. In some embodiments, at least three $R_7$ are $NO_2$. In some embodiments, at least one $R_7$ is substituted aryl. In some embodiments, at least one $R_7$ is unsubstituted aryl. In some embodiments, at least one $R_7$ is substituted phenyl. In some embodiments, at least one $R_7$ is unsubstituted phenyl. In some embodiments, $R_7$ is OH-phenyl.

In some embodiments, formula I can be

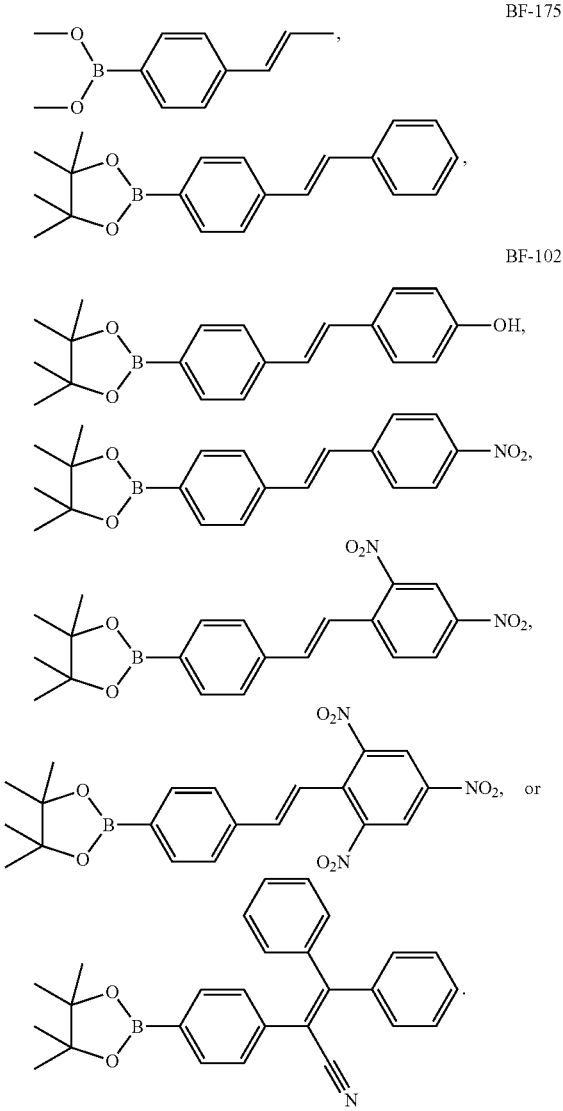

In some embodiments, provided herein are SREBP1 inhibitors of formula II:

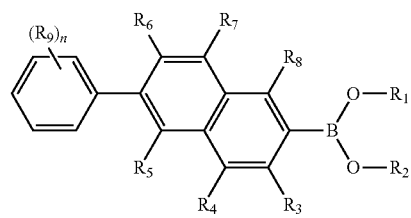

wherein $R_1$ and $R_2$ are unsubstituted branched or straight chain alkyl, and $R_1$ and $R_2$ can be taken together to form a substituted or unsubstituted five or six membered ring;

$R_3$, $R_4$, $R_5$, $R_6$, $R_7$ and $R_8$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $B(O)R_1R_2$; —$C(=O)R^B$; —$CO_2R^B$; —; —CN; —SCN; —$SR^B$; —$SOR^B$; —$SO_2R^B$; —$NO_2$; —$N(R^B)_2$; —$NHC(O)R^B$; or —$C(R^B)_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

$R_9$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$C(=O)R^B$; —$CO_2R^B$; —; —CN; —SCN; —$SR^B$; —$SOR^B$; —$SO_2R^B$; —$NO_2$; —$N(R^B)_2$; —$NHC(O)R^B$; or —$C(R^B)_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo; and wherein $R_9$ and $R_5$ or $R_6$ can be taken together to form a substituted or unsubstituted five or six membered ring; and n is an integer 0 to 5, inclusive.

In some embodiments $R_1$ and $R_2$ are the different. In some embodiments, $R_1$ and $R_2$ are the same. In some embodiments, at least $R_1$ or $R_2$ is $C_{1-4}$ alkyl. In some embodiments, both $R_1$ and $R_2$ are methyl, ethyl, propyl, or butyl. In some embodiments $R_1$ and $R_2$ are taken together to form an unsubstituted five membered ring. In some embodiments $R_1$ and $R_2$ are taken together to form a substituted five membered ring. In some embodiments $R_1$ and $R_2$ are taken together to form an unsubstituted six membered ring. In some embodiments $R_1$ and $R_2$ are taken together to form a substituted six membered ring. In some embodiments, $R_1$ and $R_2$ are taken together to form

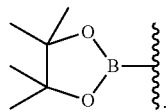 [SMILES: *B1OC(C)(C)C(C)(C)O1]

In some embodiments, $R_1$ and $R_2$ are taken together to form

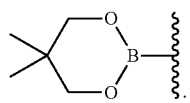

In some embodiments, each one of $R_3$, $R_4$, $R_5$, $R_6$, $R_7$ and $R_8$ are different. In some embodiments, all of $R_3$, $R_4$, $R_5$, $R_6$, $R_7$ and $R_8$ are the same. In some embodiments, at least two of $R_3$, $R_4$, $R_5$, $R_6$, $R_7$ and $R_8$ are the same. In some embodiments, at least three of $R_3$, $R_4$, $R_5$, $R_6$, $R_7$ and $R_8$ are the same. In some embodiments, at least four of $R_3$, $R_4$, $R_5$, $R_6$, $R_7$, $R_8$, $R_9$, $R_{10}$ and $R_{11}$ are the same. In some embodiments, at least five of $R_3$, $R_4$, $R_5$, $R_6$, $R_7$ and $R_8$ are the same. In some embodiments, at least one of $R_3$, $R_4$, $R_5$, $R_6$, $R_7$ and $R_8$ is hydrogen. In some embodiments, each one of $R_3$, $R_4$, $R_5$, $R_6$, $R_7$ and $R_8$ is hydrogen. In some embodiments, at least one $R_3$, $R_4$, $R_5$, $R_6$, $R_7$ and $R_8$ is $C_{1-4}$ alkyl. In some embodiments, at least one $R_3$, $R_4$, $R_5$, $R_6$, $R_7$ and $R_8$ is methyl, ethyl, n-propyl, i-propyl, n-butyl, i-butyl, or t-butyl. In some embodiments, at least one of $R_3$, $R_4$, $R_5$, $R_6$, $R_7$ and $R_8$ is $C_{2-4}$ alkenyl. In some embodiments, at least one $R_3$, $R_4$, $R_5$, $R_6$, $R_7$ and $R_8$ is $C_{2-4}$ alkynyl. In some embodiments, at least one $R_3$, $R_4$, $R_5$, $R_6$, $R_7$ and R is $C_{1-4}$ alkoxy. In some embodiments, at least one $R_3$, $R_4$, $R_5$, $R_6$, $R_7$ and $R_8$ is CN. In some embodiments, at least one $R_3$, $R_4$, $R_5$, $R_6$, $R_7$ and $R_8$ is halogen. In some embodiments, at least one $R_3$, $R_4$, $R_5$, $R_6$, $R_7$ and $R_8$ is F, Cl, Br, or I. In some embodiments, at least one $R_3$, $R_4$, $R_5$, $R_6$, $R_7$ and $R_8$ is $CF_3$. In some embodiments, at least one $R_3$, $R_4$, $R_5$, $R_6$, $R_7$ and $R_8$ is $NO_2$. In some embodiments, at least one $R_3$, $R_4$, $R_5$, $R_6$, $R_7$ and $R_8$ is substituted aryl. In some embodiments, at least one $R_3$, $R_4$, $R_5$, $R_6$, $R_7$ and $R_8$ is unsubstituted aryl. In some embodiments, at least one $R_3$, $R_4$, $R_5$, $R_6$, $R_7$ and $R_8$ is substituted phenyl. In some embodiments, at least one $R_3$, $R_4$, $R_5$, $R_6$, $R_7$ and $R_8$ unsubstituted phenyl. In some embodiments, at least one $R_3$, $R_4$, $R_5$, $R_6$, $R_7$ and $R_8$ is $B(O)R_1R_2$.

In some embodiments, n is 0. In some embodiments, n is 1. In some embodiments, n is 2. In some embodiments, n is 3. In some embodiments, n is 4.

In some embodiments, all $R_9$ are different. In some embodiments, all $R_9$ are the same. In some embodiments, at least two $R_9$ are the same. In some embodiments, at least three $R_9$ are the same. In some embodiments, at least one $R_9$ is $C_{1-4}$ alkyl. In some embodiments, at least one $R_9$ is methyl, ethyl, n-propyl, i-propyl, n-butyl, i-butyl, or t-butyl. In some embodiments, at least one $R_9$ is $C_{2-4}$ alkenyl. In some embodiments, at least one $R_9$ is $C_{2-4}$ alkynyl. In some embodiments, at least one $R_9$ is $C_{1-6}$ alkoxy. In some embodiments, at least one $R_9$ is $C_{1-6}$ alcohol. In some embodiments, at least one $R_9$ is $C_{1-6}$ diol. In some embodiments, at least one $R_9$ is O—$C_{1-6}$ alcohol. In some embodiments, at least one $R_9$ is O—$C_{1-6}$ diol. In some embodiments, at least one $R_9$ is a substituted or unsubstituted cyclic aliphatic. In some embodiments, at least one $R_9$ is a monocyclic. In some embodiments, at least one $R_9$ is a bicyclic. In some embodiments, at least one $R_9$ is a tricyclic. In some embodiments, at least on $R_9$ is a six membered ring system. In some embodiments, at least one $R_9$ is a seven membered ring system. In some embodiments, at least on $R_9$ is an eight membered ring system. In some embodiments, at least on $R_9$ is a nine membered ring system. In some embodiments, at least on $R_9$ is a ten membered ring system. In some embodiments, at least on $R_9$ is an eleven membered ring system. In some embodiments, at least on $R_9$ is a twelve membered ring system. In some embodiments, at least one $R_9$ is S—$C_{1-12}$ alkyl. In some embodiments, at least one $R_9$ is S—$C_{1-12}$ alkyl, wherein $C_{1-12}$ alkyl is a monocyclic, bicyclic, or tricyclic ring system. In some embodiments, at least one $R_9$ is CN. In some embodiments, at least one $R_9$ is halogen. In some embodiments, at least one $R_9$ is F, Cl, Br, or I. In some embodiments, at least one $R_9$ is $CF_3$. In some embodiments, at least one $R_9$ is $NO_2$. In some embodiments, at least one $R_9$ is substituted aryl. In some embodiments, at least one $R_9$ is unsubstituted aryl. In some embodiments, at least one $R_9$ is substituted phenyl. In some embodiments, at least one $R_9$ is unsubstituted phenyl.

In some embodiments, $R_9$ is at the ortho position. In some embodiments, $R_9$ is at the meta position. In some embodiments, $R_9$ is at the para position. In some embodiments, one $R_9$ is at the meta position and one $R_9$ is at the para position. In some embodiments, one $R_9$ is at the ortho position and one $R_9$ is at the para position. In some embodiments, one $R_9$ is at the ortho position, one $R_9$ is at the meta position, and one $R_9$ is at the para position.

In some embodiments, formula II can be

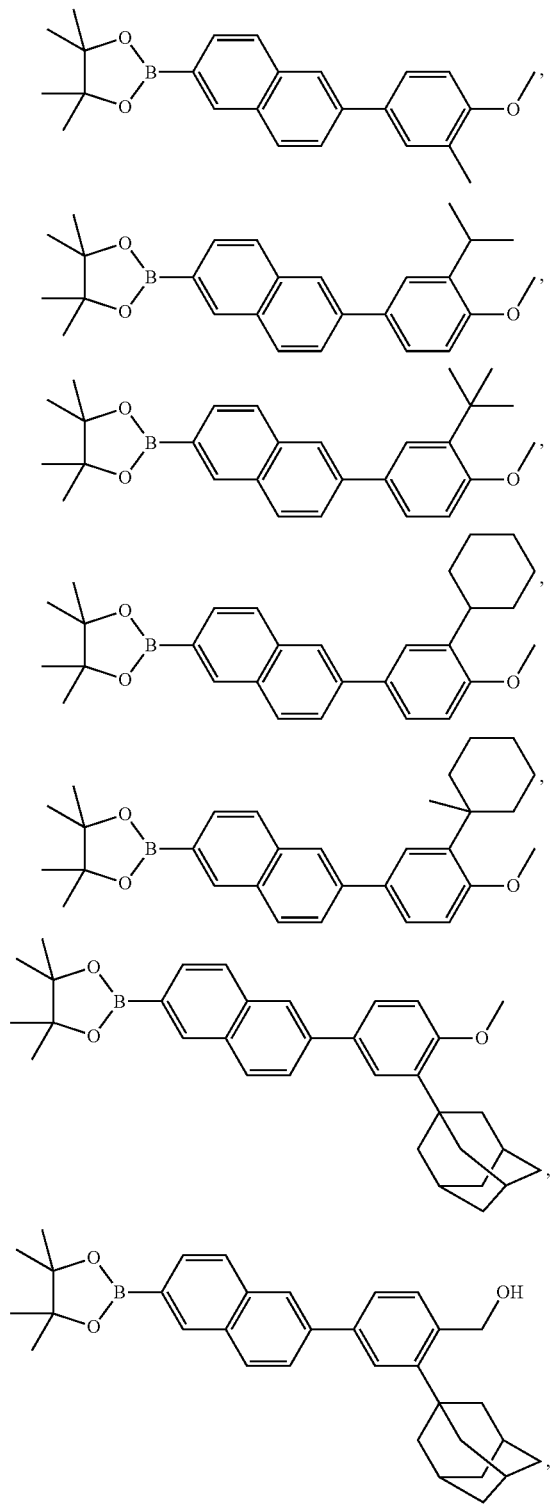

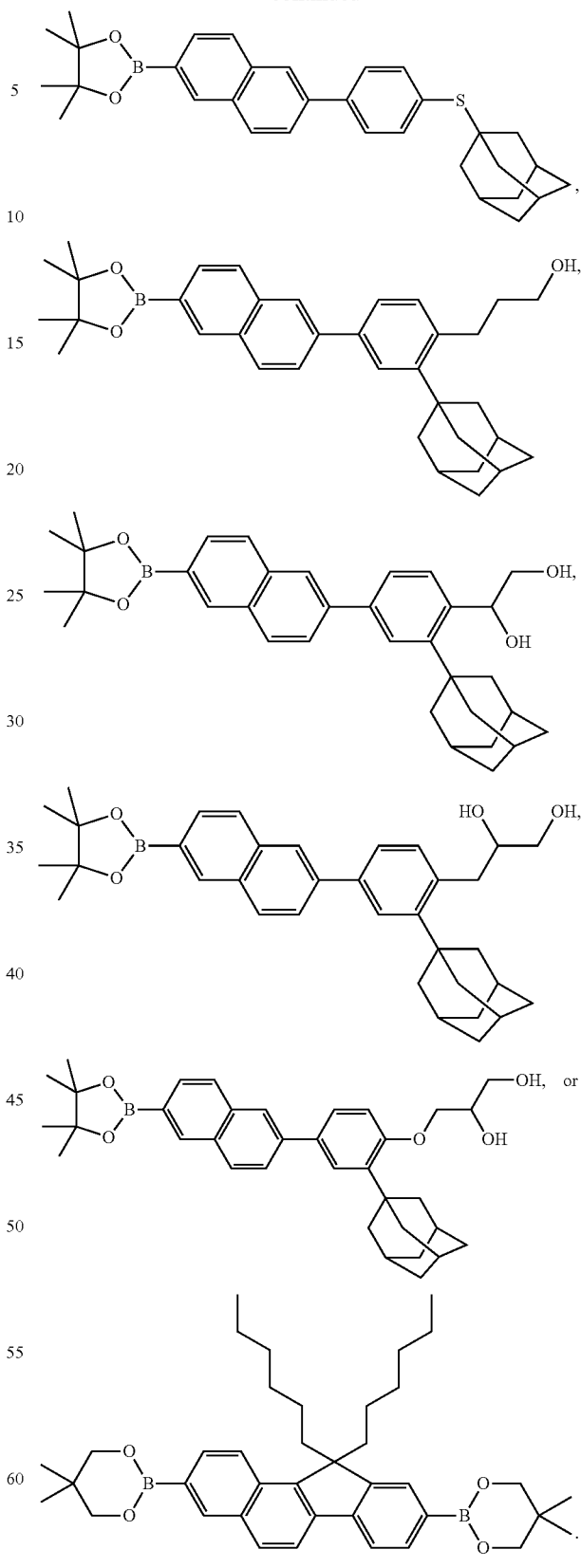

In some embodiments, provided herein are SREBP1 inhibitors of formula III:

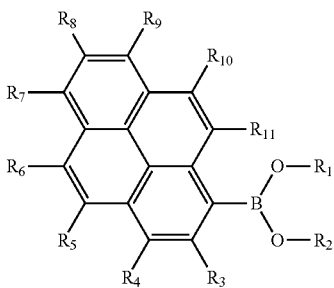

wherein $R_1$ and $R_2$ are unsubstituted branched or straight chain alkyl, and $R_1$ and $R_2$ can be taken together to form a substituted or unsubstituted five or six membered ring; and $R_3$, $R_4$, $R_5$, $R_6$, $R_7$, $R_8$, $R_9$, $R_{10}$ and $R_{11}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $B(O)R_1R_2$; $—C(=O)R^B$; $—CO_2R^B$; $—$; $—CN$; $—SCN$; $—SR^B$; $—SOR^B$; $—SO_2R^B$; $—NO_2$; $—N(R^B)_2$; $—NHC(O)R^B$; or $—C(R^B)_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo.

In some embodiments $R_1$ and $R_2$ are the different. In some embodiments, $R_1$ and $R_2$ are the same. In some embodiments, at least $R_1$ or $R_2$ is $C_{1-4}$ alkyl. In some embodiments, both $R_1$ and $R_2$ are methyl, ethyl, propyl, or butyl. In some embodiments $R_1$ and $R_2$ are taken together to form an unsubstituted five membered ring. In some embodiments $R_1$ and $R_2$ are taken together to form a substituted five membered ring. In some embodiments $R_1$ and $R_2$ are taken together to form an unsubstituted six membered ring. In some embodiments $R_1$ and $R_2$ are taken together to form a substituted six membered ring. In some embodiments, $R_1$ and $R_2$ are taken together to form

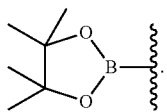 [SMILES: *B1OC(C)(C)C(C)(C)O1]

In some embodiments, each one of $R_3$, $R_4$, $R_5$, $R_6$, $R_7$, $R_8$, $R_9$, $R_{10}$ and $R_{11}$ are different. In some embodiments, all of $R_3$, $R_4$, $R_5$, $R_6$, $R_7$, $R_8$, $R_9$, $R_{10}$ and $R_{11}$ are the same. In some embodiments, at least two of $R_3$, $R_4$, $R_5$, $R_6$, $R_7$, $R_8$, $R_9$, $R_{10}$ and $R_{11}$ are the same. In some embodiments, at least three of $R_3$, $R_4$, $R_5$, $R_6$, $R_7$, $R_8$, $R_9$, $R_{10}$ and $R_{11}$ are the same. In some embodiments, at least four of $R_3$, $R_4$, $R_5$, $R_6$, $R_7$, $R_8$, $R_9$, $R_{10}$ and $R_{11}$ are the same. In some embodiments, at least five of $R_3$, $R_4$, $R_5$, $R_6$, $R_7$, $R_8$, $R_9$, $R_{10}$ and $R_{11}$ are the same. In some embodiments, at least six of $R_3$, $R_4$, $R_5$, $R_6$, $R_7$, $R_8$, $R_9$, $R_{10}$ and $R_{11}$ are the same. In some embodiments, at least seven of $R_3$, $R_4$, $R_5$, $R_6$, $R_7$, $R_8$, $R_9$, $R_{10}$ and $R_{11}$ are the same. In some embodiments, at least one of $R_3$, $R_4$, $R_5$, $R_6$, $R_7$, $R_8$, $R_9$, $R_{10}$ and $R_{11}$ is hydrogen. In some embodiments, each one of $R_3$, $R_4$, $R_5$, $R_6$, $R_7$, $R_8$, $R_9$, $R_{10}$ and $R_{11}$ is hydrogen.

In some embodiments, at least one $R_3$, $R_4$, $R_5$, $R_6$, $R_7$, $R_8$, $R_9$, $R_{10}$ and $R_{11}$ is $C_{1-4}$ alkyl. In some embodiments, at least one $R_3$, $R_4$, $R_5$, $R_6$, $R_7$, $R_8$, $R_9$, $R_{10}$ and $R_{11}$ is methyl, ethyl, n-propyl, i-propyl, n-butyl, i-butyl, or t-butyl. In some embodiments, at least one of $R_3$, $R_4$, $R_5$, $R_6$, $R_7$, $R_8$, $R_9$, $R_{10}$ and $R_{11}$ is $C_{2-4}$ alkenyl. In some embodiments, at least one $R_3$, $R_4$, $R_5$, $R_6$, $R_7$, $R_8$, $R_9$, $R_{10}$ and $R_{11}$ is $C_{2-4}$ alkynyl. In some embodiments, at least one $R_3$, $R_4$, $R_5$, $R_6$, $R_7$, $R_8$, $R_9$, $R_{10}$ and $R_{11}$ is $C_{1-4}$ alkoxy. In some embodiments, at least one $R_3$, $R_4$, $R_5$, $R_6$, $R_7$, $R_8$, $R_9$, $R_{10}$ and $R_{11}$ is CN. In some embodiments, at least one $R_3$, $R_4$, $R_5$, $R_6$, $R_7$, $R_8$, $R_9$, $R_{10}$ and $R_{11}$ is halogen. In some embodiments, at least one $R_3$, $R_4$, $R_5$, $R_6$, $R_7$, $R_8$, $R_9$, $R_{10}$ and $R_{11}$ is F, Cl, Br, or I. In some embodiments, at least one $R_3$, $R_4$, $R_5$, $R_6$, $R_7$, $R_8$, $R_9$, $R_{10}$ and $R_{11}$ is $CF_3$. In some embodiments, at least one $R_3$, $R_4$, $R_5$, $R_6$, $R_7$, $R_8$, $R_9$, $R_{10}$ and $R_{11}$ is $NO_2$. In some embodiments, at least one $R_3$, $R_4$, $R_5$, $R_6$, $R_7$, $R_8$, $R_9$, $R_{10}$ and $R_{11}$ is substituted aryl. In some embodiments, at least one $R_3$, $R_4$, $R_5$, $R_6$, $R_9$, $R_8$, $R_9$, $R_{10}$ and $R_{11}$ is unsubstituted aryl. In some embodiments, at least one $R_3$, $R_4$, $R_5$, $R_6$, $R_7$, $R_8$, $R_9$, $R_{10}$ and $R_{11}$ is substituted phenyl. In some embodiments, at least one $R_3$, $R_4$, $R_5$, $R_6$, $R_7$, $R_8$, $R_9$, $R_{10}$ and $R_{11}$ unsubstituted phenyl. In some embodiments, at least one $R_3$, $R_4$, $R_5$, $R_6$, $R_7$, $R_8$, $R_9$, $R_{10}$ and $R_{11}$ is $B(O)R_1R_2$.

In some embodiments, formula III can be

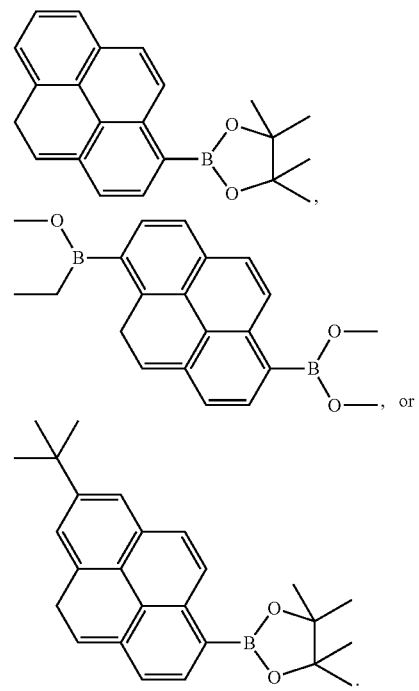

In some embodiments, provided herein are SREBP1 inhibitors of formula IV:

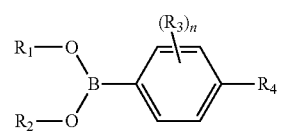

IV wherein $R_1$ and $R_2$ are unsubstituted branched or straight chain alkyl, and $R_1$ and $R_2$ can be taken together to form a substituted or unsubstituted five or six membered ring;

$R_3$ halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

$R_4$ is optionally substituted aryl, or optionally substituted heteroaryl; and n is an integer 0-4 inclusive.

In some embodiments $R_1$ and $R_2$ are the different. In some embodiments, $R_1$ and $R_2$ are the same. In some embodiments, at least $R_1$ or $R_2$ is $C_{1-4}$ alkyl. In some embodiments, both $R_1$ and $R_2$ are methyl, ethyl, propyl, or butyl. In some embodiments $R_1$ and $R_2$ are taken together to form an unsubstituted five membered ring. In some embodiments $R_1$ and $R_2$ are taken together to form a substituted five membered ring. In some embodiments $R_1$ and $R_2$ are taken together to form an unsubstituted six membered ring. In some embodiments $R_1$ and $R_2$ are taken together to form a substituted six membered ring. In some embodiments, $R_1$ and $R_2$ are taken together to form

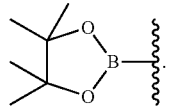 [SMILES: *B1OC(C)(C)C(C)(C)O1]

In some embodiments, $R_3$ is halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

In some embodiments, n is 0. In some embodiments, n is 1. In some embodiments, n is 2. In some embodiments, n is 3. In some embodiments, n is 4.

In some embodiments, all $R_3$ are different. In some embodiments, all $R_3$ are the same. In some embodiments, at least two $R_3$ are the same. In some embodiments, at least three $R_3$ are the same. In some embodiments, at least one $R_3$ is $C_{1-4}$ alkyl. In some embodiments, at least one $R_3$ is $C_{2-4}$ alkenyl. In some embodiments, at least one $R_3$ is $C_{2-4}$ alkynyl. In some embodiments, at least one $R_3$ is $C_{1-4}$ alkoxy. In some embodiments, at least one $R_3$ is CN. In some embodiments, at least one $R_3$ is halogen. In some embodiments, at least one $R_3$ is F, Cl, Br, or I. In some embodiments, at least one $R_3$ is $CF_3$. In some embodiments, at least one $R_3$ is $NO_2$. In some embodiments, at least one $R_3$ is substituted aryl. In some embodiments, at least one $R_3$ is unsubstituted aryl. In some embodiments, at least one $R_3$ is substituted phenyl. In some embodiments, at least one $R_3$ is unsubstituted phenyl.

In some embodiments, $R_4$ is unsubstituted aryl. In some embodiments, $R_2$ is substituted aryl. In some embodiments, $R_4$ is substituted or unsubstituted monocyclic aryl. In some embodiments, $R_4$ is substituted or unsubstituted bicyclic aryl. In some embodiments, $R_4$ is substituted or unsubstituted tricyclic aryl. In some embodiments, $R_4$ is unsubstituted heteroaryl. In some embodiments, $R_2$ is substituted heteroaryl. In some embodiments, $R_4$ is substituted or unsubstituted monocyclic heteroaryl. In some embodiments, $R_4$ is substituted or unsubstituted bicyclic heteroaryl. In some embodiments, $R_4$ is substituted or unsubstituted tricyclic heteroaryl. Is some embodiments, $R_4$ is

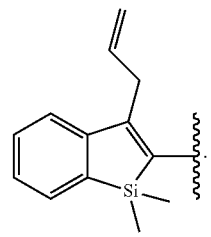 [SMILES: *C1=C(CC=C)c2ccccc2[Si]1(C)C]

In some embodiments, $R_4$ is substituted. In some embodiments, $R_4$ is substituted at more than one position. In some embodiments, $R_4$ is substituted with $C_{1-4}$ alkyl. In some embodiments, $R_4$ is substituted with $C_{2-4}$ alkenyl. In some embodiments, $R_4$ is substituted with $C_{2-4}$ alkynyl. In some embodiments, $R_4$ is substituted with $C_{1-4}$ alkoxy. In some embodiments, $R_4$ is substituted with CN. In some embodiments, $R_4$ is substituted with halogen. In some embodiments, $R_4$ is substituted with F, Cl, Br, or I. In some embodiments, $R_4$ is substituted with $CF_3$. In some embodiments, $R_4$ is substituted with $NO_2$. In some embodiments, $R_4$ is substituted with substituted aryl. In some embodiments, $R_4$ is substituted with unsubstituted aryl.

In some embodiments, formula IV can be

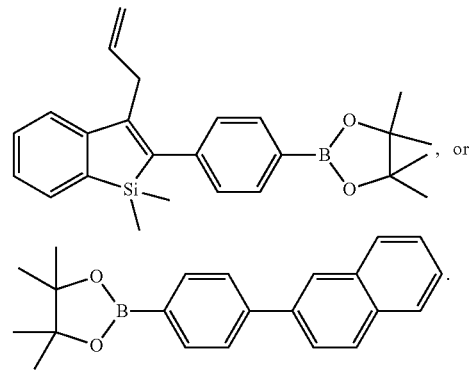

Whether a given compound reduces the expression and/or activity of SREBP1 can be determined in vitro or in vivo, e.g. in in vitro assays or in an animal model of, for example, breast cancer. Methods of determining the expression of SREBP1 are described below herein. A non-limiting example can be immunohistochemical analysis of tumor tissue as described in the Examples herein. Briefly, 5-μm thick sections of tumor tissue are de-paraffinized with xylene and rehydrated through a graded alcohol series. Endogenous peroxidase activity can be blocked by incubation in a 3% hydrogen peroxide solution for 15 minutes. Antigen retrieval can be carried out by immersing the slides in 10 mM sodium citrate buffer (pH 6.0) and maintaining them at a sub-boiling temperature for 5 minutes. The slides can be rinsed in phosphate-buffered saline and incubated with 10% normal serum to block non-specific staining. The slides can then be incubated with the primary antibody (anti-SREBP1, K-10, Santa Cruz) overnight at 4° C. in a humidified chamber. Staining can be assessed e.g., using a semi-quantitative method such as, e.g., the German semi-quantitative scoring system as described in the Examples herein. Where SREBP1 is a transcription factor, its activity can be determined by monitoring the activity of one or more genes that is transactivates, e.g., ACLY and SCD1 or FASN. SREPB1 target gene expression can be monitored, e.g. via RT-PCR or at the protein level, e.g. by Western blot of other immuno-chemical approaches. Alternatively, the promoters for these SREBP1 target genes (or other target genes) can be ligated to a reporter gene, e.g. GFP, to provide a read-out in cultured cells for SREBP1 activity under given conditions. In some embodiments, if SREBP1 activity is decreased, expression of both SREBP1 isoforms, SREBP2, ACLY, and SCD1 will be decreased, while FASN expression will be decreased to a lesser extent, and PKLR expression will not be altered.

In some embodiments, the methods described herein relate to selecting a subject to be treated for cancer with the inhibitors of SREBP1 described herein. A subject selected for treatment according to the methods described herein should be one having a cancer comprised of cells which are or are likely to be sensitive to the inhibitors of SREBP1 described herein, e.g. a cancer having cells which express abnormal (e.g. high) levels of SREBP1. Whether a cancer is likely to be sensitive to inhibitors of SREBP1 can be determined, for example, by determining whether the cancer cells are of a type of cancer cell that typically express abnormal levels of SREBP1 or by determining if they express abnormal levels of SREBP1.

In some embodiments, the subject can have cancer cells which express abnormal levels of SREBP1. As used herein, the term "abnormal level" of SREBP1 can refer to amounts of SREBP1 expression products and/or activity that are significantly greater than the amounts of SREBP1 expression products and/or activity in a control reference sample representative of the levels of SREBP1 expression products and/or activity in cells of the same type from a healthy individual.

In some embodiments, a subject expressing an abnormal level of SREBP1 can be a subject having a cancer which has an H-score of greater than 1. An H-score can be calculated based upon immunohistochemical staining of a sample of a cancer obtained from a subject and stained as described herein for SREBP1 polypeptide expression. The expression levels of SREBP1 in such clinical specimens can be scored (H-score) based on the total percentage of positive cells and the intensity of the staining (1+, 2+, or 3+), where H= (%"1+"×1)+(%"2+"×2)+(%"3+"×3). A score of 0-1 can be a normal level of SREBP1 expression, while a score of greater than 1 can be an abnormal level of SREBP1 expression, e.g. a score of 1.1 or greater, 1.5 or greater, 2.0 or greater, or 2.5 or greater.

In some embodiments, the control reference sample can comprise healthy cells of the same type as the cells for which SREBP1 levels are to be determined. In some embodiments, the cells of the control reference sample can be of similar age, developmental status, sex, and/or cell type as the cells for which the level of SREBP1 expression and/or activity is to be determined. In some embodiments, the control reference sample can be obtained from a healthy organism of similar age, developmental status, and/or sex as the subject organism for which the level of SREBP1 expression and/or activity is to be determined. In some embodiments, the test sample and control reference sample are of the same type, that is, obtained from the same biological source, and comprising the same composition, e.g. the same number and type of cells. In some embodiments, the control reference sample can be non-cancerous cells from the subject organism which are of the cell type from which the cancerous cells descended, e.g. if the cancerous cells are breast cancer cells, the control reference sample can be healthy breast cells from the same subject.

In some embodiments, a subject is a candidate for treatment according to the methods described herein if the levels of SREBP1 expression products and/or activity in the cells of a subject are significantly greater than the levels of SREBP1 expression products and/or activity present in the control reference sample. In some embodiments, a subject is a candidate for treatment according to the methods described herein if the levels of SREBP1 expression products and/or activity in the cells of a subject are at least 2-fold greater than the levels of SREBP1 expression products and/or activity present in the control reference sample, e.g. 2-fold or greater, 3-fold or greater, 4-fold or greater, 5-fold or greater, or 6-fold or more or greater.

The expression of a given gene can be determined by measuring the level of any of the expression products of that gene, e.g. the mRNA or polypeptide encoded by that gene. In some embodiments, a cell which expresses an abnormal level of a gene can be a cell that expresses an abnormal level of mRNA encoded by that gene. In some embodiments, a cell which expresses an abnormal level of a gene can be a cell that expresses an abnormal level of polypeptide encoded by that gene.

In some embodiments, a cell which expresses an abnormal level of SREBP1 can be a cell that expresses an abnormal level of SREBP1 polypeptide.

The level of expression of, e.g. SREBP1, can be determined by measuring the level of an mRNA and/or a polypeptide encoded by SREBP1 in a biological sample obtained from the subject. In some embodiments, the biological sample comprises cancer cells. In some embodiments, the biological sample comprises a biopsy sample.

Methods for determining the level of an mRNA and/or polypeptide in a subject or a sample obtained from a subject are well known in the art. Methods of determining the level of a SREBP1 polypeptide include, but are not limited to, Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; mass spectroscopy and/or immunoelectrophoresis assay. In certain embodiments determining the level of SREBP1 polypeptide involves the use of an antibody, an antibody fragment, a monoclonal antibody, and/or a monoclonal antibody fragment. Antibodies specific for SREBP1 are commercially available, e.g. Cat. No. 3259 from Abcam; Cambridge, Mass. Methods of determining the level of a SREBP1 mRNA include, but are not limited to RT-PCR, quantitative RT-PCR, hybridization assays, RNA-Seq, Northern blot, high-throughput sequencing, and/or microarray based expression analysis.

When certain genes are expressed at abnormally high levels in a cell, SREBP1 is likely expressed at abnormal levels in the same cell, i.e. there are genes whose expression can serve as a proxy for the direct measurement of SREBP1 expression. Non-limiting examples of such genes include, Erb2 (NCBI Gene ID: 2100, e.g. SEQ ID NO: 05 (mRNA), SEQ ID NO: 06 (protein); FASN (NCBI Gene ID: 2194, e.g. SEQ ID NO: 07 (mRNA), SEQ ID NO: 08 (protein); SCD1 (NCBI Gene ID: 6319, e.g. SEQ ID NO: 09 (mRNA), SEQ ID NO: 10 (protein); or ACLY (NCBI Gene ID: 47, e.g. SEQ ID NO: 11 (mRNA), SEQ ID NO: 12 (protein). In some embodiments, a subject in need of treatment according to the methods described herein can have cancer cells which express abnormal levels of genes which are correlated with expression of abnormal levels of SREBP1. In some embodiments, a subject in need of treatment according the methods described herein can have cancer cells which express abnormal levels of an mRNA of one or more genes correlated with expression of abnormal levels of SREBP1. In some embodiments, a subject in need of treatment according the methods described herein can have cancer cells which express abnormal levels of a polypeptide of one or more genes correlated with expression of abnormal levels of SREBP1. Expression of these genes in the cancer cells of a subject can be determined as described above herein for SREBP1. Antibodies specific for Erb2, FASN, SCD1, and ACLY are commercially available, e.g., respectively, Cat. Nos. ab3576, ab22759, ab19862, and ab40793 from Abcam; Cambridge, Mass.

In some embodiments, determining the expression level of SREBP1 and/or one or more genes correlated with expression of abnormal levels of SREBP1 involves determining the expression of no more than 20 genes, e.g. 20 or fewer genes, 15 or fewer genes, 10 or fewer genes, or 5 or fewer genes.

Certain cancers are known to be characterized and/or likely to be characterized by abnormal expression of SREBP1. Non-limiting examples of such cancers can include endometrial cancer; prostate cancer; breast cancer; colorectal cancer; colorectal carcinoma; hepatocarcinoma; endometrial adenocarcinoma; uterine cancer; leukemia; lung cancer; central nervous system cancer; melanoma; ovarian cancer; renal cancer; and pancreatic cancer. In some embodiments, the subject treated according to the methods described herein can have a cancer likely to be sensitive to the inhibitors of SREBP1 described herein. In some embodiments, the subject selected for treatment according to the methods described herein can have a cancer likely to be sensitive to the inhibitors of SREBP1 described herein. A cancer likely to be sensitive to the inhibitors of SREBP1 described herein can be a type of cancer known to have abnormal expression of SREBP1.

In some embodiments, a cancer treated according to the methods described herein comprises a poorly-differentiated or moderately-differentiated tumor. In some embodiments, a cancer treated according to the methods described herein does not comprise a well-differentiated tumor. The level of differentiation of a tumor can be determined by methods well known to one of skill in the art, e.g. Gleason scores, wherein a Grade 1 tumor is well-differentiated, a Grade 2 tumor is moderately-differentiated, and a Grade 3 or higher tumor is poorly-differentiated (see, e.g. Gleason, Donald F; Mellinger George T. J. Urol. 2002 167:953-8; which is incorporated by reference herein in its entirety).

In some embodiments, the methods described herein relate to treating a subject having or diagnosed as having cancer with a SREBP1 inhibitor. Subjects having cancer can be identified by a physician using current methods of diagnosing cancer. Symptoms and/or complications of cancer which characterize these conditions and aid in diagnosis are well known in the art and include but are not limited to, for example, in the case of breast cancer a lump or mass in the breast tissue, swelling of all or part of a breast, skin irritation, dimpling of the breast, pain in the breast or nipple, nipple retraction, redness, scaliness, or irritation of the breast or nipple, and nipple discharge. Tests that may aid in a diagnosis of, e.g. breast cancer include, but are not limited to, mammograms, x-rays, MRI, ultrasound, ductogram, a biopsy, and ductal lavage. A family history of cancer, or exposure to risk factors for cancer (e.g. smoke, radiation, pollutants, BRCA1 mutation, etc.) can also aid in determining if a subject is likely to have cancer or in making a diagnosis of cancer. The terms "malignancy," "malignant condition," "cancer," or "tumor," as used herein, refer to an uncontrolled growth of cells which interferes with the normal functioning of the bodily organs and systems.

The compositions and methods described herein can be administered to a subject having or diagnosed as having cancer. In some embodiments, the methods described herein comprise administering an effective amount of compositions described herein, e.g. a SREBP1 inhibitor to a subject in order to alleviate a symptom of a cancer. As used herein, "alleviating a symptom of a cancer" is ameliorating any condition or symptom associated with the cancer. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral or parenteral routes, including intravenous, intramuscular, subcutaneous, transdermal, airway (aerosol), pulmonary, or intratumoral. Administration can be local or systemic.

The term "effective amount" as used herein refers to the amount of a SREBP1 inhibitor needed to alleviate at least one or more symptom of the disease or disorder, and relates to a sufficient amount of pharmacological composition to provide the desired effect. The term "therapeutically effective amount" therefore refers to an amount of a SREBP1 inhibitor that is sufficient to cause a particular anti-cancer effect when administered to a typical subject. An effective amount as used herein, in various contexts, would also include an amount sufficient to delay the development of a symptom of the disease, alter the course of a symptom disease (for example but not limited to, slow the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the SREBP1 inhibitor, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for inhibition of SREBP1 activity or for inhibition of cancer cell proliferation, among others. The dosage can be determined by a physician and adjusted, as necessary, to suit observed effects of the treatment.

In certain embodiments, an effective dose of a composition comprising a SREBP1 inhibitor as described herein can be administered to a patient once. In certain embodiments, an effective dose of a composition comprising a SREBP1 inhibitor can be administered to a patient repeatedly. Patients can be administered a therapeutic amount of a composition comprising a SREBP1 inhibitor, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more. A composition comprising a SREBP1 inhibitor can be administered over a period of time, such as over a 5 minute, 10 minute, 15 minute, 20 minute, or 25 minute period. If warranted, the administration can be repeated, for example, on a regular basis, such as hourly for 3 hours, 6 hours, 12 hours or longer or such as biweekly (i.e., every two weeks) for one month, two months, three months, four months or longer. In some instances, after an initial treatment regimen, the treatments can be administered on a less frequent basis. For example, after administration biweekly for three months, administration can be repeated once per month, for six months or a year or longer. Administration of a composition comprising a SREBP1 inhibitor can reduce levels of a marker or symptom of cancer, e.g. the size of a tumor or the rate of growth of a tumor by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the SREBP1 inhibitor.

In some embodiments, the technology described herein relates to a pharmaceutical composition comprising a SREBP1 inhibitor as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, sunflower oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. a SREBP1 inhibitor as described herein.

The methods described herein can further comprise administering a second agent and/or treatment to the subject, e.g. as part of a combinatorial therapy. Non-limiting examples of a second agent and/or treatment can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine;

pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

In some embodiments, the pharmaceutical composition comprising a SREBP1 inhibitor as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of the SREBP1 inhibitor as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a SREBP1 inhibitor as disclosed herein can also be incorporated into the parenteral dosage forms of the disclosure, including conventional and controlled-release parenteral dosage forms.

Pharmaceutical compositions comprising a SREBP1 inhibitor can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

In some embodiments, a SREBP1 inhibitor as described herein can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This invention is further illustrated by the following examples which should not be construed as limiting.

Some embodiments of the technology described herein can be defined according to any of the following numbered paragraphs:

1. A compound of formula I, II, III or IV, wherein formulae I, II III, and IV are:

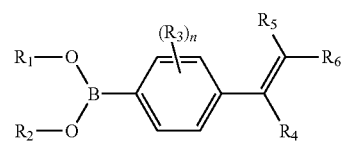

wherein $R_1$ and $R_2$ are unsubstituted branched or straight chain alkyl, and $R_1$ and $R_2$ can be taken together to form a substituted or unsubstituted five or six membered ring;

$R_3$ is halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

$R_4$ and $R_5$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —CN; halogen; or hydroxyl;

$R_6$ is cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl;

$R_7$ are independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy;

arylthioxy; amino; alkylamino; dialkylamino; heteroaryloxy; heteroarylthioxy; or alkylhalo;

n is an integer 0-4 inclusive; and m is an integer 0-5 inclusive;

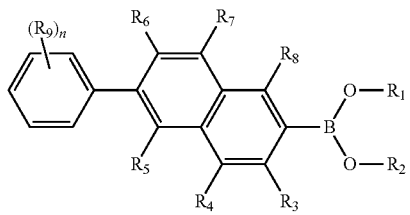

II wherein $R_1$ and $R_2$ are unsubstituted branched or straight chain alkyl, and $R_1$ and $R_2$ can be taken together to form a substituted or unsubstituted five or six membered ring;

$R_3$, $R_4$, $R_5$, $R_6$, $R_7$ and $R_8$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $B(O)R_1R_2$; $—C(=O)R^B$; $—CO_2R^B$; —; $—CN$; $—SCN$; $—SR^B$; $—SOR^B$; $—SO_2R^B$; $—NO_2$; $—N(R^B)_2$; $—NHC(O)R^B$; or $—C(R^B)_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

$R_9$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $—C(=O)R^B$; $—CO_2R^B$; —; $—CN$; $—SCN$; $—SR^B$; $—SOR^B$; $—SO_2R^B$; $—NO_2$; $—N(R^B)_2$; $—NHC(O)R^B$; or $—C(R^B)_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo; and wherein $R_9$ and $R_5$ or $R_6$ can be taken together to form a substituted or unsubstituted five or six membered ring; and n is an integer 0 to 5, inclusive;

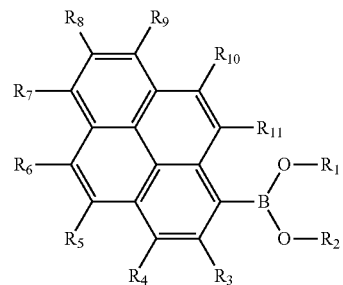

III wherein $R_1$ and $R_2$ are unsubstituted branched or straight chain alkyl, and $R_1$ and $R_2$ can be taken together to form a substituted or unsubstituted five or six membered ring; and $R_3$, $R_4$, $R_5$, $R_6$, $R_7$, $R_8$, $R_9$, $R_{10}$ and $R_{11}$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $B(O)R_1R_2$; $—C(=O)R^B$; $—CO_2R^B$; —; $—CN$; $—SCN$; $—SR^B$; $—SOR^B$; $—SO_2R^B$; $—NO_2$; $—N(R^B)_2$; $—NHC(O)R^B$; or $—C(R^B)_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

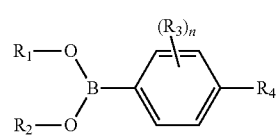

IV wherein $R_1$ and $R_2$ are unsubstituted branched or straight chain alkyl, and $R_1$ and $R_2$ can be taken together to form a substituted or unsubstituted five or six membered ring;

$R_3$ halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $—C(=O)R^B$; $—CO_2R^B$; —; $—CN$; $—SCN$; $—SR^B$; $—SOR^B$; $—SO_2R^B$; $—NO_2$; $—N(R^B)_2$; $—NHC(O)R^B$; or $—C(R^B)_3$; wherein each occurrence of $R^B$ is independently hydrogen; halogen; a protecting group; aliphatic; heteroaliphatic; acyl; aryl moiety; heteroaryl; hydroxyl; alkoxy; aryloxy; alkylthioxy; arylthioxy; amino; alkylamino; dialkylamino; heteroaryloxy; heteroarylthioxy; or alkylhalo;

$R_4$ is optionally substituted aryl, or optionally substituted heteroaryl; and n is an integer 0-4 inclusive.

2. A compound of paragraph 1, wherein the compound is selected from the group consisting of:
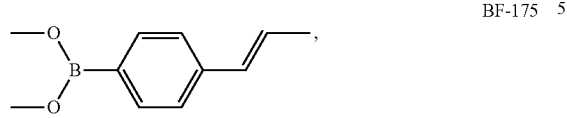
BF-175
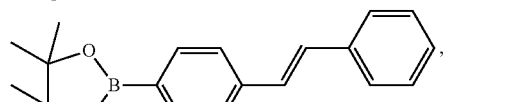
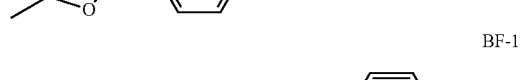
BF-102
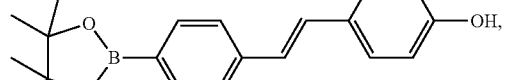
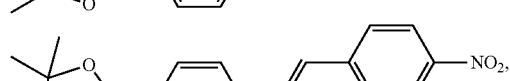
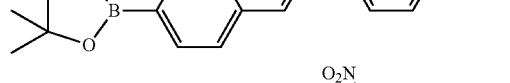
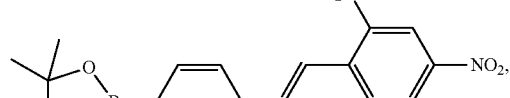
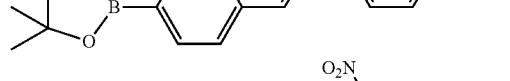
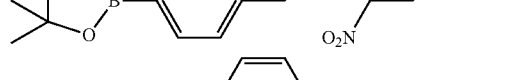
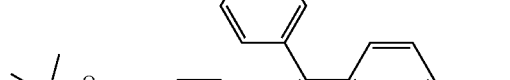
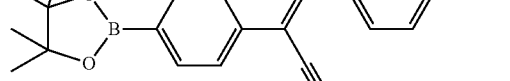
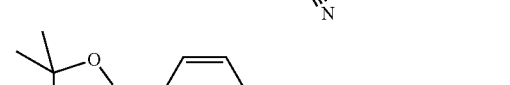
-continued
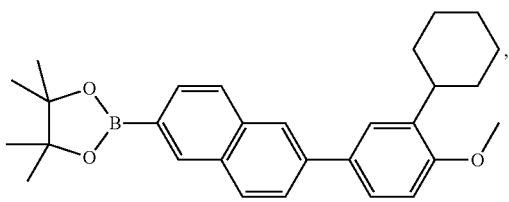
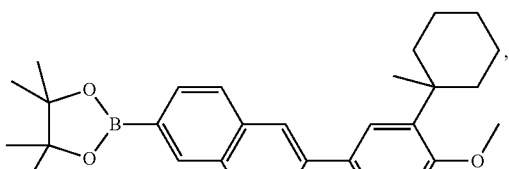
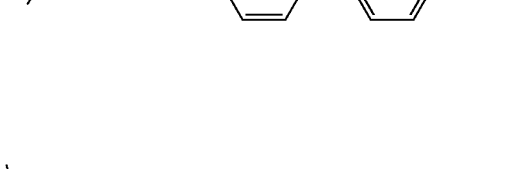
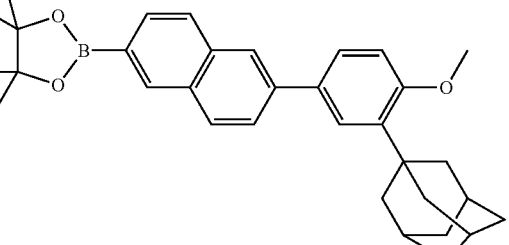
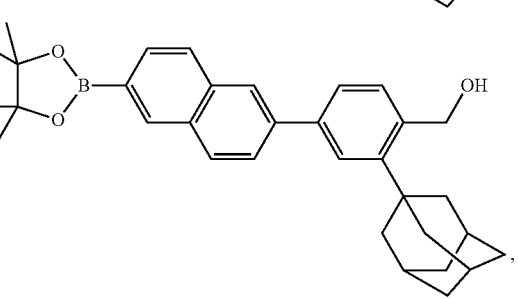
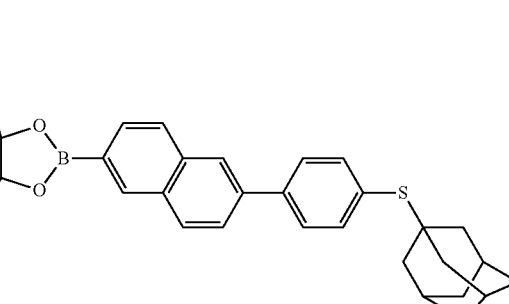
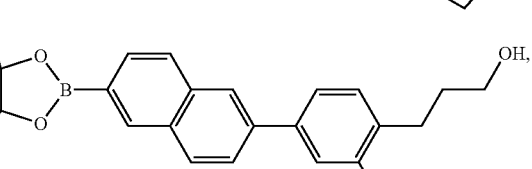

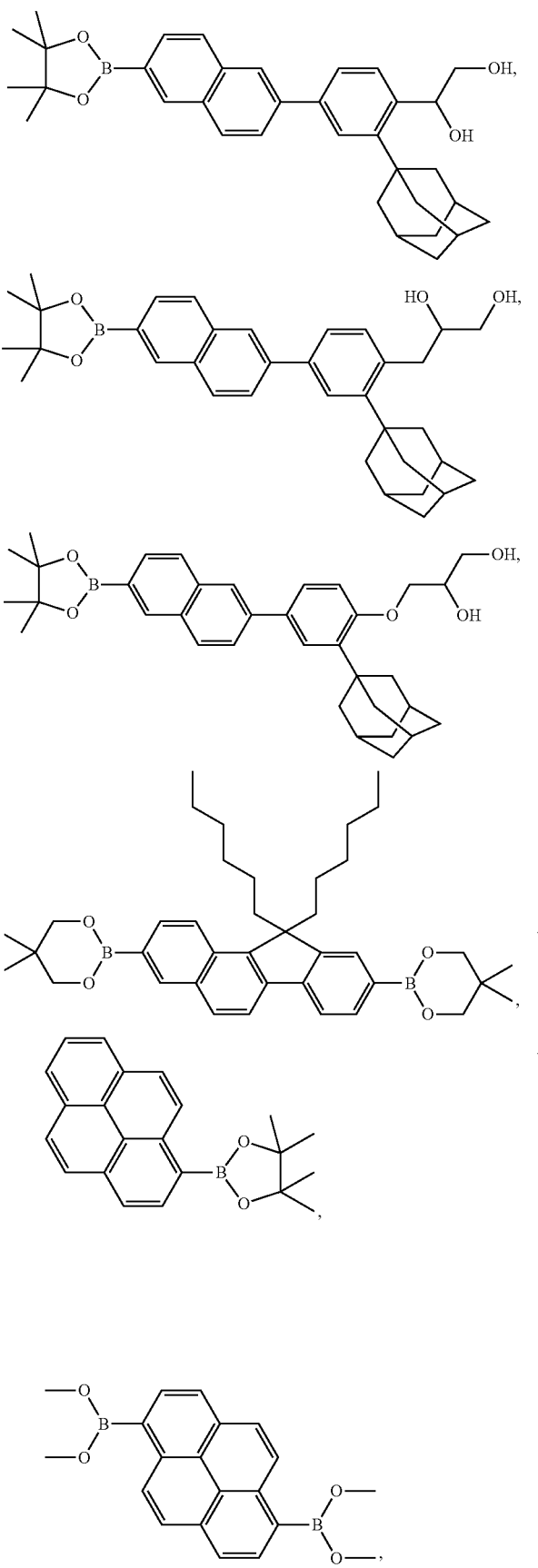
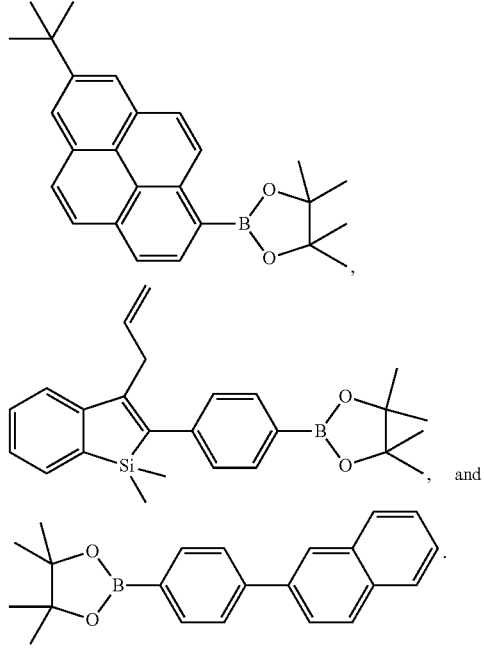

3. A method of treating cancer in a subject, the method comprising administering to the subject an inhibitor of sterol regulatory binding protein 1 (SREBP1) of any of paragraphs 1-2.
4. The method of paragraph 3, further comprising a first step of selecting a subject having cancer cells which express abnormal levels of sterol regulatory binding protein 1 (SREBP1).
5. The method of paragraph 4, wherein the cells which express abnormal levels of sterol regulatory binding protein 1 (SREBP1) are cells which have abnormal levels of SREBP1 polypeptide.
6. The method of paragraph 3, further comprising a first step of selecting a subject having cancer cells which express abnormal amounts of Erb2.
7. The method of paragraph 3, further comprising a first step of selecting a subject having cancer cells which express abnormal amounts of at least one gene selected from the group consisting of: FASN, SCD1 or ACLY.
8. The method of any of paragraphs 3-7, wherein the subject has an endometrial cancer.
9. The method of any of paragraphs 3-8, wherein the cancer is selected from the group consisting of: prostate cancer; breast cancer; colorectal cancer; colorectal carcinoma; hepatocarcinoma; endometrial adenocarcinoma; uterine cancer; leukemia; lung cancer; central nervous system cancer; melanoma; ovarian cancer; renal cancer; and pancreatic cancer.
10. A pharmaceutical composition comprising a compound of any of paragraphs 1-2.
11. The composition of paragraph 10, further comprising a pharmaceutically acceptable carrier.
12. The use of an inhibitor of sterol regulatory binding protein 1 (SREBP1) of any of paragraphs 1-2 to treat cancer.
13. The use of paragraph 12, wherein the cancer is comprised of cells expressing abnormal levels of sterol regulatory binding protein 1 (SREBP1).
14. The use of paragraph 13, wherein the cells which express abnormal levels of sterol regulatory binding protein 1 (SREBP1) are cells which have abnormal levels of SREBP1 polypeptide.

15. The use of paragraph 12, wherein the cancer is comprised of cells expressing abnormal amounts of Erb2.
16. The use of paragraph 12, wherein the cancer is comprised of cells expressing abnormal amounts of at least one gene selected from the group consisting of: FASN, SCD1 or ACLY.
17. The use of any of paragraphs 12-16, wherein the cancer is an endometrial cancer.
18. The use of paragraph 17, wherein the cancer is selected from the group consisting of:
   prostate cancer; breast cancer; colorectal cancer; colorectal carcinoma; hepatocarcinoma; endometrial adenocarcinoma; uterine cancer; leukemia; lung cancer; central nervous system cancer; melanoma; ovarian cancer; renal cancer; and pancreatic cancer.

EXAMPLES

Example 1: Targeting Lipogenic Signaling to Repress Endometrial Cancer Cell Growth Significantly enhanced lipogenesis is a metabolic hallmark of rapidly proliferating tumor cells. Although most normal cells acquire the bulk of their fatty acids from circulation, tumor cells synthesize more than 90% of required lipids de novo. The sterol regulatory element-binding protein 1 (SREBP1), encoded by SREBP1 gene, is a master regulator of lipogenic gene expression. Although it is known that SREBP1 and its target genes are overexpressed in a variety of cancers, the role of SREBP1 in endometrial cancer (EC) is largely unknown. Herein, a panel of endometrial cancer specimens was screened for their lipogenic gene expression by quantitative PCR and a significant increase in mRNA abundance of SREBP1, SREBP2, and FASN genes was found in cancer compared to normal endometrium. Immunohistochemical staining confirmed SREBP1 protein overexpression and further demonstrated increased nuclear distribution of SREBP1 in EC. SREBP1 promotes cellular proliferation in cell culture and enhances tumor growth in a xenograft model. Knockdown of endogenous SREBP1 gene impaired the viability of cells cultured in medium supplemented with lipid-depleted serum. The small molecule BF175 repressed SREBP1-dependent gene expression and cell growth and induced EC cell death. All together, the results presented herein established a role of SREBP1 in EC cell growth and validated BF175 for its therapeutic effectiveness in targeting SREBP1 and lipogenesis to block EC proliferation.

Introduction

The number of women with newly diagnosed endometrial cancer (EC) increased by 20% from 1987; however the number of deaths posted a 168% increase during the same time period. Estimated new cases and deaths from EC in the United States in 2011 are 46,470 and 8,120, respectively (data available on the world wide web at http://www.cancer.gov/cancertopics/types/endometrial). Epidemiological studies have identified obesity as the most common risk factor for EC. Obese women have a 2-4 times greater risk of developing EC compared to women of normal weight, regardless of menopausal status (1-5). As population size affected by this disease is expected to grow, particularly in developing countries, EC will continue to be a serious public health problem. Sterol regulatory element binding proteins (SREBPs) are a family of transcription factors that regulate lipid homeostasis by controlling the expression of multiple enzymes required for cholesterol and fatty acids (FAs) synthesis. The three SREBP isoforms, SREBP1a, SREBP1c and SREBP2, have different roles in lipid synthesis (6,7). In vivo studies using transgenic and knockout mice suggest that SREBP1c is involved in FA synthesis and insulin-induced glucose metabolism (particularly in lipogenesis), whereas SREBP2 is relatively specific in controlling cholesterol synthesis. The SREBP1a isoform is implicated in regulating both cholesterol and FA pathways. SREBP transcription factors are synthesized as inactive precursors bound to the endoplasmic reticulum (ER) membranes and their processing is mainly controlled by cellular sterol content. When sterol level decreases, the precursor undergoes a sequential two-step cleavage process to release the NH2-terminal active domain in the nucleus (designated nSREBPs), which then activate SREBP target genes to maintain cholesterol and FAs homeostasis (8-15). The major SREBP targets include FASN (16,17) and stearoyl-CoA desaturase (SCD) (18-21). This sterol-sensitive process appears to be a major point of regulation for the SREBP1a and SREBP2 isoforms but not for SREBP1c. Moreover, the SREBP1c isoform is mainly regulated at the transcriptional level by insulin. The unique regulation and activation properties of each SREBP isoform facilitate the co-ordinate regulation of lipid metabolism. At a minimum, SREBP1 activity refers to the ability of the amino-terminal active domain of SREBP1a to transactive expression from an SRE-containing gene or reporter gene construct. As noted, SREBP targets include FASN and SCD. Accordingly, an inhibitor of SREPB1 activity will inhibit SRE-mediated transactivation by the amino-terminal active domain of SREBP1a. A reporter construct comprising, for example, a regulatory element comprising one or more SREs can be used to monitor that effect of an SREBP1 inhibitor on SREBP1-mediated transactivation. Examples of suitable reporter constructs include the FASN and SCD promoter-driven luciferase reporter constructs described herein in Example 1 and the reporter constructs (e.g. the FAS, ACLY, LDLR, HMG, and FPP reporters) described in Amemiya-Kudo et al. Journal of Lipid Research 2002 43:1220-1235, which is incorporated by reference herein in its entirety.

Lipogenesis is a highly active process in many human cancers. The regulatory function of SREBP1 suggests a role in sensing and regulating cancer-associated lipogenesis. Increased expression of SREBP1 has been reported in colorectal carcinoma, breast and prostate cancer, and hepatocarcinoma. Moreover, elevated expression of SREBP1 coincided with malignant transformation, cancer progression, and metastasis for several cancer types, particularly hormone-responsive tissues including breast and prostate cancers (22-25). SREBP1 expression correlates with FASN and Ki-67 expression in colorectal cancer, indicating a role for SREBP1 in supporting rapid cellular proliferation (25). SREBP1 is elevated in clinical prostate cancer samples compared to benign prostatic hypertrophy (26). Gene expression profiling of hepatocellular carcinoma (HCC) tissue and non-cancerous liver tissue showed increased lipogenic signaling in HCC. Enhanced SREBP1 expression in hepatocellular carcinoma predicts an increased mortality (22,23). Over-expression of SREBP1 in human hepatoma HuH7 and Hep3B cells enhanced cellular proliferation and foci formation while siRNA knockdown of SREBP1 in these cells reduced cell replication and anchorage-independent cell growth (22). A dramatic increase of SREBP1 has been correlated with the progression of prostate cancer towards androgen-independence (26). Oncogene transformation of normal breast epithelial cells was accompanied by SREBP1 and FASN over-expression, consistent with the observation of increased SREBP1 abundance in human breast cancers (27-29). Previous studies have established that SREBP1, through induction of FASN and subsequent fatty acids production, regulates PPARγ trans-activation (16,30).

Despite the relatively clear understanding of enhanced lipogenic signaling, the role of SREBP1 in endometrial cancer is still largely unknown. Given the evidence of elevated expression of SREBP1 transcriptional target genes, the primary focus of this study was to determine the SREBP1 expression status in, for example, endometrial cancer. Demonstrated herein is increased nuclear staining for SREBP1 in higher grade tumors, suggesting that enhanced SREBP1 transactivation may contribute to endometrial cancer progression through induction of lipogenic gene expression and lipogenesis. Knockdown of endogenous SREBP1 expression using a shRNA approach results in a reduction of SREBP1 target gene expression as well as impaired cellular proliferation and migration. Furthermore, a small molecule inhibitor of lipogenic signaling, BF175, is demonstrated to repress tumor cell growth by targeting SREBP1-mediated signaling.

Results

Increased SREBP1 Expression in Endometrial Cancer.

Previous studies indicated that lipogenic genes such as FASN are overexpressed in endometrial cancers. The underlying mechanisms through which EC cells overexpress FASN are not well understood. SREBP1 is the major transcription factor which binds to FASN gene promoter and positively regulates FASN expression. It was hypothesized that elevated SREBP1 expression and/or activity may contribute to enhanced FASN expression in EC. In order to determine the levels of SREBP1 expression, immunohistochemical staining was performed on formalin-fixed, paraffin-embedded sections using anti-SREBP1 antibody. Nuclear and cytoplasmic SREBP1 abundance was scored for both matured and precursor forms, respectively. SREBP1 was detected in both normal and cancerous tissues. SREBP1 was found to be overexpressed in poorly-differentiated EC. Nuclear localization of SREBP1 was frequently seen in poorly-differentiated tumors (grade 2-3), but not in well-differentiated tumors (grade 1) (FIG. 1A and data not shown). The majority of SREBP1 was found in the cytoplasm of epithelial cells of normal endometrium and well-differentiated tumors, while nuclear SREBP1 was detected in high-grade from moderately differentiated to poorly differentiated tumors (FIGS. 2A-2F). These observations suggest a role of activated SREBP1 in endometrial cancer progression.

SREBP1 abundance was regulated at either transcriptional or post-translational levels (31,32). The increased protein expression may be due to enhanced gene expression. To confirm this, quantitative real-time PCR (qRT-PCR) analysis was performed on a panel of cDNA samples prepared from surgically resected samples and the transcript levels of SREBPs and SCD1, a transcriptional target of SREBPs, was compared between normal and cancerous tissues. As shown in FIG. 1A, cancer tissue exhibited markedly reduced SREBP1a and SREBP2. No significant difference of SREBP1c expression was observed. Meanwhile, the mRNA levels of SCD1 were significantly increased in cancer, which keeps in line with increased SREBP1 protein expression and activation as evidenced by nuclear translocation. Reduced mRNA expression and increased protein abundance suggest mechanisms by which SREBP1 protein is stabilized in cancer.

SREBP1 is Responsible for Lipogenic Gene Expression in Endometrial Cancer Cells.

Figure 2A:
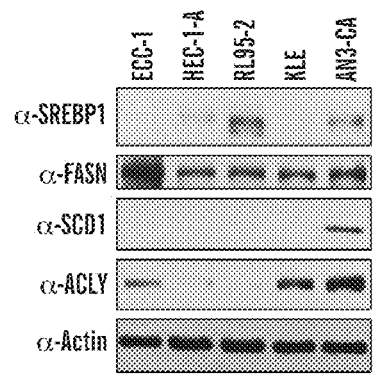
Figure 2B:
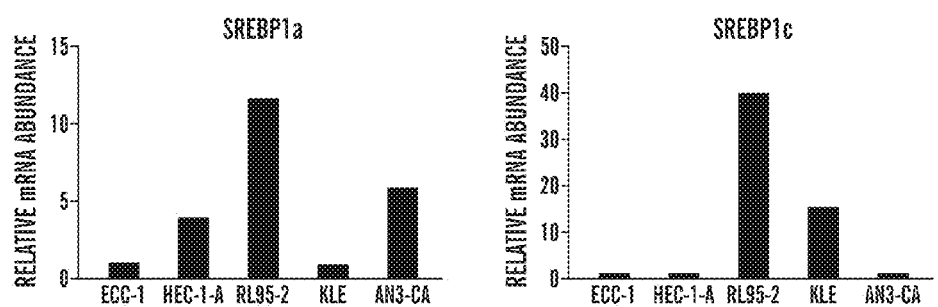

Having established the correlation between SREBP1 expression and endometrial cancer progression, it was determined whether SREBP1 contributes to tumorigenesis. In order to do so, an initial screening for SREBP1 expression was performed in five commonly used endometrial cell lines including ECC, HEC-1-A, RL95-2, KLE, and AN3-CA. SREBP1 expression was undetectable in the well-differentiated ECC-1 cells and highly expressed in medium and poorly differentiated RL95-2 and AN3-CA cells (data not shown). Since SREBP1 antibody cannot differentiate SREBP1a and SREBP1c, qRT-PCR was performed to determine which SREBP1 isoform was predominantly expressed. As shown in FIG. 2B, the RL95-2 cells express both isoforms at relatively high levels. AN3-CA expresses SREBP1a, but not SREBP1c. The expression levels of SREBP target genes including FASN, SCD, and ACLY were also determined. Relatively high expression of FASN, SCD1, and ACLY were detected in AN3-CA cells (FIG. 2A). AN3-CA cells were chosen for most experiments in this study due to the relatively high levels of lipogenic gene expressions. To test whether the endogenous SREBP1 is required for lipogenic gene expression, SREBP1 gene expression was knocked-down using a shRNA approach (33). Over 90% knockdown efficiency was achieved at both protein and mRNA levels (FIG. 2C). The expression of SREBP1 target genes was also significantly reduced (FIG. 2D), indicating a partial SREBP1 dependency of these genes.

SREBP1 is Required for Cellular Proliferation and Migration.

Cell proliferation is tightly controlled by mitogenic signaling and requires the activation of biosynthetic pathways for the generation of macromolecules, including proteins and lipids. Given the evidence that SREBP1 regulates lipogenesis, the metabolic process that supplies cells with lipids, it was expected that the knockdown of endogenous SREBP1 would reduce cellular proliferation and cell growth. In order to determine the functional consequences of SREBP1 inactivity in cell culture, cells with either knockdown of SREBP1 by shRNA or vector control were compared. The same number of each group of cells were seeded and counted for 5 days. Reduced cell number was observed in shSREBP1 expressing cells (FIG. 2E). It has been previously shown that suppression of lipogenic signaling reduces cellular migration. To test whether SREBP1 is involved in cell migration, transwell assays were conducted, in which the knockdown of endogenous SREBP1 significantly inhibited the cell migration (FIG. 2F).

BF175, a Small Molecule Inhibitor, Represses Lipogenesis In Vivo.

Figure 3A:
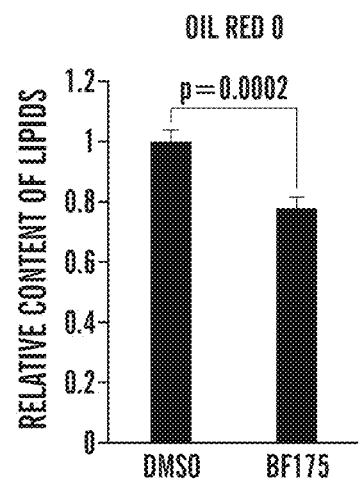
FIGS. 3A-3E demonstrate pharmacological inhibition by BF175 represses lipid formation and lipogenic gene expression.

To further examine whether BF175 has any effect in regulating lipid homeostasis, Drosophila larvae were fed fly food containing 100 μM of BF175 from hatching to the third instar larvae. Lipids were then stained and quantified with Oil Red O. As shown in FIG. 3A, the wild-type larvae fed with 100 μM of BF175 in food have 20~25% reduction of the fat levels compared to the control food with DMSO. Similar results were observed with 50 uM or 200 uM of BF175, or BF102, a compound similar to BF175. These results suggest that BF175 (and BF102) has a conserved role in inhibiting lipogenesis in whole organisms. At 200 μM, both compounds do not affect the Drosophila development and viability, and adult flies fed with food mixed with these compounds also do not have any obvious effect on life span (data not shown), suggesting that these compounds are not toxic to *Drosophila*.

BF175 Represses SREBP1 Activity and Lipogenic Gene Expression.

Figure 3B:
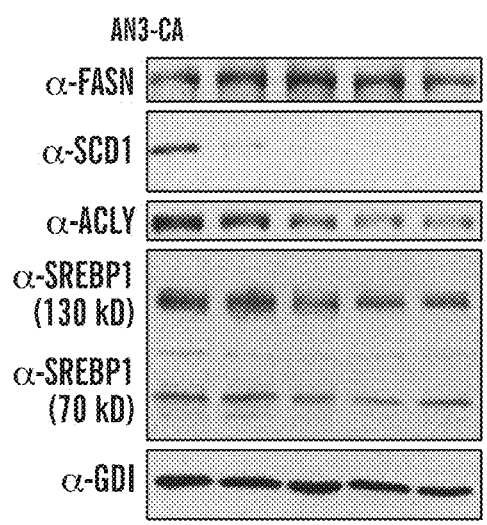
Figure 3C:
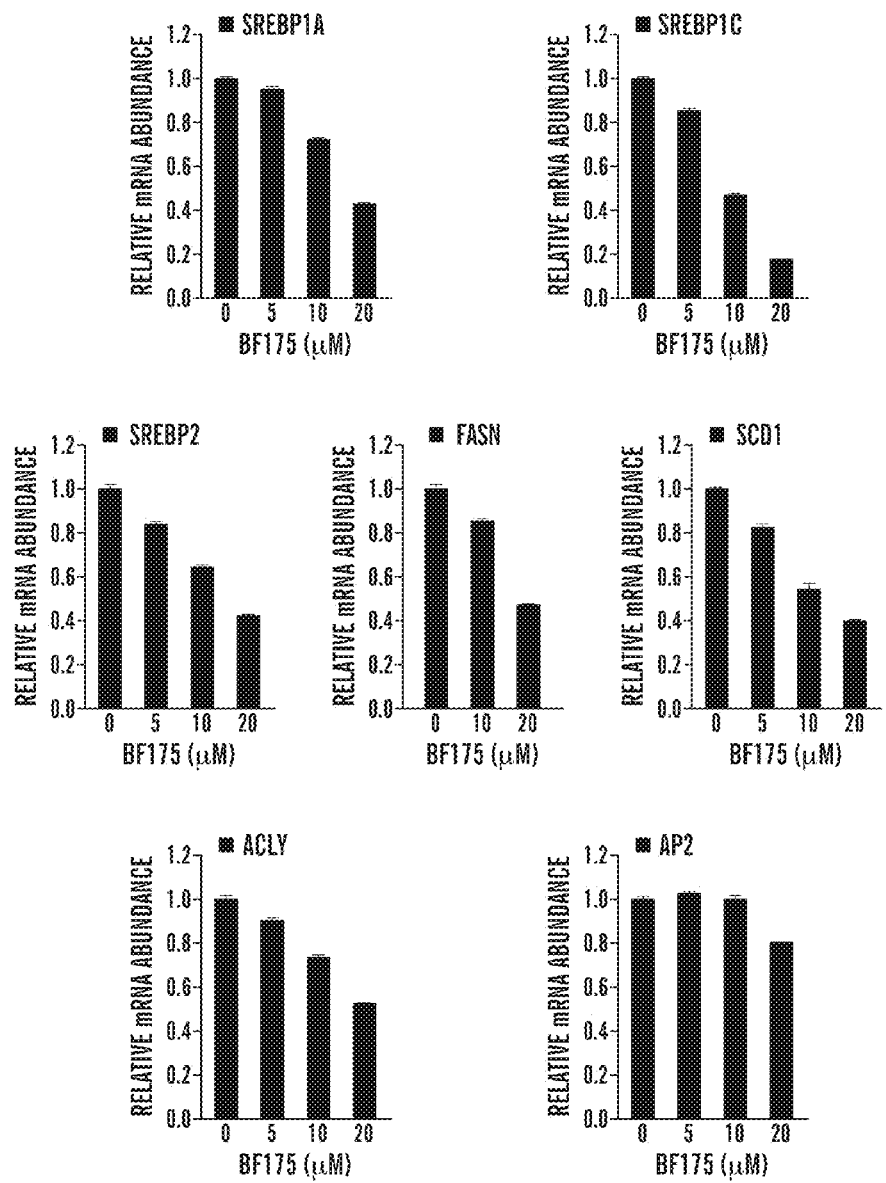

It was investigated whether that inhibition of lipogenic signaling could provide therapeutic intervention of endometrial cancer progression. BF175 repression of lipogenesis suggests that tumor cell growth might be alleviated by this agent. AC3-CA cells were treated with increased doses of BF175. BF175 markedly reduced the protein expression of ACLY and SCD1, as well as FASN to a lesser extent (FIG. 3B). This is consistent with the observation made above herein, that the knockdown of SREBP1 only led to 30% reduction of FASN mRNA levels (FIG. 2D). Previous reports also showed that FASN gene expression is controlled by multiple signaling pathways (16,25,27,35-38). qRT-PCR assays were conducted to determine the mRNA levels of these genes in cells treated with BF175. All three forms of SREBPs were significantly repressed. The expression of FASN, SCD and ACLY genes were also inhibited (FIG. 3C). The pyruvate kinase (PK) encoded by the PKLR gene is involved in lipogenesis, but not regulated by SREBP1. No change in PKLR gene expression was observed in cells exposed to BF175, suggesting SREBP1-specific signaling is targeted. It is no surprise to see that the mRNA expression of SREBPs was also repressed since SREBP1 positively regulates its gene expression through a feed-forward mechanism (31).

Figure 3D:
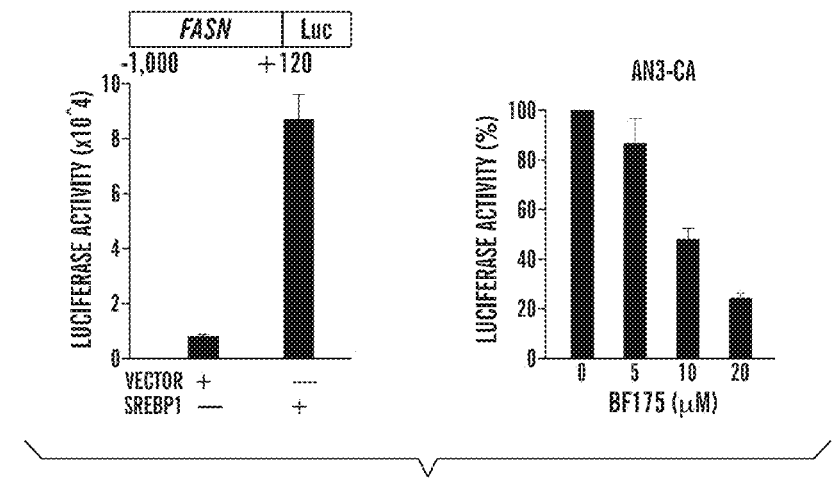
Figure 3E:
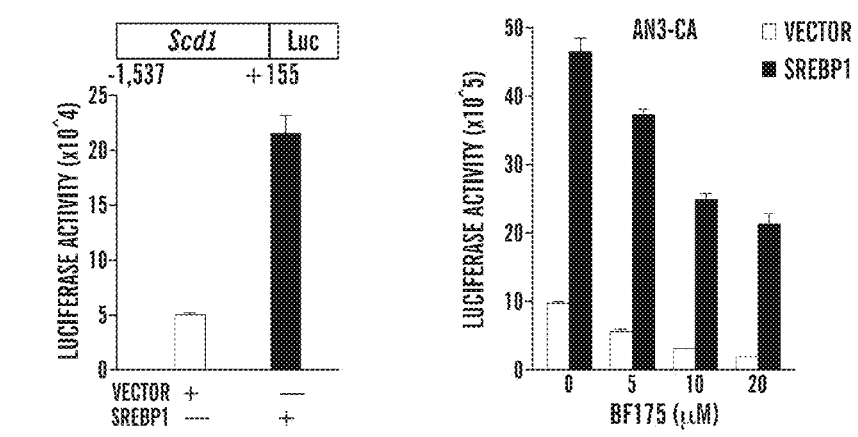

Both SCD and FASN are transcriptional targets of SREBP1. Using the FASN or SCD promoter-driven luciferase reporter as surrogate measures of SREBP1 activity (FIG. 3D, 3E), it was determined whether BF175 regulates the gene expression by targeting their transcription. Experiments were conducted in AN3-CA and human embryonic kidney HEK 293 cells showing that BF175 potently represses FASN and SCD reporter activity in a dose-dependent manner (FIG. 3D, 3E).

BF175 Inhibits Endometrial Cancer Cell Growth.

Since the results described above herein demonstrate that SREBP1 is required for cellular proliferation and BF175 targeted SREBP1 for repression, it was next tested whether BF175 inhibition of SREBP1 could reduce cell growth. Five cell lines were incubated with different doses of BF175 for 24 hrs, and MTT assays were conducted to measure cell viability. BF175 treatment significantly inhibited the growth of AN3-CA and RL95-2 cells. Little or no effect was observed in ECC1, HEC1A and KLE cells, where lower SREBP1 expression was detected (FIG. 4A). These results further confirmed that BF175 functions in an SREBP1-dependent manner. Cell growth was also determined by the total cell number in BF175 treated cells, showing a significant reduction of cells in a dose dependent manner (FIG. 4B)

To better understand the mechanisms by which BF175 inhibition of SREBP1 impairs cell growth, AN3-CA cells were starved with serum-free medium for 48 hrs, then released by supplying cells with 10% serum and BrdU in the presence and absence of BF175. After 6 hrs, cells were stained for BrdU incorporated in the newly synthesized DNA. BrdU-positive cells were counted and calculated as a percentage of total cell number. No significant change in the number of BrdU-positive cells was found between BF175 treated and control groups (FIG. 4C), indicating that SREBP1 inhibition by BF175 does not block DNA synthesis in response to mitogen signaling.

BF175-Dependent Induction of Apoptotic and Autophagic Cell Death.

Figure 5A:
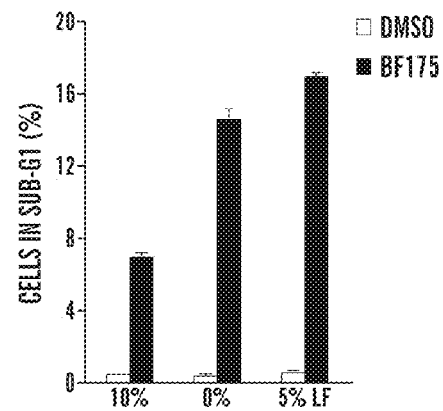
FIGS. 5A-5B demonstrate that BF175 induces cell death.
Figure 5B:
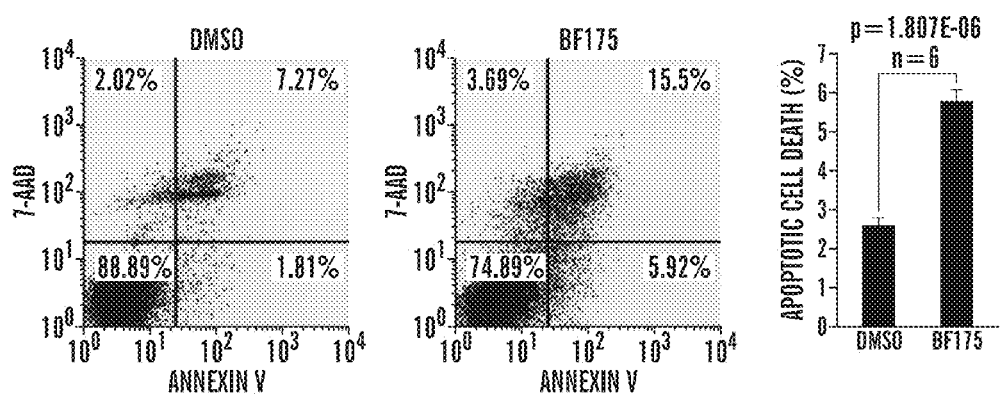

It has been previously shown that inhibition of SREBP1 sensitizes cells to death ligand and evasion of cell death contributes to the net cell growth (39). It has been hypothesized that BF175 inhibition of cell growth could also be due to the enhanced cell death. To test this idea, several approaches were used. First, the sub-G1 population of cells treated with BF175 or control were analyzed. Cells treated with BF175 for 24 hrs were subjected to flow cytometry assays, showing that BF175 markedly increased the cells in sub-G1 cell population (FIG. 5A). BF175-treated cells were also analyzed by Annexin V staining to determine the apoptotic cell death. Cells that are in early apoptosis are Annexin V positive and 7-AAD negative; while cells that are in late apoptosis are both Annexin V and 7-AAD positive. As demonstrated in FIG. 5B, the percentage of early apoptotic cells increased from 1.81% to 5.92%, a three-time induction of cell death by BF175. This observation was further confirmed by TUNEL staining showing a dramatic increase of apoptotic cell death in the presence of BF175 (data not shown). A primary cellular response to nutrient deprivation is the induction of autophagy. Whether blockage of SREBP1 induces cells to undergo autophagy was examined. AN3-CA cells were transduced with retroviral vector encoding GFP-LC3 or GFP as previously described (40). GFP-positive cells enriched by FACs sorting were treated with BF175. An increased number of punctate dots, indicative of autophagosome accumulation, were found in BF175 treated cells (data not shown).

BF175 Represses SREBP1-Dependent Transcription.

Figure 6A:
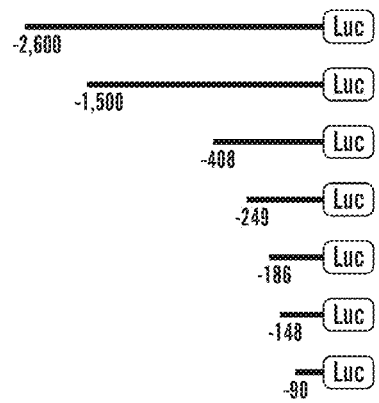
FIGS. 6A-6D demonstrate that BF175 targets SREBP1 and inhibits SREBP1-dependent gene transcription. (6A, 6C). Schematic maps of luciferase reporters driven by SREBP1 promoters. (6B, 6D). AN3-CA cells were transiently transfected with SREBP1 promoter reporter plasmids and treated with increasing doses of BF175 for 24 hrs before the luciferase activity was measured.
Figure 6B:
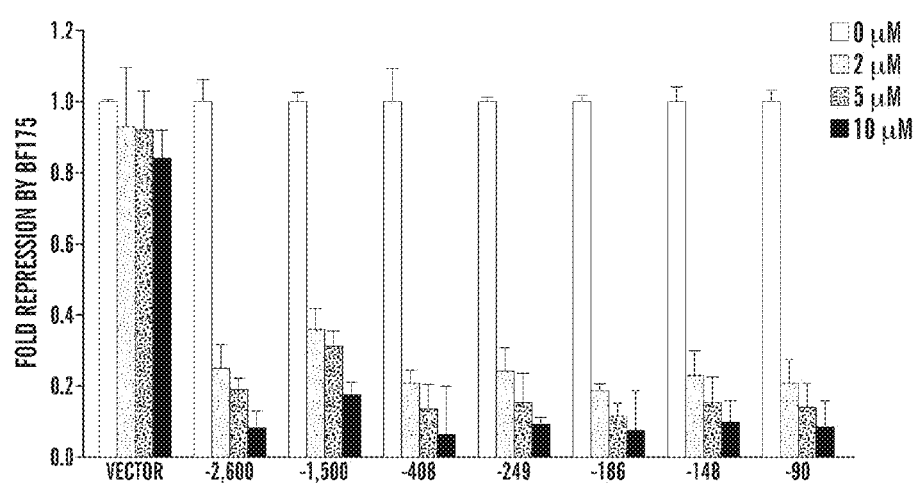
Figure 6C:
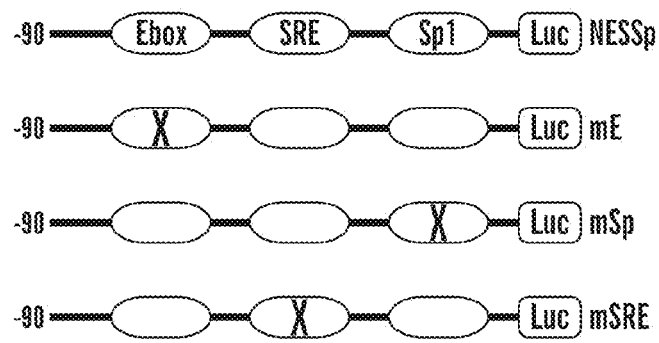
Figure 6D:
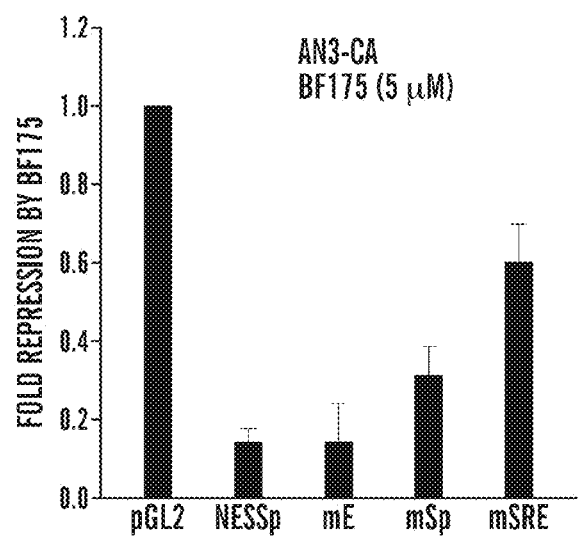
Figure 7:
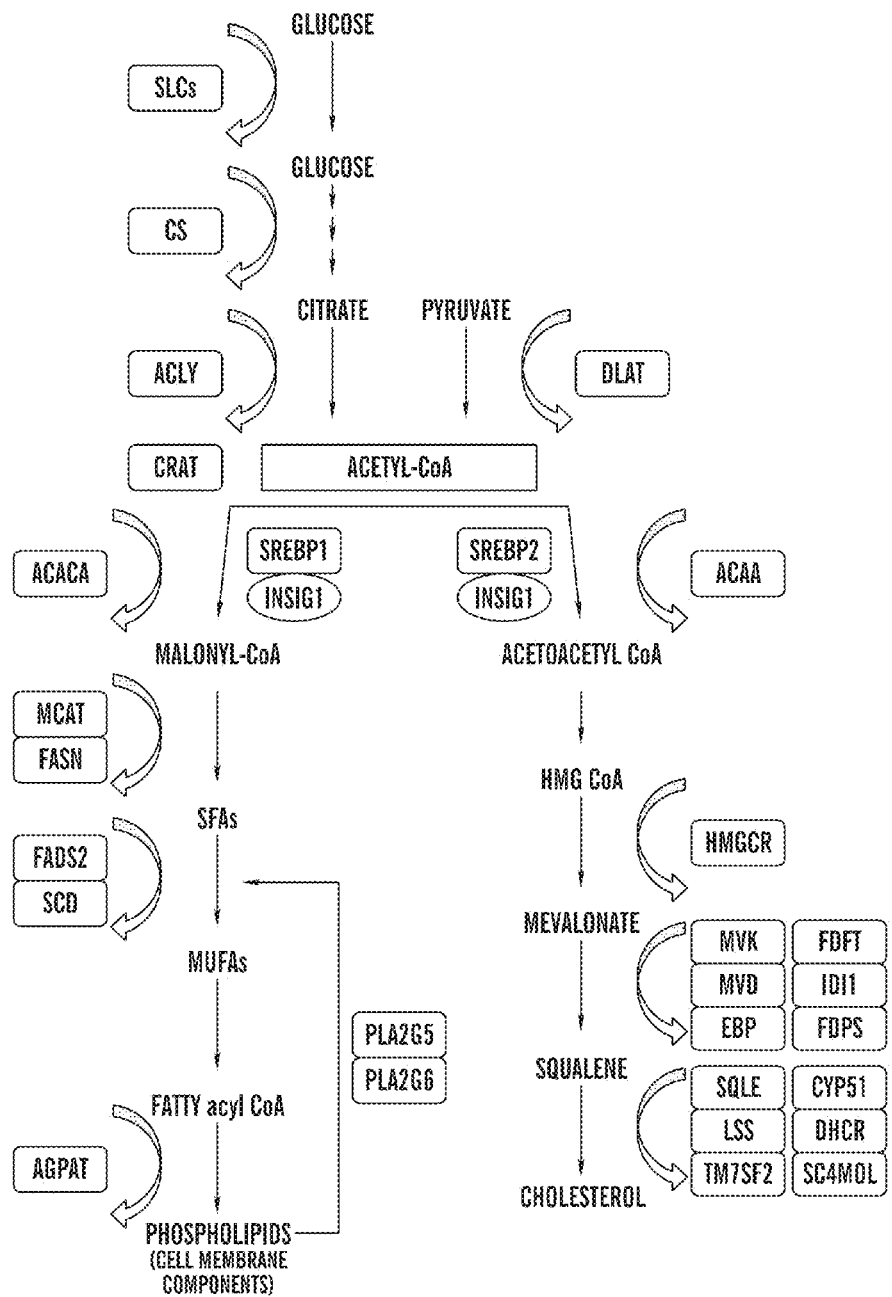
FIG. 7 depicts a schematic of SREBP1-related pathways in lipogenesis.
Figure 8:
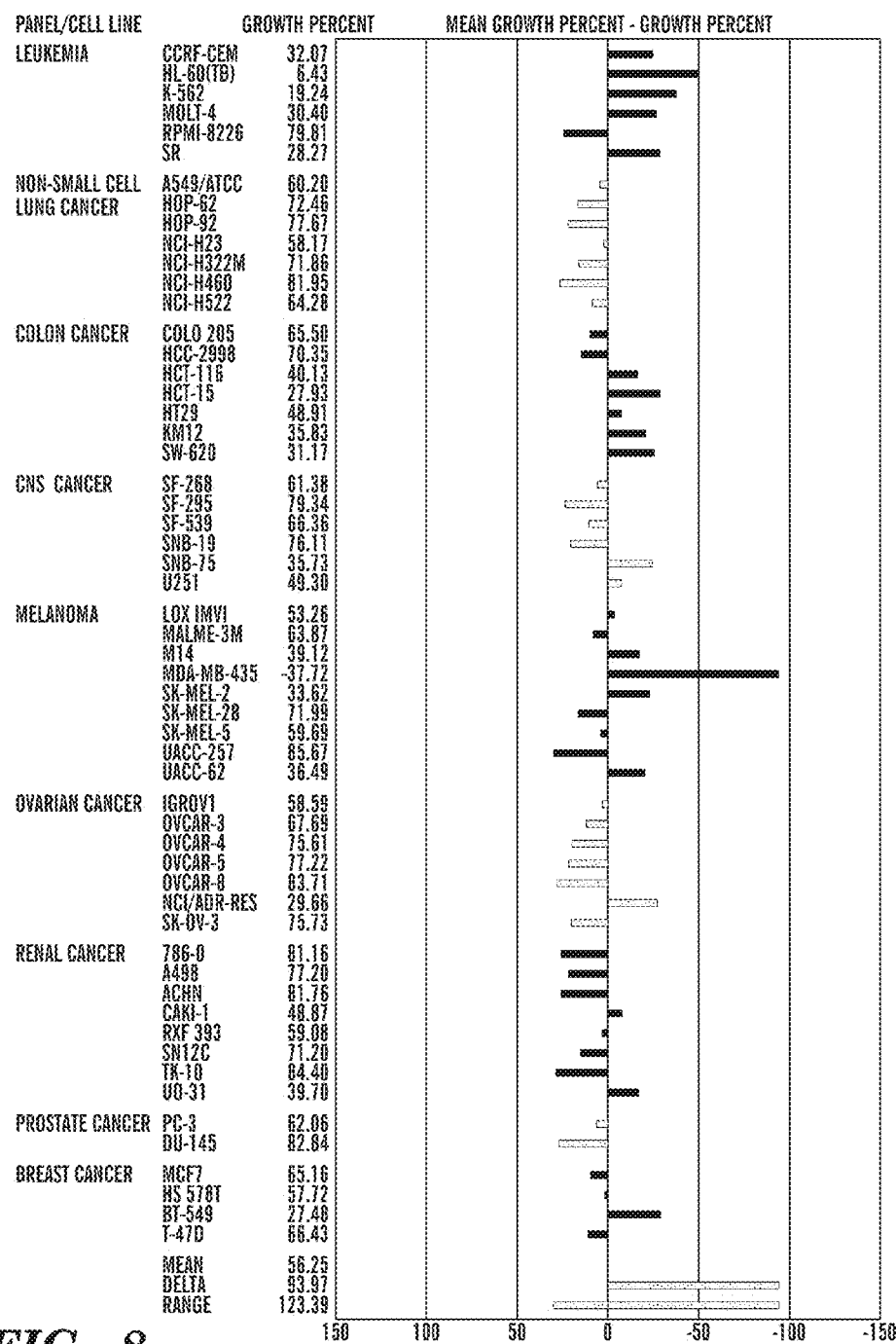
FIG. 8 depicts a mean graph of the percent growth of cells treated with BF175 when compared to control cells.

To understand mechanistically how BF175 regulates SREBP1 activity, an assay using SREBP1 gene promoter driven luciferase reporter as described previously (41) was conducted. The truncated promoter reporter was first tested for responsiveness to BF175 (FIG. 6A). The minimal promoter (90-bp) reporter activity was repressed equally well as the full-length (2,600-bp), suggesting the responsive element was restricted to the 90 base pairs of SREBP1 promoter region. As previously identified, Ebox, SRE and Sp1 were main sites within this region. Using promoter reporter with mutation of each individual site as illustrated in FIG. 6C, it was demonstrated that SRE mutant reporter is less responsive to BF175 repression, suggesting that SREBPs, rather than Ebox or Sp1 binding proteins, were targeted by BF175 (FIG. 6D).

Discussion

The results described herein establish a role of SREBP1 in endometrial cancer cell proliferation. Enhanced lipogenic gene expression and lipogenesis are required for cancer cell proliferation. It has been previously established that lipogenic signaling controls cellular proliferation. By targeting SREBP1 expression and/or activity using shRNA and pharmacological approaches, it is possible to block the cell growth. The SREBP1 gene knockdown experiment described herein established a role of SREBP1 in supporting cellular proliferation and migration.

Tumor growth is the net gain of cell population, which is contributed to by both cell proliferation and cell death. BF175 treatment reduced cell viability and total cells numbers as measured by MTT assay. BF175 did not inhibit BrdU incorporation into newly synthesized DNA, suggesting that BF175 may not block the G1/S transition, which is a critical step for rapidly proliferating cells. Knockdown of SREBP1 expression sensitizes cells to lipid depletion and leads to cell death under lipid-free culture condition (data not shown).

This is in complete agreement with the observation that BF175 induces cell death.

The current study addressed an important question of whether SREBP1 is responsible for enhanced lipogenesis in tumors, which contributes to cancer progression. Targeting SREBP1 activity provides an approach to repress cell growth. It is demonstrated herein that synthetic SREBP1 inhibitors are effective in blocking cancer cell growth by inhibiting cellular proliferation and by inducing cell death. BF175 and its analogs can serve as lead compounds for pharmacological intervention in cancer progression.

Materials and Methods

Endometrial Cancer Specimens and Immunohistochemistry (IHC) Staining.

Formalin-fixed and paraffin-embedded tumor specimens used in this study were from a commercial source (Creative Biolabs, Shirley, N.Y.) and from the tissue bank of the 90$^{th}$ Hospital of Jinan, China. All tumors were primary and untreated before surgery with complete clinicopathological information. All patients received radical mastectomy or modified radical mastectomy; the axillary lymph nodes were routinely dissected, and lymph node metastasis was determined based on histological examination. Tumor size was defined as the maximum tumor diameter measured on the tumor specimens at the time of operation. Endometrial cancer tissues from the 90$^{th}$ Hospital of Jinan were built into a 60-core array with 2 mm diameter of the core size. Adjacent normal tissues were included for some cancer tissues.

IHC staining for SREBP1 was performed on the paraffin-embedded tissue blocks in the Kimmel Cancer Center Pathology Core Facility at Thomas Jefferson University. Hematoxylin and eosin (H&E) staining were reviewed to ensure the cancer tissue and normal epithelia. IHC staining for these markers was performed on 5-µm thick sections. Briefly, tissue slides were de-paraffinized with xylene and rehydrated through a graded alcohol series. The endogenous peroxidase activity was blocked by incubation in a 3% hydrogen peroxide solution for 15 minutes. Antigen retrieval was carried out by immersing the slides in 10 mM sodium citrate buffer (pH 6.0) and maintained at a sub-boiling temperature for 5 minutes. The slides were rinsed in phosphate-buffered saline and incubated with 10% normal serum to block non-specific staining. The slides were then incubated with the primary antibody (anti-SREBP1, K-10, Santa Cruz) overnight at 4° C. in a humidified chamber.

All staining was assessed by pathologists blinded to the origination of the samples using a semi-quantitative method. The widely accepted German semi-quantitative scoring system in considering the staining intensity and area extent was used. Each specimen was assigned a score according to the intensity of the nucleic and cytoplasmic staining (no staining=0; weak staining=1, moderate staining=2, strong staining=3) and the extent of stained cells (0%=0, 1-10%=1, 11-50%=2, 51-80%=3, 81-100%=4). The final immunoreactive score was determined by multiplying the intensity score with the extent of score of stained cells, ranging from 0 (the minimum score) to 12 (the maximum score). SREBP1 expression was defined as low (scored 0-4), medium (score 5-8), and high (9-12).

Plasmids, Antibodies, and Reagents.

shRNA targeting human SREBP1 was described previously (33). The 1000-bp promoter of FASN was amplified from genomic DNA of AN3-CA cells and subcloned into Kpn I/Bgl II of pGL3-basic vector (Promega). Mouse Scd1 promoter-driven luciferase reporter was described previously (42). pcDNA3-FLAG-SREBP1a was obtained from Addgene (43). All the mutant constructs for SREBP1 promoter-driven luciferase reporter were described previously (41). The retroviral vector (MSCV-IRES-GFP) expressing GFP-LC3 was described previously by the inventors (40). Anti-SREBP1 (K-10 and H-160), anti-FASN (H300), anti-actin (C4) were purchased from Santa Cruz Biotechnology (Santa Cruz, Calif.). Anti-SCD (MC38) was purchased from Cell Signaling Technology (Danvers, Mass.). Anti-ACLY was from Abcam (Cat.# ab40993, Cambridge, Mass.).

Cell Culture.

The human embryonic kidney 293T cells (HEK293T) were maintained in DMEM containing 1% penicillin/streptomycin and supplemented with 10% fetal bovine serum (FBS). Endometrial cancer cell lines including ECC-1, HEC-1A, RL95-2, KLE, and AN3-CA were purchased from the American Type Culture Collection (ATCC). The basal culture medium are: RPMI-1640 (ECC-1), McCoy's 5a (HEC-1A), DMEM:F12 (RL95-2, KLE), and Eagle's Minimum Essential Medium (AN3-CA). For cell maintenance, the basal medium was supplemented with 10% fetal bovine serum (FBS). Under lipid-free culture condition as indicated, the basal medium was supplemented with 5% lipid-depleted FBS purchased from Cocalico Biologicals (Reamstown, Pa.) (Cat. #55-0116).

Transfection, Transduction and Luciferase Reporter Assays.

For transient transfection, SUPERFECT™ transfection reagent was used following manufacturer's protocol (Qiagen, Valencia, Calif.). For cell transduction, retroviruses were prepared by transient co-transfection with helper virus into HEK 293T cells using calcium phosphate precipitation. HEK 293T cells were transfected with plasmid DNA and cultured at 37° C. for 6 hrs, the medium was replaced and after 36 h the supernatant was collected and filtered through a 0.45 µm filter. Cells were infected at approximately 70% confluence in DMEM supplemented with 8 µg/ml of polybrene. The following day the medium was changed to basal medium supplemented with 10% FBS and cultured for further assay.

Luciferase assays were performed as previously described (44). Briefly, cells were seeded at 50% confluence in a 24-well plate on the day prior to transfection. Cells were transiently transfected with the appropriate combination of the reporter (300 ng per well), expression vectors (calculated as molar concentration equal to 300 ng of control vector), and control vector (300 ng per well) via calcium phosphate precipitation for HEK 293T or LIPOFECTAMINE 2000™ (Invitrogen, Carlsbad, Calif.) for remaining cell lines according to the manufacturer's instructions. 24 hours post transfection, luciferase assays were performed at room temperature using an AUTOLUMAT LB 953™ (EG&G Berthold). The data are shown as mean±SEM from at least two separate experiments with triplicate samples each.

RNA Isolation, Quantitative Real-Time PCR.

Total RNA was prepared using TRIZOL™ reagent (Invitrogen, Carlsbad, Calif.) following manufacturer's instructions. 5 µg of total RNA was subjected to reverse transcription to synthesize cDNA using the SUPERSCRIPT™ II Reverse Transcriptase Kit (Invitrogen, Carlsbad, Calif.). A 25 µl volume reaction consisted of 1 µl reverse transcription product and 100 nM of each primer. The primers used for qRT-PCR are listed as below:

TABLE 1

| Gene symbol | Forward primer sequence | Seq ID No: | Reverse primer sequence | SEQ ID No: | Amplicon size |
|---|---|---|---|---|---|
| SREBP1a | 5'-CGGCGCTGCTGACCGACATC | 13 | 5'-CCCTGCCCCACTCCCAGCAT | 22 | 104 bp |
| SREBP1c | 5'-GCGCAGATCGCGGAGCCAT | 14 | 5'-CCCTGCCCCACTCCCAGCAT | 23 | 116 bp |
| SREBP2 | 5'-CAAGCTTCTAAAGGGCATCG | 15 | 5'-AGTAGGGAGAGAAGCCAGCC | 24 | 140 bp |
| FANS | 5'-CACAGGGACAACCTGGAGTT | 16 | 5'-ACTCCACAGGTGGGAACAAG | 25 | 97 bp |
| SCD1 | 5'-CGACGTGGCTTTTTCTTCTC | 17 | 5'-CCTTCTCTTTGACAGCTGGG | 26 | 70 bp |
| ACLY | 5'-GCCCATCCCCAACCAGCCAC | 18 | 5'-TTGCAGGCGCCACCTCATCG | 27 | 137 bp |
| ADIPOQ | 5'-TCCTGCCAGTAACAGGGAAG | 19 | 5'-AGGGGAAGTGTCAGTACCCG | 28 | 168 bp |
| aP2 | 5'-CTCTCCGTTCAGATTGAAGGGG | 20 | 5'-AATCCCGCCTCCATCCTAACT | 29 | 122 bp |
| GAPDH | 5'-GAGTCAACGGATTTGGTCGT | 21 | 5'-TTGAGGTCAATGAAGGGGTC | 30 | 103 bp |

Cellular Proliferation, Migration and Apoptosis Assays.

Cells were stably transfected with shRNA targeting SREBP1 and control were subjected to TRANSWELL™ migration assays. Cells were seeded on an 8 μm-pore size TRANSWELL™ filter insert (Costar) coated with ECM (Sigma, St. Louis, Mo.) at a density of $1 \times 10^4$ cells in each well in DMEM containing 10% FBS. After 6 h of incubation at 37° C. and 5% $CO_2$, cells adherent to the upper surface of the filter were removed using a cotton applicator. Cells were stained with 0.4% crystal violet dissolved in methanol, and the numbers of cells on the bottom were counted. Data are from at least three experiments done in triplicate (mean±SEM).

TRANSWELL™ migration assays were described in our prior publications (45,46). $2.5 \times 10^4$ cells were seeded on an 8 m-pore size TRANSWELL™ filter insert (Corning Inc., Corning, N.Y.) coated with ECM (1:7.5) (Sigma, St. Louis, Mo.). After 6 h of incubation at 37° C. and 5% $CO_2$, cells adherent to the upper surface of the filter were removed using a cotton applicator. Cells were stained with 0.4% crystal violet dissolved in methanol, and the numbers of cells on the bottom were counted.

Cell death was determined by PE Annexin V Apoptosis Detection Kit (BD Biosciences) and TACS 2 TdT-DAB In Situ Apoptosis Detection Kit (Trevigen, Gaithersburg, Md.) following manufacturer's instructions.

Mixing the BF175 in the *Drosophila* Food, 1M stock solution of BF175, or BF102 are made in DMSO, and further diluted and mixed in melted fly food for the final concentrations of 50 uM, 100 uM and 200 uM, and the control food was mixed with the equivalent amount of DMSO. Wild-type (w1118) flies were allowed to embryos on these food and female larvae at the third instar wandering stage were analyzed for the Oil Red O staining.

Oil Red O Staining and Quantification.

*Drosophila* larvae were dissected in PBS and then fixed in 4% formalin in PBS for 15 min at room temperature. They were stained with 5 ml of 0.036% Oil Red O for 25 min, rinsed once with 70% isopropanol and distilled water. After being dried overnight, the Oil Red O from each larva was extracted in 0.3 ml of isopropanol and the O.D. at 510 nm was measured. One-tailed t-test was used for statistical analysis.

References
1. Bratos, K., Roszak, A., Cikowska-Wozniak, E., and Niecewicz, P. (2002) Ginekol Pol 73, 945-950
2. Gull, B., Karlsson, B., Milsom, I., and Granberg, S. (2001) Am J Obstet Gynecol 185, 386-391
3. Weiderpass, E., Persson, I., Adami, H. O., Magnusson, C., Lindgren, A., and Baron, J. A. (2000) Cancer Causes Control 11, 185-192
4. Shoff, S. M., and Newcomb, P. A. (1998) Am J Epidemiol 148, 234-240
5. Goodman, M. T., Hankin, J. H., Wilkens, L. R., Lyu, L. C., McDuffie, K., Liu, L. Q., and Kolonel, L. N. (1997) Cancer Res 57, 5077-5085
6. Hua, X., Wu, J., Goldstein, J. L., Brown, M. S., and Hobbs, H. H. (1995) Genomics 25, 667-673
7. Edwards, P. A., Tabor, D., Kast, H. R., and Venkateswaran, A. (2000) Biochim Biophys Acta 1529, 103-113
8. Wang, X., Zelenski, N. G., Yang, J., Sakai, J., Brown, M. S., and Goldstein, J. L. (1996) EMBO J 15, 1012-1020

9. Wang, X., Sato, R., Brown, M. S., Hua, X., and Goldstein, J. L. (1994) Cell 77, 53-62
10. Hua, X., Yokoyama, C., Wu, J., Briggs, M. R., Brown, M. S., Goldstein, J. L., and Wang, X. (1993) Proc Natl Acad Sci USA 90, 11603-11607
11. Yokoyama, C., Wang, X., Briggs, M. R., Admon, A., Wu, J., Hua, X., Goldstein, J. L., and Brown, M. S. (1993) Cell 75, 187-197
12. Briggs, M. R., Yokoyama, C., Wang, X., Brown, M. S., and Goldstein, J. L. (1993) J Biol Chem 268, 14490-14496
13. Wang, X., Briggs, M. R., Hua, X., Yokoyama, C., Goldstein, J. L., and Brown, M. S. (1993) J Biol Chem 268, 14497-14504
14. Shimano, H. (2001) Prog Lipid Res 40, 439-452
15. Horton, J. D., and Shimomura, I. (1999) Curr Opin Lipidol 10, 143-150
16. Kim, J. B., and Spiegelman, B. M. (1996) Genes Dev 10, 1096-1107
17. Liang, G., Yang, J., Horton, J. D., Hammer, R. E., Goldstein, J. L., and Brown, M. S. (2002) J Biol Chem 277, 9520-9528
18. Bene, H., Lasky, D., and Ntambi, J. M. (2001) Biochem Biophys Res Commun 284, 1194-1198
19. Ntambi, J. M. (1999) J Lipid Res 40, 1549-1558
20. Tabor, D. E., Kim, J. B., Spiegelman, B. M., and Edwards, P. A. (1999) J Biol Chem 274, 20603-20610
21. Shimomura, I., Shimano, H., Korn, B. S., Bashmakov, Y., and Horton, J. D. (1998) J Biol Chem 273, 35299-35306
22. Yamashita, T., Honda, M., Takatori, H., Nishino, R., Minato, H., Takamura, H., Ohta, T., and Kaneko, S. (2009) J Hepatol 50, 100-110
23. Yahagi, N., Shimano, H., Hasegawa, K., Ohashi, K., Matsuzaka, T., Najima, Y., Sekiya, M., Tomita, S., Okazaki, H., Tamura, Y., Iizuka, Y., Nagai, R., Ishibashi, S., Kadowaki, T., Makuuchi, M., Ohnishi, S., Osuga, J., and Yamada, N. (2005) Eur J Cancer 41, 1316-1322
24. Yang, Y. A., Morin, P. J., Han, W. F., Chen, T., Bornman, D. M., Gabrielson, E. W., and Pizer, E. S. (2003) Exp Cell Res 282, 132-137
25. Li, J. N., Mahmoud, M. A., Han, W. F., Ripple, M., and Pizer, E. S. (2000) Exp Cell Res 261, 159-165
26. Ettinger, S. L., Sobel, R., Whitmore, T. G., Akbari, M., Bradley, D. R., Gleave, M. E., and Nelson, C. C. (2004) Cancer Res 64, 2212-2221
27. Furuta, E., Pai, S. K., Zhan, R., Bandyopadhyay, S., Watabe, M., Mo, Y. Y., Hirota, S., Hosobe, S., Tsukada, T., Miura, K., Kamada, S., Saito, K., Iiizumi, M., Liu, W., Ericsson, J., and Watabe, K. (2008) Cancer Res 68, 1003-1011
28. Yoon, S., Lee, M. Y., Park, S. W., Moon, J. S., Koh, Y. K., Ahn, Y. H., Park, B. W., and Kim, K. S. (2007) J Biol Chem 282, 26122-26131
29. Yang, Y. A., Han, W. F., Morin, P. J., Chrest, F. J., and Pizer, E. S. (2002) Exp Cell Res 279, 80-90
30. Kim, J. B., Wright, H. M., Wright, M., and Spiegelman, B. M. (1998) Proc Natl Acad Sci USA 95, 4333-4337
31. Chen, G., Liang, G., Ou, J., Goldstein, J. L., and Brown, M. S. (2004) Proc Natl Acad Sci USA 101, 11245-11250
32. Walker, A. K., Yang, F., Jiang, K., Ji, J. Y., Watts, J. L., Purushotham, A., Boss, O., Hirsch, M. L., Ribich, S., Smith, J. J., Israelian, K., Westphal, C. H., Rodgers, J. T., Shioda, T., Elson, S. L., Mulligan, P., Najafi-Shoushtari, H., Black, J. C., Thakur, J. K., Kadyk, L. C., Whetstine, J. R., Mostoslavsky, R., Puigserver, P., Li, X., Dyson, N. J., Hart, A. C., and Naar, A. M. (2010) Genes Dev 24, 1403-1417
33. Taghibiglou, C., Martin, H. G., Lai, T. W., Cho, T., Prasad, S., Kojic, L., Lu, J., Liu, Y., Lo, E., Zhang, S., Wu, J. Z., Li, Y. P., Wen, Y. H., Imm, J. H., Cynader, M. S., and Wang, Y. T. (2009) Nat Med 15, 1399-1406
34. Das, B. C., Zhao, X., Tang, X. Y., and Yang, F. (2011) Bioorg Med Chem Lett 21, 5638-5641
35. Van de Sande, T., De Schrijver, E., Heyns, W., Verhoeven, G., and Swinnen, J. V. (2002) Cancer Res 62, 642-646
36. Porstmann, T., Griffiths, B., Chung, Y. L., Delpuech, O., Griffiths, J. R., Downward, J., and Schulze, A. (2005) Oncogene 24, 6465-6481
37. Bennett, M. K., Lopez, J. M., Sanchez, H. B., and Osborne, T. F. (1995) J Biol Chem 270, 25578-25583
38. Choi, W. I., Jeon, B. N., Park, H., Yoo, J. Y., Kim, Y. S., Koh, D. I., Kim, M. H., Kim, Y. R., Lee, C. E., Kim, K. S., Osborne, T. F., and Hur, M. W. (2008) J Biol Chem 283, 29341-29354
39. Eberhard, Y., Gronda, M., Hurren, R., Datti, A., MacLean, N., Ketela, T., Moffat, J., Wrana, J. L., and Schimmer, A. D. (2011) Oncotarget 2, 186-196
40. Zhou, J., Zhang, W., Liang, B., Casimiro, M. C., Whitaker-Menezes, D., Wang, M., Lisanti, M. P., Lanza-Jacoby, S., Pestell, R. G., and Wang, C. (2009) Int J Biochem Cell Biol 41, 2334-2342
41. Amemiya-Kudo, M., Shimano, H., Yoshikawa, T., Yahagi, N., Hasty, A. H., Okazaki, H., Tamura, Y., Shionoiri, F., Iizuka, Y., Ohashi, K., Osuga, J., Harada, K., Gotoda, T., Sato, R., Kimura, S., Ishibashi, S., and Yamada, N. (2000) J Biol Chem 275, 31078-31085
42. Chu, K., Miyazaki, M., Man, W. C., and Ntambi, J. M. (2006) Mol Cell Biol 26, 6786-6798
43. Toth, J. I., Datta, S., Athanikar, J. N., Freedman, L. P., and Osborne, T. F. (2004) Mol Cell Biol 24, 8288-8300
44. Wang, C., Fu, M., D'Amico, M., Albanese, C., Zhou, J. N., Brownlee, M., Lisanti, M. P., Chatterjee, V. K., Lazar, M. A., and Pestell, R. G. (2001) Mol Cell Biol 21, 3057-3070
45. Zhou, J., Liu, Y., Zhang, W., Popov, V. M., Wang, M., Pattabiraman, N., Sune, C., Cvekl, A., Wu, K., Jiang, J., Wang, C., and Pestell, R. G. (2010) J Biol Chem
46. Meng, H., Tian, L., Zhou, J., Li, Z., Jiao, X., Li, W. W., Plomann, M., Xu, Z., Lisanti, M. P., Wang, C., and Pestell, R. G. (2011) Cell Cycle 10, 73-81

Example 2

According to the statistics published by American Cancer Society, about 1,596,670 new cancer cases were expected to be diagnosed in 2011. The National Cancer Institute estimates that approximately 11.7 million Americans with a history of cancer were alive in 2007. Epidemiological studies have identified obese and obesity as the most common risk factors for cancer. Obese patients have a 2-4 times greater risk of developing endometrial, breast and colon and liver cancers compared to population of normal weight. As population size affected by obese and obesity is expected to grow, particularly in developing countries, cancer will continue to be a serious public health problem. The significantly enhanced lipogenesis is a metabolic hallmark of rapidly proliferating tumor cells. Further, there is currently no effective therapy to target both obesity and cancer. Although most normal cells acquire the bulk of their fatty acids from circulation, tumor cells synthesize more than 90% of required lipids de novo. The sterol regulatory element-binding protein 1 (SREBP1), encoded by SREBP1 gene, as described herein, is a master regulator of lipogenic gene expression. The inventors' work has strongly associated altered lipogenic signaling in cancer with oncogene ErbB2 and estrogen receptor status in breast cancer.

To broadly explore possible targets of BF175, a microarray expression analysis of cells treated with BF175 compared to control was conducted. The microarray analyses detected that the mRNA expression of 472 genes was differentially increased, while that of 542 was decreased in BF175 treated cells. INGENUITY™ analysis of these BF175-regulated genes revealed "Lipid Metabolism" as the most significant function (Table 2). Of those BF175 down-regulated genes, 48 genes were directly involved in catalyzing and converting the glucose to produce either lipids or cholesterol (FIGS. 6A-6D, and Table 2). A considerable number of these BF175 genes have been reported as SREBP1 targets, including SREBP1 and SREBP2, suggesting that BF175 directly regulates SREBP1 activity. Furthermore, the significant overlap between this dataset and those from previously published SREBP1 gene signature again confirmed the specificity of BF175.

Example 3

NCI60 testing was performed in 59 cell lines with BF175 at a single dose of $10^{-5}$ molar. The one-dose data was reported as a mean graph of the percent growth of treated cells. The number reported for the one-dose assay is growth relative to the no-drug control, and relative to the time zero number of cells. This allows detection of both growth inhibition (values between 0 and 100) and lethality (values less than 0). For example, a value of 100 means no growth inhibition. A value of 40 would mean 60% growth inhibition. A value of 0 means no net growth over the course of the experiment. A value of −40 would mean 40% lethality. A value of −100 means all cells are dead.

The human tumor cell lines of the cancer screening panel were grown in RPMI 1640 medium containing 5% fetal bovine serum and 2 mM L-glutamine. Cells were inoculated into 96 well microtiter plates in 100 μL at plating densities ranging from 5,000 to 40,000 cells/well depending on the doubling time of individual cell lines. After cell inoculation, the microtiter plates were incubated at 37° C., 5% $CO_2$, 95% air and 100% relative humidity for 24 h prior to addition of BF175. After 24 h, two plates of each cell line were fixed in situ with TCA, to represent a measurement of the cell population for each cell line at the time of drug addition (Tz). BF175 was solubilized in dimethyl sulfoxide at 400-fold the desired final maximum test concentration and stored frozen prior to use. At the time of drug addition, an aliquot of frozen concentrate was thawed and diluted to twice the desired final maximum test concentration with complete medium containing 50 μg/ml gentamicin. Aliquots of 100 μl of these drug dilutions were added to the appropriate microtiter wells already containing 100 μl of medium, resulting in the required final drug concentrations.

Following drug addition, the plates were incubated for an additional 48 h at 37° C., 5% $CO_2$, 95% air, and 100% relative humidity. For adherent cells, the assay is terminated by the addition of cold TCA. Cells were fixed in situ by the gentle addition of 50 μl of cold 50% (w/v) TCA (final concentration, 10% TCA) and incubated for 60 minutes at 4° C. The supernatant was discarded, and the plates are washed five times with tap water and air dried. Sulforhodamine B (SRB) solution (100 μl) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm.

For suspension cells, the methodology is the same except that the assay was terminated by fixing settled cells at the bottom of the wells by gently adding 50 μl of 80% TCA (final concentration, 16% TCA). Using the absorbance measurements [time zero, (Tz), control growth, (C), and test growth in the presence of drug at $10^{-5}$ molar concentration of BF175 (Ti)], the percentage growth is calculated as: [(Ti−Tz)/(C−Tz)]×100 for concentrations for which Ti>/=Tz and [(Ti−Tz)/Tz]×100 for concentrations for which Ti<Tz.

TABLE 2

| Entrez ID | Gene symbol | Description | Fold change | P-value |
|---|---|---|---|---|
| 3156 | HMGCR | 3-hydroxy-3-methylglutaryl-CoA reductase | −1.96 | 0.0003 |
| 7108 | TM7SF2 | transmembrane 7 superfamily member 2/C-14 sterol reductase | −1.94 | 0.0000 |
| 3638 | INSIG1 | insulin induced gene 1 | −1.86 | 0.0000 |
| 1717 | DHCR7 | 7-dehydrocholesterol reductase | −1.79 | 0.0000 |
| 6576 | SLC25A1 | solute carrier family 25 (mitochondrial carrier; citrate transporter), member 1 | −1.78 | 0.0000 |
| 4598 | MVK | mevalonate kinase | −1.76 | 0.0013 |
| 6319 | SCD | stearoyl-CoA desaturase (delta-9-desaturase) | −1.74 | 0.0000 |
| 9415 | FADS2 | fatty acid desaturase 2 | −1.71 | 0.0004 |
| 1384 | CRAT | carnitine O-acetyltransferase | −1.71 | 0.0000 |
| 6307 | SC4MOL | sterol-C4-methyl oxidase-like | −1.71 | 0.0000 |
| 54947 | LPCAT2 | lysophosphatidylcholine acyltransferase 2 | −1.68 | 0.0009 |
| 3638 | INSIG1 | insulin induced gene 1 | −1.67 | 0.0007 |
| 3949 | LDLR | low density lipoprotein receptor | −1.67 | 0.0000 |
| 6721 | SREBF2 | sterol regulatory element binding transcription factor 2 | −1.67 | 0.0002 |
| 51181 | DCXR | dicarbonyl/L-xylulose reductase | −1.67 | 0.0000 |
| 2222 | FDFT1 | farnesyl-diphosphate farnesyltransferase 1 | −1.64 | 0.0000 |
| 6720 | SREBF1 | sterol regulatory element binding transcription factor 1 | −1.64 | 0.0144 |
| 29988 | SLC2A8 | solute carrier family 2 (facilitated glucose transporter), member 8 | −1.62 | 0.0000 |
| 11182 | SLC2A6 | solute carrier family 2 (facilitated glucose transporter), member 6 | −1.61 | 0.0000 |
| 30 | ACAA1 | acetyl-CoA acyltransferase 1 | −1.59 | 0.0000 |
| 4597 | MVD | mevalonate (diphospho) decarboxylase | −1.58 | 0.0001 |
| 10682 | EBP | emopamil binding protein (sterol isomerase) | −1.57 | 0.0201 |
| 6713 | SQLE | squalene epoxidase | −1.54 | 0.0000 |
| 79602 | ADIPOR2 | adiponectin receptor 2 | −1.54 | 0.0001 |
| 10162 | LPCAT3 | lysophosphatidylcholine acyltransferase 3 | −1.48 | 0.0004 |

TABLE 2-continued

| Entrez ID | Gene symbol | Description | Fold change | P-value |
|---|---|---|---|---|
| 10999 | SLC27A4 | solute carrier family 27 (fatty acid transporter), member 4 | −1.48 | 0.0063 |
| 3422 | IDI1 | isopentenyl-diphosphate delta isomerase 1 | −1.47 | 0.0001 |
| 1431 | CS | citrate synthase | −1.47 | 0.0058 |
| 6720 | SREBF1 | sterol regulatory element binding transcription factor 1 | −1.46 | 0.0002 |
| 1737 | DLAT | dihydrolipoamide S-acetyltransferase | −1.45 | 0.0015 |
| 47 | ACLY | ATP citrate lyase | −1.45 | 0.0017 |
| 3422 | IDI1 | isopentenyl-diphosphate delta isomerase 1 | −1.44 | 0.0000 |
| 2194 | FASN | fatty acid synthase | −1.44 | 0.0000 |
| 1595 | CYP51A1 | cytochrome P450, family 51, subfamily A, polypeptide 1 | −1.43 | 0.0241 |
| 55326 | AGPAT5 | 1-acylglycerol-3-phosphate O-acyltransferase 5 | −1.40 | 0.0018 |
| 2542 | SLC37A4 | solute carrier family 37 (glucose-6-phosphate transporter), member 4 | −1.40 | 0.0112 |
| 2224 | FDPS | farnesyl diphosphate synthase | −1.40 | 0.0010 |
| 10423 | CDIPT | CDP-diacylglycerol--inositol 3-phosphatidyltransferase | −1.38 | 0.0111 |
| 31 | ACACA | acetyl-CoA carboxylase alpha | −1.38 | 0.0001 |
| 27349 | MCAT | malonyl CoA: ACP acyltransferase (mitochondrial) | −1.37 | 0.0000 |
| 2639 | GCDH | glutaryl-CoA dehydrogenase | −1.36 | 0.0281 |
| 9926 | LPGAT1 | lysophosphatidylglycerol acyltransferase 1 | −1.35 | 0.0297 |
| 3795 | KHK | ketohexokinase (fructokinase) | −1.35 | 0.0010 |
| 11332 | ACOT7 | acyl-CoA thioesterase 7 | −1.34 | 0.0003 |
| 8310 | ACOX3 | acyl-CoA oxidase 3, pristanoyl | −1.34 | 0.0238 |
| 3417 | IDH1 | isocitrate dehydrogenase 1 (NADP+), soluble | −1.34 | 0.0003 |
| 4047 | LSS | lanosterol synthase (2,3-oxidosqualene-lanosterol cyclase) | −1.33 | 0.0033 |
| 3988 | LIPA | lipase A, lysosomal acid, cholesterol esterase | −1.30 | 0.0015 |

What is claimed herein is:

1. A compound selected from the group consisting of:

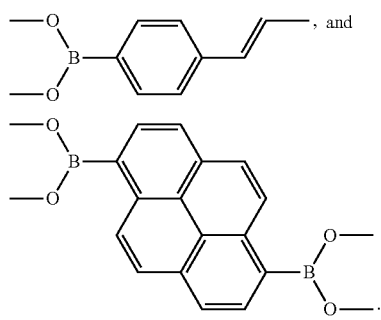

2. A pharmaceutical composition comprising a compound of claim 1.

3. The composition of claim 2, further comprising a pharmaceutically acceptable carrier.

* * * * *